US009914936B2

(12) United States Patent
Lawrence et al.

(10) Patent No.: US 9,914,936 B2
(45) Date of Patent: *Mar. 13, 2018

(54) NUCLEIC ACID SILENCING SEQUENCES

(71) Applicant: University of Massachusetts, Boston, MA (US)

(72) Inventors: Jeanne B. Lawrence, Mapleville, RI (US); Lisa L. Hall, Framingham, MA (US)

(73) Assignee: University of Massachusetts, Boston, MA (US)

( * ) Notice: Subject to any disclaimer, the term of this patent is extended or adjusted under 35 U.S.C. 154(b) by 20 days.

This patent is subject to a terminal disclaimer.

(21) Appl. No.: 15/074,785

(22) Filed: Mar. 18, 2016

(65) Prior Publication Data

US 2016/0264994 A1    Sep. 15, 2016

Related U.S. Application Data

(63) Continuation of application No. 14/045,057, filed on Oct. 3, 2013, now Pat. No. 9,297,023, which is a continuation of application No. 13/483,240, filed on May 30, 2012, now Pat. No. 8,574,900, which is a continuation of application No. 12/512,964, filed on Jul. 30, 2009, now Pat. No. 8,212,019.

(60) Provisional application No. 61/084,918, filed on Jul. 30, 2008.

(51) Int. Cl.
*C07H 21/02* (2006.01)
*C07H 21/04* (2006.01)
*A61K 48/00* (2006.01)
*C12N 15/85* (2006.01)
*C12N 9/22* (2006.01)
*C12N 15/113* (2010.01)
*C12N 15/86* (2006.01)
*C12N 15/90* (2006.01)

(52) U.S. Cl.
CPC ............ *C12N 15/85* (2013.01); *A61K 48/005* (2013.01); *C12N 9/22* (2013.01); *C12N 15/113* (2013.01); *C12N 15/86* (2013.01); *C12N 15/907* (2013.01); *A61K 48/00* (2013.01); *C07K 2319/81* (2013.01); *C12N 2310/11* (2013.01); *C12N 2320/32* (2013.01); *C12N 2330/10* (2013.01); *C12N 2750/14143* (2013.01)

(58) Field of Classification Search
CPC ...... A61K 48/00; C12N 15/111; C12N 15/113
See application file for complete search history.

(56) References Cited

U.S. PATENT DOCUMENTS 9,297,023 B2   3/2016 Lawrence et al.
2010/0160417 A1   6/2010 Lawrence et al.
2012/0142758 A1   6/2012 Collard et al.
2012/0252123 A1   10/2012 Lawrence et al.
2016/0143951 A1   5/2016 Lawrence et al.

OTHER PUBLICATIONS

Brockdorff and Duthie, "X Chromosome Inactivation and the Xist Gene," Cell. Mol. Life Sci., 1998, vol. 54, pp. 104-112.
Brown et al., "The Human Xist Gene: Analysis of a 17kb Inactive X-specific RNA That Contains Conserved Repeats and is Highly Localized Within the Nucleus," Cell, 1992, vol. 71, pp. 527-542.
Cathomen and Joung, "Zinc-finger Nucleases: The Next Generation Emerges," Molecular Therapy, Jun. 10, 2008, vol. 16(7), pp. 1200-1207.
Chow et al., "Inducible XIST-dependent X-chromosome Inactivation in Human Somatic Cells is Reversible," PNAS, Jun. 12, 2007, 104(24), pp. 10104-10109.
Greene and Lowrey, "The Human Xist Gene Promoter Prevents Silencing of an Integrated Reporter Gene," Blood, 2004, vol. 104 (11), Abstract #2114.
Hall et al., "An Ectopic Human XIST Gene can induce chromosome inactivation in postdifferentiation human HT-1080 cells," Proc Natl Acad Sci USA 99:8677-8682, 2002.
International Search Report and Written Opinion for PCT/US2009/052318, dated Apr. 30, 2010.
Lau et al., "Skewed X-Chromosome Inactivation Is Common in Fetuses or Newborns Associated with Confined Placental Mosaicism," Am. J. Hum. Genet., 61, pp. 1353-1361, 1997.
Migeon et al., "X Inactivation in Triploidy and Trisomy: The Search for Autosomal Transfactors That Choose the Active X," *European Journal of Human Genetics*, published on-line Oct. 31, 2007, 16, pp. 153-162, 2008.
Moehle et al., "Targeted gene addition into a specified location in the human genome using designed zinc finger nucleases," Proc Natl Acad Sci USA 104:3055-3060, 2007.
Porteus, "Mammalian Gene Targeting with Designed Zinc Finger Nucleases," Molecular Therapy, 2006, vol. 13(2), pp. 438-446.
Savarese et al., "Hematopoietic Precursor Cells Transiently Reestablish Permissiveness for X Inactivation," Molecular and Cellular Biology, 2006, vol. 26(19), pp. 7167-7177.
U.S. Patent and Trademark Office, Restriction Requirement in U.S. Appl. No. 12/512,964, dated Apr. 6, 2011, 9 pages.
Fish & Richardson P.C., Response to Restriction Requirement in U.S. Appl. No. 12/512,964, filed Jul. 6, 2011, 8 pages.
U.S. Patent and Trademark Office, Non Final Office Action in U.S. Appl. No. 12/512,964, dated Sep. 21, 2011, 12 pages.
Fish & Richardson P.C., Response to Office Action in U.S. Appl. No. 12/512,964, filed Jan. 23, 2012, 10 pages.

(Continued)

*Primary Examiner* — Amy H Bowman
(74) *Attorney, Agent, or Firm* — Fish & Richardson P.C.

(57) ABSTRACT

The present invention features compositions and methods for introducing, into cells, nucleic acids whose expression results in chromosomal silencing. The nucleic acids are targeted to specific chromosomal regions where they subsequently reduce the expression of deleterious genes, or cause the death of deleterious cells. Where the nucleic acid sequence is a silencing sequence, it may encode an Xist RNA or other non-coding, silencing RNA. Accordingly, the present invention features, inter alia, nucleic acid constructs that include a transgene (e.g., a silencing sequence encoding an Xist RNA or other non-coding RNA that silences a segment of a chromosome); first and second sequences that direct insertion of the silencing sequence into a targeted chromosome; and, optionally, a selectable marker.

32 Claims, 20 Drawing Sheets

(56) References Cited

OTHER PUBLICATIONS

U.S. Patent and Trademark Office, Notice of Allowance in U.S. Appl. No. 12/512,964, dated Mar. 5, 2012, 9 pages.
U.S. Patent and Trademark Office, Notice of Allowability in U.S. Appl. No. 12/512,964, dated Apr. 24, 2012, 5 pages.
U.S. Patent and Trademark Office, Restriction Requirement in U.S. Appl. No. 13/483,240, dated Oct. 11, 2012, 9 pages.
Fish & Richardson P.C., Response to Restriction Requirement in U.S. Appl. No. 13/483,240, filed Nov. 7, 2012, 6 pages.
Fish & Richardson P.C., Preliminary Amendment in U.S. Appl. No. 13/483,240, filed Nov. 16, 2012, 3 pages.
U.S. Patent and Trademark Office, Office Action in U.S. Appl. No. 13/483,240, dated Jan. 9, 2013, 9 pages.
Fish & Richardson P.C., Response to Office Action in U.S. Appl. No. 13/483,240, filed Mar. 26, 2013, 8 pages.
U.S. Patent and Trademark Office, Final Office Action in U.S. Appl. No. 13/483,240, dated May 28, 2013, 6 pages.
Fish & Richardson P.C., Response to Final Office Action in U.S. Appl. No. 13/483,240, filed Jun. 24, 2013, 6 pages.
U.S. Patent and Trademark Office, Notice of Allowance in U.S. Appl. No. 13/483,240, dated Jul. 3, 2013, 6 pages.
U.S. Patent and Trademark Office, Restriction Requirement in U.S. Appl. No. 14/045,057, dated Jan. 23, 2015, 9 pages.
Fish & Richardson P.C., Preliminary Amendment in Response to Restriction Requirement dated Jan. 23, 2015 in U.S. Appl. No. 14/045,057, filed Mar. 20, 2015, 6 pages.
U.S. Patent and Trademark Office, Office Action in U.S. Appl. No. 14/045,057, dated Apr. 27, 2015, 11 pages.
Fish & Richardson P.C., Response to Office Action in U.S. Appl. No. 14/045,057, filed Aug. 27, 2015, 8 pages.
U.S. Patent and Trademark Office, Final Office Action in U.S. Appl. No. 14/045,057, dated Sep. 15, 2015, 6 pages.
Fish & Richardson P.C., Response to Final Office Action in U.S. Appl. No. 14/045,057, filed Oct. 21, 2015, 4 pages.
U.S. Patent and Trademark Office, Notice of Allowance in U.S. Appl. No. 14/045,057, dated Nov. 19, 2015, 5 pages.
International Preliminary Report on Patentability (IPRP) mailed in Application No. PCT/US2009/052318 dated Feb. 1, 2011, enclosing Written Opinion dated Apr. 30, 2010.
Antonarakis et al., "The challenge of Down syndrome", Trends Mol Med., vol. 12:473-479 (2006).
Bailey et al., "Molecular evidence for a relationship between LINE-1 elements and X chromosome inactivation: The Lyon repeat hypothesis", PNAS, vol. 97:6634-6639 (2000).
Biancotti et al., "Human Embryonic Stem Cells as Models for Aneuploid Chromosomal Syndromes", Stem Cells, vol. 28:1530-1540 (2010).
Brockdorff, N. Chromosome silencing mechanisms in X-chromosome inactivation: unknown unknowns. Development 138, 5057-5065 (2011).
Brown et al., "Expression of genes from the human active and inactive X chromosomes", Am J Hum Genet, vol. 60:1333-1343 (1997).
Canzonetta et al., DYRK1A-Dosage Imbalance Perturbs NRSF/REST Levels, Deregulating Pluripotency and Embryonic Stem Cell Fate in Down Syndrome, The American Journal of Human Genetics, vol. 83:388-400, 2008.
Carrel et al., "X-inactivation profile reveals extensive variability in X-linked gene expression in females", Nature, vol. 434:400-404 (2005).
Chow et al., "Characterization of expression at the human XIST locus in somatic, embryonal carcinoma, and transgenic cell lines", Genomics, vol. 82:309-322 (2003).
Clemson et al., "The X chromosome is organized into a gene-rich outer rim and an internal core containing silenced nongenic sequences", Proc Natl Acad Sci USA 103, 7688-7693 (2006).
Clemson et al., "XIST RNA Paints the Inactive X Chromosome at Interphase: Evidence for a Novel RNA Involved in Nuclear/Chromosome Structure," J.Cell Biol., vol. 132:259-275 (1996).

Cotton et al., "Chromosome-wide DNA methylation analysis predicts human tissue-specific X inactivation", Human Genetics, vol. 130:187-201 (2011).
Csankovszki et al., "Synergism of XIST RNA, DNA Methylation, and Histone Hypoacetylation in Maintaining X Chromosome Inactivation", J. of Cell Biol., vol. 153:773-783 (2001).
Debrand et al., "Functional Analysis of the DXPas34 Locus, a 3' Regulator of Xist Expression," Mol. Cell. Bio., vol. 19:8513-8525 (1999).
DeKelver et al., "Functional genomics, proteomics, and regulatory DNA analysis in isogenic settings using zinc finger nuclease-driven transgenesis into a safe harbor locus in the human genome", Genome Research, vol. 20:1133-1142 (2010).
Douillard-Guilloux et al., "Partial phenotypic correction and immune tolerance induction to enzyme replacement therapy after hematopoietic stem cell gene transfer of—glucosidase in Pompe disease," J Gene Med., vol. 11:279-287 (2009).
Gardiner, K. J., "Molecular basis of pharmacotherapies for cognition in Down syndrome", Trends Pharmacol Sci., vol. 31:66-73 (2010).
Goodrich et al. "From bacteria to humans, chromatin to elongation, and activation to repression: The expanding roles of nonconding RNAs in regulating transcription", Crit. Rev. Biochem. Mol. Biol., vol. 44:3-15 (2009).
Guidi, et al., "Widespread Proliferation Impairment and Hypocellularity in the Cerebellum of Fetuses with Down Syndrome", Brain Pathol., vol. 21:361-373 (2011).
Hall et al., "Unbalanced X;autosome translocations provide evidence for sequence specificity in the association of XIST RNA with chromatin," Hum Mol Genet., vol. 11:3157-3165 (2002).
Hall, L. L. & Lawrence, J. B. The cell biology of a novel chromosomal RNA: chromosome painting by XIST/Xist RNA initiates a remodeling cascade. Semin Cell Dev Biol 14, 369-378 (2003).
Haydar et al., "Trisomy and early brain development," Trends Neurosci, vol. 35:81-91 (2012).
Heard, E., "Delving into the diversity of facultative heterochromatin: the epigenetics of the inactive X chromosome," Curr Opin Genet Dev., vol. 15:482-489 (2005).
Hockemeyer et al., "Efficient targeting of expressed and silent genes in human ESCs and iPSCs using zinc-finger nucleases," Nat Biotechnol, vol. 27:851-857 (2009).
International Preliminary Report on Patentability (IPRP) mailed in Application No. PCT/US2014/027525 dated Sep. 15, 2015, 10 pages.
International Search Report and Written Opinion for PCT/US2014/027525, dated Sep. 12, 2014 (13 pages).
Jiang, Jun et al., "Translating dosage compensation to trisomy 21", Nature, vol. 500:296-300, 2013.
Khalil et al., "Many human large intergenic noncoding RNAs associate with chromatin-modifying complexes and affect gene expression", PNAS, vol. 106:11667-11672 (2009).
Lavon et al., "Derivation of Euploid Human Embryonic Stem Cells from Aneuploid Embryos," Stem Cells, vol. 26:1874-1882 (2008).
Lee et al., "A 450 kb Transgene Displays Properties of the Mammalian X-Inactivation Center," Cell, vol. 86:83-94 (1996).
Lee, J. T., "Gracefully ageing at 50, X-chromosome inactivation becomes a paradigm for RNA and chromatin control," Nat Rev Mol Cell Bioll, vol. 12, 815-826 (2011).
Lepagnol-Bestel, Aude-Marie et al., "DYRK1A interacts with the REST/NRSF-SWI/SNF chromatin remodeling complex to deregulate gene clusters involved in the neuronal phenotypic traits of Down syndrome", Human Molecular Genetics, vol. 18(8):1405-1414, 2009.
Li et al., "Trisomy correction in down syndrome induced pluripotent stem cells," Cell Stem Cell, vol. 11:615-619 (2012).
Liu et al., "Mouse Models for Down Syndrome-Associated Developmental Cognitive Disabilities," Dev Neurosci, vol. 33:404-413 (2011).
Lockstone et al., "Gene expression profiling in the adult Down syndrome brain", Genomics, vol. 90:647-660 (2007).
Lyon, M., "Gene Action in the X-chromosome of the Mouse (*Mus musculus* L.)," Nature, vol. 190:372-373 (1961).

(56) References Cited

OTHER PUBLICATIONS

McNeil et al., "Word frequency analysis reveals enrichment of dinucleotide repeats on the human X chromosome and [GATA] n in the X escape region," Genome Research, vol. 16:477-484 (2006).

Megarbane, et al., "The 50th anniversary of the discovery of trisomy 21: The past, present, and future of research and treatment of Down syndrome," Genetics in medicine: official journal of the American College of Medical Genetics, vol. 11:611-616 (2009).

Miller et al., "An improved zinc-finger nuclease architecture for highly specific genome editing," Nat Biotechnol, vol. 25:778-785 (2007).

O'Doherty et al., "An Aneuploid Mouse Strain Carrying Human Chromosome 21 with Down Syndrome Phenotypes", Science, vol. 309:2033-2037 (2005).

Park et al., "Function and regulation of Dyrk1A: towards understanding Down syndrome," Cellular and molecular life sciences: CMLS, vol. 66:3235-3240 (2009).

Prandin et al., "Natural Gene-Expression Variation in Down Syndrome Modulates the Outcome of Gene-Dosage Imbalance", Am J Hum Genet., vol. 81:252-263 (2007).

Reeves, R. H. "Down syndrome mouse models are looking up", Trends Mol Med., vol. 12:237-240 (2006).

Sharp et al., "DNA methylation profiles of human active and inactive X chromosomes", Genome research, vol. 21:1592-1600 (2011).

Tam, R., Smith, K.P., and Lawrence, J.B. The 4q subtelomere harboring the FSHD locus is specifically anchored with peripheral heterochromatic unlike most human telomeres. Journal of Cell Biology 167, 269-279 (2004).

Tanzi et al., "Twenty Years of the Alzheimer's Disease Amyloid Hypothesis: a Genetic Perspective", Cell, vol. 120:545-555 (2005).

Urnov et al., Genome editing with engineered zinc finger nucleases, Nat Rev Genet., vol. 11:636-646 (2010).

Webb et al., β-Secretases, Alzheimer's Disease, and Down Syndrome, Curr Gerontol Geriatr Res, vol. 2012, Article ID 362839, 8 pages. (2012).

Wutz et al., "A shift from reversible to irreversible X inactivation is triggered during ES cell differentiation", Mol Cell, vol. 5:695-705 (2000).

Wutz et al., "Chromosomal silencing and localization are mediated by different domains of Xist RNA", Nat. Genetics, vol. 30:167-474 (2002).

Wutz et al., "Xinactivation Xplained", Curr. Opin. Genet Dev., vol. 17:387-393 (2007).

Wutz, A., "Gene silencing in X-chromosome inactivation: advances in understanding facultative heterochromatin formation", Nat Rev Genet, vol. 12:542-553 (2011).

Yabut et al., "Dyrk1A Overexpression Inhibits Proliferation and Induces Premature Neuronal Differentiation of Neural Progenitor Cells", J Neurosci, vol. 30:4004-4014 (2010).

Yahya-Graison et al., "Classification of Human Chromosome 21 Gene-Expression Variations in Down Syndrome: Impact on Disease Phenotypes", Am J Hum Genet, vol. 81:475-491 (2007).

```
   1 ccttcagttc ttaaagcgct gcaattcgct gctgcagcca tatttcttac tctctggggg
  61 ctggaagctt cctgactgaa gatctctctg cacttggggt tcttctaga acattttcta
 121 gtccccaac accctttatg gcgtatttct ttaaaaaaat cacctaaatt ccataaaata
 181 tttttttaaa ttctatactt tctcctagtg tcttcttgac acgtcctcca tattttttta
 241 aagaaagtat ttggaatatt ttgaggcaat ttttaatatt taaggaattt ttctttggaa
 301 tcatttttgg tgacatctct gttttttgtg gatcagtttt ttactcttcc actctctttt
 361 ctatattttg cccatcgggg ctgcggatac ctggttttat tattttttct ttgcccaacg
 421 gggccgtgga tacctgcctt ttaattcttt tttattcgcc catcggggcc gcggatacct
 481 gctttttatt ttttttttcct tagcccatcg gggtatcgga tacctgctga ttcccttccc
 541 ctctgaaccc ccaacactct ggcccatcgg ggtgacggat atctgctttt taaaaatttt
 601 cttttttttgg cccatcgggg cttcggatac ctgcttttttt ttttttttatt ttccttgccc
 661 atcggggcct cggataccotg ctttaatttt tgtttttctg cccatcgggg ccgcggatac
 721 ctgctttgat tttttttttt catcgcccat cggtgctttt tatggatgaa aaaatgttgg
 781 ttttgtgggt tgttgcactc tctggaatat ctacactttt ttttgctgct gatcatttgg
 841 tggtgtgtga gtgtacctac cgctttggca gagaatgact ctgcagttaa gctaagggcg
 901 tgttcagatt gtggaggaaa agtggccgcc atttttagact tgccgcataa ctcggcttag
 961 ggctagtcgt ttgtgctaag ttaaactagg gaggcaagat ggatgatagc aggtcaggca
1021 gaggaagtca tgtgcattgc atgagctaaa cctatctgaa tgaattgatt tggggcttgt
1081 taggagcttt gcgtgattgt tgtatcggga ggcagtaaga atcatctttt atcagtacaa
1141 gggactagtt aaaaatggaa ggttaggaaa gactaaggtg cagggcttaa aatggcgatt
1201 ttgacattgc ggcattgctc agcatggcgg gctgtgcttt gttaggttgt ccaaaatggc
1261 ggatccagtt ctgtcgcagt gttcaagtgg cgggaaggcc acatcatgat gggcgaggct
1321 ttgttaagtg gttagcatgg tggtggacat gtgcggtcac acaggaaaag atggcggctg
1381 aaggtcttgc cgcagtgtaa aacatgcgg gcctctttgt ctttgctgtg tgcttttcgt
1441 gttgggtttt gccgcaggga caatatggca ggcgttgtca tatgtatatc atggcttttg
1501 tcacgtggac atcatggcgg gcttgccgca ttgttaaaga tggcgggttt tgccgcctag
1561 tgccacgcag agcgggagaa aaggtgggat ggacagtgct ggattgctgc ataacccaac
1621 caattagaaa tgggggtgga attgatcaca gccaattaga gcagaagatg gaattagact
1681 gatgacacac tgtccagcta ctcagcgaag acctgggtga attagcatgg cacttcgcag
1741 ctgtctttag ccagtcagga gaaagaagtg gagggccac gtgtatgtct cccagtgggc
1801 ggtacaccag gtgttttcaa ggtcttttca aggacattta gcctttccac ctctgtcccc
1861 tcttatttgt ccoctcctgt ccagtgctgc ctcttgcagt gctggatatc tggctgtgtg
1921 gtctgaacct ccctccattc ctctgtattg gtgcctcacc taaggctaag tatacctccc
1981 cccccacccc ccaacccccc caactcccca ccccacccc ccaccccca cctccccacc
2041 ccctaccc cctaccccc tacccccct tggtctgccc tgcactgcac tgttgcccatg
2101 ggcagtgctc caggcctgct tggtgtggac atggtggtga gccgtggcaa ggaccagaat
2161 ggatcacaga tgatcgttgg ccaacaggtg gcagaagagg aattcctgcc ttcctcaaga
2221 ggaacaccta cccccttggct aatgctgggg tcggattttg atttatattt atcttttgga
2281 tgtcagtcat acagtctgat tttgtggttt gctagtgttt gaatttaagt cttaagtgac
2341 tattatagaa atgtattaag aggcttatt tgtagaattc actttaatta catttaatga
2401 gttttgttt tgagttcctt aaaattcctt aaagttttta gcttctcatt acaaattcct
2461 taaccttttt ttggcagtag atagtcaaag tcaaatcatt tctaatgttt taaaaatgtg
2521 ctggtcattt tctttgaaat tgacttaact attttccttt gaagagtctg tagcacagaa
2581 acagtaaaaa atttaacttc atgacctaat gtaaaaaaga gtgtttgaag gtttacacag
2641 gtccaggcct tgctttgttc ccatccttga tgctgcacta attgactaat cacctactta
2701 tcagacagga aacttgaatt gctgtggtct ggtgtcctct attcagactt attatattgg
2761 agtatttcaa ttttttcgttg tatcctgcct gcctagcatc cagttcctcc ccagccctgc
2821 tcccagcaaa ccctagtct agcccagcc ctactccac ccggccccag ccctgccca
2881 ggcccagtcc cctaccccc cagcctagg cccagtccca gtcctagttc ctcagtctgt
2941 ccagcttctc tcgaaagtca ctctaatttt cattgattca gtgtcaaaa taagttgtcc
3001 attggtatcc tattatactg ggatattccg tttaccttga gcattgctga tcttcagtac
3061 tgactccttg accatttcea gttaagcata caatcccatt tgtctgtgat ctcaggacaa
3121 agaatttcct tactcggtac gttgaagtta gggaatgtca attgagagct ttctatcaga
3181 gcattattgc ccacaatttg agttacttat cattttctcg atccoctgcc cttaaaggag
3241 aaaccatttc tctgtcattg cttctgtagt cacagtccca attttgagta gtgatcttttt
```

FIG. 6A

```
3301 cttgtgtact gtgttggcca cctaaaactc tttgcattga gtaaaattct aattgccaat
3361 aatcctaccc attggattag acagcactct gaacccatt tgcattcagc aggggtcgc
3421 agacaacccg tcttttgttg gacagttaaa atgctcagtc ccaattgtca tagctttgcc
3481 tattaaacaa aggcacccta ctgcgctttt tgctgtgctt ctggagaatc ctgctgttct
3541 tggacaatta agaacaaag tagtaattgc taattgtctc acccattaat catgaagact
3601 accagtcgcc cttgcatttg ccttgaggca gcgctgacta cctgagattt aagagtttct
3661 taaattattg agtaaaatcc caattatcca tagttctgtt agttacacta tggcctttgc
3721 aaacatcttt gcataacagc agtgggactg actcattctt agagccctt ccttggaat
3781 attaatggat acaatagtaa ttattcatgg ttctgcgtaa cagagaagac ccacttatgt
3841 gtatgccttt atcattgctc ctagatagtg tgaactacct accaccttgc attaatatgt
3901 aaaacactaa ttgcccatag tcccactcat tagtctagga tgtcctcttt gccattgctg
3961 ctgagttctg actacccaag tttccttctc ttaaacagtt gatatgcata attgcatata
4021 ttcatggttc tgtgcaataa aaatggattc tcaccccatc ccaccttctg tgggatgttg
4081 ctaacgagtg cagattattc aataacagct cttgaacagt taatttgcac agttgcaatt
4141 gtccagagtc ctgtccatta gaaagggact ctgtatccta tttgcacgct acaatgtggg
4201 ctgatcaccc aaggactctt cttgtgcatt gatgttcata attgtatttg tccacgatct
4261 tgtgcactaa cccttccact cccttgtat tccagcaggg gaccttact actcaagacc
4321 tctgtactag gacagtttat gtgcacaatc ctaattgatt agaactgagt cttttatatc
4381 aaggtccctg catcatcttt gcttacatc aagagggtgc tggttaccta atgcccctcc
4441 tccagaaatt attgatgtgc aaaatgcaat ttccctatct gctgttagtc tggggtctca
4501 tcccctcata ttccttttgt cttacagcag ggggtacttg ggactgttaa tgcgcataat
4561 tgcaattatg gtcttttcca ttaaattaag atcccaactg ctcacaccct cttagcatta
4621 cagtagaggg tgctaatcac aaggacattt cttttgtact gttaatgtgc tacttgcatt
4681 tgtccctctt cctgtgcact aaagacccca ctcacttccc tagtgttcag cagtggatga
4741 cctctagtca agaccttgc actaggatag ttaatgtgaa ccatggcaac tgatcacaac
4801 aatgtctttc agatcagatc cattttatcc tccttgtttt acagcaaggg atattaatta
4861 cctatgttac ctttccctgg gactatgaat gtgcaaaatt ccaatgttca tggtctctcc
4921 ctttaaacct atattctacc ccttttacat tatagaaagg gatgctggaa acccagagtc
4981 cttctcttgg gactcttaat gtgtatttct aattatccat gactcttaat gtgcatattt
5041 tcaattgcct aattgatttc aattgtctaa gacatttcaa atgtctaatt gattagaact
5101 gagtctttta tatcaagcta atatctagct tttatatcaa gctaatatct tgacttctca
5161 gcatcataga aggggtact gattcctaa agtctttctt gaatttctat tatgcaaaat
5221 tgcctgagg ccgggtgtgg tggctcacac ctgtaatccc agcactttgg gaggctgagg
5281 tgggaagatc ccttactgcc aggagtttga gaccagcctg gccaacatta aaaaaaaaaa
5341 aaaaagtaag acaattgccc tggaatccca tccccctcac acctccttgg caaagcagca
5401 ggagtgctaa ctagctagtg ctctcttctct tatactgctt aaatgcgcat aattagcagt
5461 agttgatgtg ccctatgtt agagtagaat ccgcttcct tgctccattt gcattactgc
5521 aggagcttct aactagcctg aattcactct cttggactgt taatgtgcat acttatattt
5581 gctgctgtac ttttttacca tgtaaggacc ccaccactg tatttacatc ccagctggaa
5641 gtacctacta cttaagaccc ttagactagt aaagttagcg tgcataatct taggtgttat
5701 atacacattt tcagttgcat acagttgtgc cttttatcag gactcctgta cttatcaaag
5761 cagagagtgc taatcaatat taagccttc tcttcgaact gtagatggca tgtaattgca
5821 gttgtcaatg gtccttcaat tagacttggg tttctgacct atcacaccct ctttgcttta
5881 ttgcatgggg tactattcac ttaaggcccc tttctcaaac tgttaatgtg cctaatgaca
5941 attacatcag tatccttcct tttgaaggac agcatggttg gtgacactta aggcccatt
6001 tcttggcctc ccaatatgtg tgattgtatt tgtcgaggtt gctatgcact agagaaggaa
6061 agtgctcccc tcatcccacc tttttccttc cagcaggaag tgcccacccc ataagaccct
6121 tttatttgga gagtctaggt gcacaattgt aagtgaccac aagcatgcat cttggacatt
6181 tatgtgcgta atcgcacact gtcattcca tgtgaataag gtcctactct ccgaccccctt
6241 ttgcaataca gaagggttgc tgataacgca gtccccttttt cttggcatgt tgtgtgtgat
6301 tataatcgtc tgggatccta tgcactagaa aaggagggtc ctctccacat acctcagtct
6361 cacctttccc ttccagcagg gagtgcccac tccataagac tctcacattt ggacagtcaa
6421 ggtgcgtaat tgttaagtga acacaaccat gcaccttaga catggatttg cataactaca
6481 cacagctcaa cctatctgaa taaaatccta ctctcagacc ccttttgcag tacagcaggg
6541 gtgctgatca ccaaggccct tttcctggc ctggtatgcg tgtgattatg tttgtcccgg
```

FIG. 6B

```
6601 ttcctgtgta ttagacatgg aagcctccc tgccacactc cacccccaat cttcctttcc
6661 cttccggcag gagtgccctc tccataagac gcttacgttt ggacaatcaa ggtgcacagt
6721 tgtaagtgac cacaggcata caccttggac attaatgtgc ataaccactt tgcccattcc
6781 atctgaataa ggtcctactc tcagacccct tttgcagtac agcaggggtg ctgatcacca
6841 aggcccctt tcttggcctg ttatgtgcgt gattatattt gtctgggttc ctgtgtatta
6901 gacaaggaag ccttcccccc gccccaccc ccactcccag tcttcctttc ccttccagca
6961 gggagtgccc cctccataag atcattacat ttggacaatc aaggtgcaca attataagtg
7021 accacagcca tgcaccttgg acattattgg acattaatgt gcgtaactgc acatggccca
7081 tcccatctga ataaggacct actctcagat gcctttgcag tacagcaggg gtactgaatc
7141 accaaggccc ttttcttgg cctgttatgt gtgtgattat atttatccca gtttctgtgt
7201 aatagacatg aaagcctccc ctgccacacc ccacctccaa tcttcctttc ccttccacca
7261 gggagtgtcc actccatata cccttacatt tggacaatca aggtgcacaa ttgtaagtga
7321 gcataggcac tcaccttgga catgaatgtg cataactgca catggcccat cccatctgaa
7381 taaggtccta ctctcagacc ctttttgcag tacagcaggg gtgctgatca ccaaggcccc
7441 tttcctggc ctgttatgtg tgtgattata tttgttccag ttcctgtgta atagacatgg
7501 aagcctcccc tgccacactc cacccccaat cttcctttcc ttctgcagg aagtacccgc
7561 tccataagac ccttacattt ggacagtcaa ggtgcacaat tgtatgtgac cacaaccatg
7621 caccttggac ataaatgtgt gtaactgcac atggcccatc ccatctgaat aaggtcctac
7681 tctcagaccc cttttgcagt acagtaggtg tgctgataac caaggcccct cttcctggcc
7741 tgttaacgta tgtgattata tttgtctggg ttccagtgta taagacatgg aagcctcccc
7801 tgccccaccc cacccctcaat cttcctttcc cttctggcag ggagtgccag ctccataaga
7861 accttacatt tggacagtca aggtgcacaa ttctaagtga ccgcagccat gcaccttggt
7921 caataatgtg tgtaactgca cacggcctat ctcatctgaa taaggcctta ctctcagacc
7981 ccttttgcag tacagcaggg gtgctgataa ccaaggccca ttttctggc ctgttatgtg
8041 tgtgattata tttgtccagg tttctgtgta ctagacaagg aagcctcctc tgccccatcc
8101 catctacgca taatctttct tttcctccca gcagggagtg ctcactccat aagaccctta
8161 catttggaca atcaaggtgc acaattgtaa gtgaccacaa ccatgcatct tggaaattta
8221 tgtgcataac tgcacatggc ttatcctatt tgaataaagt cctactctca gaccccttt
8281 gcagtatagc tggggtgctg atcactgagg cctctttgct tggcttgtct atattcttgt
8341 gtactagata agggcacctt ctcatggact ccctttgctt ttcaacaagg agtacccact
8401 actttttaag attcttatat ttgtccaaag tacatggttt taattgacca caacaatgtc
8461 ccttggacat taatgtatgt aatcaccaca tggttcatcc taattaaaca aagttctacc
8521 ttctcaccct ccatttgcag tataccaggg ttgctgaccc cctaagtccc cttttcttgg
8581 cttgttgaca tgcataattg catttatgtt ggttcttgtg cctagacaa ggatgcccca
8641 cctcttttca atagtgggtg cccactcctt atgatcttta catttgaaca gttaatgtga
8701 ataattgcag ttgtccacaa ccctatcact tctaggacca ttatacctct tttgcattac
8761 tgtggggtat actgtttccc tccaggccc cttctggtgg actatcaaca tataattgaa
8821 attttcttt gtctttgtca gtagattaga gtcataccc atcacctttc ctttgtagta
8881 caacagggtg tcctgatcaa ccaaagtcct gttgttttgg actgttaata tgtgcaatta
8941 catttgctcc tgatctgtgc actagataag gatcctacct actttcttag tgttttttagc
9001 aggtagtgcc cactactcaa gactgtcact tggaatgttc atgtgcacaa actcaattct
9061 ctaagcatgt tcctgtacca cctttgcttt agagcagggg gatgatattc actaagtgcc
9121 ccttcttttg gactaatat gcattaatgc aattgtccac ctcttctttt agactaagag
9181 ttgatctcca catattcccc ttgcatcagg ggcatgttaa ttatgaatga acccttttct
9241 tttaatatta atgtcataat tgtatttgtg gacctgtgta ggagaaaaag acctatgtt
9301 cctcccatta cccttggat tgctgctgag aagtgttaac tactcataat ctcagctctt
9361 ggacaattaa tagcattaat aacaattatc aagggcactg atcattagat aagactcctg
9421 cttcctcgtt gctacatcg ggggtactga cccactaagg cccttgtac tgttaatgtg
9481 aatattgca attatatatg tctccttctg gtagagtggg atattatgc ctagtatccc
9541 ctttgcatta ctgcagggc tgctgactac tcaaaacttc tcctgggact gttaataggc
9601 acaatggcag ttatcaatgg ttttctccct cctgaccttt gttaagcaag cgccccaccc
9661 caccttagt ttccatggc ataataaagt ataagcattg gagtattcca tgcacttgtc
9721 tatcaaacag tggtccatac tcccaaccct tttgcattgc gccagtgtgt aaaatcacag
9781 gtagccatgg tgtcatgctt tatatacgaa gtcttccctc tctctgccc ttgtgtgccc
9841 ttggcccctt tttacagact attgctcaca atctcaggtg tccatatttg cagctattag
```

FIG. 6C

```
 9901 gtaagattgt gctgtctccc tcttcccttc cctctgccct gcccttttg cctctttgct
 9961 gggtaatgtt gaccagacaa ggcccttcct cttggactta aacaattctc agttgcactt
10021 tccttggtcc acccattata catgaaccca tctacttcct ttcgcattgc ttctgagtat
10081 gctgactacc caaagcccct tctgtgttat taataaacac agtactgatt gtccattt
10141 tcagcccatc agtccaagat ctccctacca ctttggtgtg ttggtgcagt gttgactatg
10201 aaaagcaggc ctgaactagg tggataagcc ttcactcatt ttctttcatt tattaatgat
10261 cctagtttca attattgtca gattctgggg acaagaacca ttcttgccca cctgtgttac
10321 tgctttactg tgcaaaatac tgaaggcaag tcagcccag ggagctggat tgccatcctt
10381 tatttgtgt ttccagtgta cactataaaa ttgtctccc aggaaggaag gttggcactt
10441 tctctgcatt cttctttcca gagcagattg cctggttaag aatctcttgt tgtcccttct
10501 gtatattgtt attgtaaagt gccaaatgcc aggatacagc cagaaaaatt gcttattatt
10561 attaaaaaaa tttttttaag aaagacatct ggattgtagg gtggactcga taacctggtc
10621 attattttt tgaagccaaa atatccattt atactatgta cctggtgacc agtgtctctc
10681 attttaactg agggtggtgg gtctgtggat agaacactga ctcttgctat tttaatatca
10741 aagatattct agagtggaac tcttaagacc agtatctttg tgtgggcttt accagcattc
10801 actttagaa aaactaccta aatttataa tcctttaatt tcttcatctg gagcacctgc
10861 ccctacttat ttcaagaaga ttgcagtaaa acgattaaat gaggaaacat atgcagaggt
10921 gcttttaaaa agcatatgcc acctttttta ttaattatta tataaaatga agcatttaat
10981 tatagtaata atttgaagta gtttgaagta ccacactgag gtgaggactt aaaaatgata
11041 agacgagttc cctatttat aagaaaaata agccaaaatt aaatattctt ttggatataa
11101 atttcaacag tgagatagct gcctagtgga aatgaataat atcccagcca ctagtgtaca
11161 gggtgtttg tggcacagga ttatgtaata tggaactgct caagcaaata actagtcatc
11221 acaacagcag ttctttgtaa taactgaaaa agaatattgt ttctcggaga aggatgtcaa
11281 aagatcggcc cagctcaggg agcagtttgc cctactagct cctcggacag ctgtaaagaa
11341 gagtctctgg ctctttagaa tactgatccc attgaagata ccacgctgca tgtgtcctta
11401 gtagtcatgt ctccttaggc tcctcttgga cattctgagc atgtgagacc tgaggactgc
11461 aaacagctat aagaggctcc aaattaatca tatctttccc tttgagaatc tggccaagct
11521 ccagctaatc tacttggatg ggttgccagc tatctggaga aaagatctt cctcagaaga
11581 ataggcttgc tgttttacag tgttagtgat ccattccctt tgacgatccc taggtggaga
11641 tggggcatga ggatcctcca ggggaaaagc tcactaccac tgggcaacaa ccctaggtca
11701 ggaggttctg tcaagatact ttcctggtcc cagatagga gataaagtct caaaaacaac
11761 caccacacgt caagctcttc attgttccta tctgccaaat cattatactt cctacaagca
11821 gtgcagagag ctgagtcttc agcaggtcca agaaatttga acacactgaa ggaagtcagc
11881 cttcccacct gaagatcaac atgcctggca ctctagcact tgaggatagc tgaatgaatg
11941 tgtatttctt tgtctcttc tttcttgtct ttgctctttg ttctctatct aaagtgtgtc
12001 ttacccattt ccatgtttct cttgctaatt tctttcgtgt gtgcctttgc ctcattttct
12061 cttttgttc acaagagtgg tctgtgtctt gtcttagaca tatctctcat ttttcatttt
12121 gttgctattt ctctttgctc tcctagatgt ggctcttctt tcacgcttta tttcatgtct
12181 ccttttggg tcacatgctg tgtgcttttt gtccttttct tgttctgtct acctctcctt
12241 tctctgccta cctctcttt tctctttgtga actgtgatta tttgttaccc cttccccttc
12301 tcgttcgttt taaatttcac ctttttttctg agtctggcct cctttctgct gtttctactt
12361 tttatctcac atttctcatt tctgcatttc ctttctgcct ctcttgggct attctctctc
12421 tcctccctg cgtgcctcag catctcttgc tgtttgtgat tttctattt agtattaatc
12481 tctgttggct tgtatttgtt ctctgcttct tccctttcta ctcacctttg agtatttcag
12541 cctcttcatg aatctatctc cctctctttg atttcatgta atctctcctt aaatatttct
12601 ttgcatatgt gggcaagtgt acgtgtgtgt gtgtcatgtg tggcagaggg gcttcctaac
12661 ccctgcctga taggtgcaga acgtcggcta tcagagcaag cattgtggag cggttcctta
12721 tgccaggctg ccatgtgaga tgatccaaga ccaaaacaag gcctagact gcagtaaaac
12781 ccagaactca agtagggcag aaggtggaag gctcatatgg atagaaggcc caagtataa
12841 gacagatggt ttgagacttg agacccgagg actaagatgg aaagcccatg ttccaagata
12901 gatagaagcc tcaggcctga aaccaacaaa agcctcaaga cagagaaaa cagaggggtgg
12961 cctgaattgg accgaaggcc tgagttggat ggaagtctca aggcttgagt tagaagtctt
13021 aagcctggg acaggacaca tggaaggcct aagaactgag acttgtgaca caaggccaac
13081 gacctaagat tagcccaggg ttgtagctgg aagacctaca acccaaggat ggaaggcccc
13141 tgtcacaaag cctacctaga tggatagagg acccaagcga aaaggtatc tcaagactaa
```

FIG. 6D

```
13201 cggccggaat ctggaggccc atgacccaga acccaggaag gatagaagct tgaagacctg
13261 gggaaatccc aagatgagaa ccctaaaccc tacctctttt ctattgttta cacttcttac
13321 tcttagatat ttccagttct cctgtttatc tttaagcctg attcttttga gatgtacttt
13381 ttgatgttgc cggttacctt tagattgaca gtattatgcc tgggccagtc ttgagccagc
13441 tttaaatcac agcttttacc tatttgttag gctatagtgt tttgtaaact tctgtttcta
13501 ttcacatctt ctccacttga gagagacacc aaaatccagt cagtatctaa tctggctttt
13561 gttaacttcc ctcaggagca gacattcata taggtgatac tgtatttcag tcctttcttt
13621 tgacccagaa agccctagac tgagaagata aatggtcag gttgttgggg aaaaaaaaag
13681 tgccaggctc tctagagaaa aatgtgaaga gatgctccag gccaatgaga agaattagac
13741 aagaaataca cagatgtgcc agacttctga gaagcacctg ccagcaacag cttccttctt
13801 tgagcttagg tgagcaggat tctgggggtt gggatttcta gtgatggtta tggaaagggt
13861 gactgtgcct gggacaaagc gaggtcccaa ggggacagcc tgaactccct gctcatagta
13921 gtggccaaat aatttggtgg actgtgccaa cgctactcct gggtttaata cccatctcta
13981 ggcttaaaga tgagagaacc tgggactgtt gagcatgttt aatactttcc ttgatttttt
14041 tcttcctgtt tatgtgggaa gttgatttaa atgactgata atgtgtatga aagcactgta
14101 aaacataaga gaaaaaccaa ttagtgtatt ggcaatcatg cagttaacat ttgaaagtgc
14161 agtgtaaatt gtgaagcatt atgtaaatca ggggtccaca gttttttctgt aaggggtcaa
14221 atcataaata ctttagactg tgggccatat ggtttctgtt acatatttgt tttttaaaca
14281 acgttttttat aaggtcaaaa tcattcttag ttttttgagcc aattggattt ggcctgctgt
14341 tcatagctta ccaccccctg atgtattatt tgttattcag agaaaatttc tgaatactac
14401 tagtttcctt ttctgtgcct gtccctgtgc taggcactaa aaatgcaatg attattgata
14461 tctaggtgac ctgaaaaaaa atagtgaatg tgctttgtaa actgtaaagc acttgtattc
14521 tactgtgata agcgttgtgg atacaaagaa aggagcaagc ataaaaagt gctctttcaa
14581 aaggatatag tactatgcag acacaaggaa ttgtttgata aatgaataaa ttatatgtat
14641 atttgaggcc aatttgtgtt tgctgctctg gtaattttga gtaaaaatgc agtattccag
14701 gtatcagaaa cgaaaacaca tggaaactgc ttttaaactt taaaatatac tgaaaacata
14761 agggactaag cttgttgtgg tcacctataa tgtgccagat accatgctgg gtgctagagc
14821 taccaaaggg ggaaaagtat tctcatagca acaaaaaatt tcagaaaggt gcatattaaa
14881 gtgctttgta aactaaagca tgatacaaat gtcaatgggc tacatattta tgaatgaatg
14941 aatggatgaa tgaatattaa gtgcctctta cataccagct attttgggta ctgtaaaata
15001 caagattaat tctcctatgt aataagagga aagttatcc tctatactat tcagatgtaa
15061 ggaatgatat attgcttaat tttaaacaat caagactttta ctggtgaggt taagttaaat
15121 tattactgat acatttttcc aggtaaccag gaaagagcta gtatgaggaa atgaagtaat
15181 agatgtgaga tccagaccga aagtcactta attcagcttg cgaatgtgct ttctaaatta
15241 taaagcactt gtaaatgaaa aatttgatgc tttctgtatg aataaaactt tctgtaagct
15301 aggtattgtc tctacaaaat tctcattgta tagttaaacc acagtgagaa gggttctata
15361 agtagttata caaaccaagg gtttaaatac ctgttaaata gatcaatttt gattgcctac
15421 tatgtgaact cactgttaaa ggcactgaaa atttatcata tttcatttag ccacagccaa
15481 aaataaggca ataccatgt tagcattttg tgaactctaa ggcaccatat aaatgtaact
15541 gttgattttc tcacttggtg ctgggtacta ggtttataaa attgtatgat agttattata
15601 ttgtgcaaat aaagtaggaa aatttgaata acaatgatta tcttttgaat acgcatacgc
15661 aagggattgg ttgtctgaag aatgccacta tagtagttat ctattgtgtg ccaatctcat
15721 tgctaggcat tggggatgca aagataaacc atctttattg tgtcttgggt agcagaagaa
15781 aatatgtgta aaatcaattt ataatttgta aactgccacc catatataag ctatatctgc
15841 tgaatgatca ttgattactc ttatccttag agataacaac tgggggcaca aacatttatt
15901 atcattattg aacctacaac agagatctat gtgtagattt acgaagccta cagttctata
15961 cagataggaa tgaactattg gcttactgaa tggtgattac tttctgtggg gctcggaact
16021 acatgcccta ggatataaaa atgatgttat cattatagag tgctcacaga aggaaatgaa
16081 gtaatatagg tgtgagatcc agaccaaaag ttatttaaca agtttattca gtgatgaaaa
16141 catgggacaa atggactata taaggcagtg tactaagctg agtagagaga taaagtcctg
16201 tccagaagat acatgctttc ctggcctgat tgaggagatg gaaaattttt gcaaaaaaca
16261 aggtgtttgt ggtcttccat ccagttctt aagtgctgat gataaaagtg aattagaccc
16321 accttgacct ggcctacaga agtaaaggag taaaaataaa tgcctcaggc gtgcttttg
16381 attcatttga taaacaaagc atctttatg tggaatatac cattctgggt cctgaggata
16441 agagagatga gggcattaga tcactgacag ctgaagatag a   (SEQ ID NO:1)
```

FIG. 6E

```
   1 cttcagttct taaagcgctg caattcgctg ctgcagccat atttcttact ctctcggggc
  61 tggaagcttc ctgactgaag atctctctgc acttggggtt cttttctagaa cattttctag
 121 tcccccaaca cccttttatgg cgtatttctt taaaaaaatc acctaaattc cataaaatat
 181 ttttttaaat tctatacttt ctcctagtgt cttcttgaca cgtcctccat atttttttaa
 241 agaaagtatt tggaatattt tgaggcaatt tttaatattt aaggaatttt tctttggaat
 301 cattttggt tgacatctct gtttttgtg gatcagtttt ttactcttcc actctctttt
 361 ctatattttg cccatcgggg ctgcggatac ctggttttat tattttttct ttgcccaacg
 421 gggccgtgga tacctgcctt taattctttt tttattcgcc catcgggcc gcggatacct
 481 gcttttatt ttttttttcct tagcccatcg gggtatcgga tacctgctga ttcccttccc
 541 ctctgaaccc ccaacactct ggccatcgg ggtgacggat atctgctttt taaaaatttt
 601 cttttttttgg cccatcgggg cttcggatac ctgcttttttt ttttttatt tttccttgcc
 661 catcggggcc tcggatacct gctttaattt ttgtttttct ggcccatcgg ggccgcggat
 721 acctgctttg atttttttt ttcatcgccc atcggtgctt tttatggatg aaaaaatgtt
 781 ggttttgtgg gttgttgcac tctctggaat atctacactt tttttttgctg ctgatcattt
 841 ggtggtgtgt gagtgtacct accgctttgg cagagaatga ctctgcagtt aagctaaggg
 901 cgtgttcaga ttgtggagga aaagtggccg ccatttttaga cttgccgcat aactcggctt
 961 agggctagtc gtttgtgcta agttaaacta gggaggcaag atggatgata gcaggtcagg
1021 cagaggaagt catgtgcatt gcatgagcta aacctatctg aatgaattga tttggggctt
1081 gttaggagct ttgcgtgatt gttgtatcgg gaggcagtaa gaatcatctt ttatcagtac
1141 aagggactag ttaaaaatgg aaggttagga aagactaagg tgcagggctt aaaatggcga
1201 ttttgacatt gcggcattgc tcagcatggc gggctgtgct ttgttaggtt gtccaaaatg
1261 gcggatccag ttctgtcgca gtgttcaagt ggcgggaagg ccacatcatg atgggcgagg
1321 cttttgttaag tggttagcat ggtggtggac atgtgcggtc acacaggaaa agatggcggc
1381 tgaaggtctt gccgcagtgt aaaacatggc gggcctcttc gtcttgctg tgtgctttc
1441 gtgttgggtt ttgccgcagg gacaatatgg caggcgttgt catatgtata tcatggcttt
1501 tgtcacgtgg acatcatggc gggcttgccg cattgttaaa gatggcgggt tttgccgcct
1561 agtgccacgc agagcgggag aaaagtgggg atggacagtg ctggattgct gcataaccca
1621 accaattaga aatgggggtg gaattgatca cagccaatta gagcagaaga tggaattaga
1681 ctgatgacac actgtccagc tactcagcga agacctgggt gaattagcat ggcacttcgc
1741 agctgtcttt agccagtcag gagaaagaag tggaggggcc acgtgtatgt ctcccagtgg
1801 gcggtacacc aggtgttttc aaggtctttt caaggacatt tagcctttcc acctctgtcc
1861 cctcttattt gtcccctcct gtccagtgct gcctcttgca gtgctggata tctggctgtg
1921 tggtctgaac ctccctccat tcctctgtat tggtgcctca cctaaggcta agtatacctc
1981 ccccccccacc cccaaccccc cccaactccc caccccccacc ccccaccccc cacctcccca
2041 cccccccaaca cccctaccccc cctaccccc tctggtctgc cctgcactgc actgttgcca
2101 tgggcagtgc tccaggcctg cttggtgtgg acatggtggt gagccgtggc aaggaccaga
2161 atggatcaca gatgatcgtt ggccaacagg tgcagaaga ggaattcctg ccttcctcaa
2221 gaggaacacc tacccccttgg ctaatgctgg ggtcggattt tgatttatat ttatcttttg
2281 gatgtcagtc atacagtctg attttgtggt ttgctagtgt ttgaatttaa gtcttaagtg
2341 actattatag aaatgtatta agaggcttta tttgtagaat tcactttaat tacatttaat
2401 gagtttttgt tttgagttcc ttaaaattcc ttaaagtttt tagcttctca ttacaaattc
2461 cttaacctttt ttttggcagt agatagtcaa agtcaaatca tttctaatgt tttaaaaatg
2521 tgctggtcat tttctttgaa attgacttaa ctatttttcct ttgaagagtc tgtagcacag
2581 aaacagtaaa aaatttaact tcatgaccta atgtaaaaaa gagtgtttga aggtttacac
2641 aggtccaggc cttgctttgt tcccatcctt gatgctgcac taattgacta atcacctact
2701 tatcagacag gaaacttgaa ttgctgtggt ctggtgtcct ctattcagac ttattatatt
2761 ggagtatttc aattttttcgt tgtatcctgc ctgcctagca tccagttcct ccccagccct
2821 gctcccagca aaccctagt ctagccccag ccctactccc accccgcccc agccctgccc
2881 cagccccagt ccctaacccc cccagcccta gcccagtcc cagtcctagt tcctcagtcc
2941 cgcccagctt ctctcgaaag tcactctaat tttcattgat tcagtgctca aaataagttg
3001 tccattgctt atcctattat actgggatat tccgtttacc cttggcattg ctgatcttca
3061 gtactgactc cttgaccatt tcagttaat gcatacaatc ccatttgtct gtgatctcag
3121 gacaaagaat ttccttactc ggtacgttga agttagggaa tgtcaattga gagctttcta
3181 tcagagcatt attgcccaca atttgagtta cttatcattt tctcgatccc ctgcccttaa
3241 aggagaaacc atttctctgt cattgcttct gtagtcacag tcccaatttt gagtagtgat
```

FIG. 7A

```
3301 cttttcttgt gtactgtgtt ggccacctaa aactctttgc attgagtaaa attctaattg
3361 ccaataatcc tacccattgg attagacagc actctgaacc ccatttgcat tcagcagggg
3421 gtcgcagaca accogtcttt tgttggacag ttaaaatgct cagtcccaat tgtcatagct
3481 ttgcctatta aacaaaggca ccctactgcg cttttgctg tgcttctgga gaatcctgct
3541 gttcttggac aattaaagaa caaagtagta attgctaatt gtctcaccca ttaatcatga
3601 agactaccag tcgcccttgc atttgccttg aggcagcgct gactacctga gatttaagag
3661 tttcttaaat tattgagtaa aatcccaatt atccatagtt ctgttagtta cactatggcc
3721 tttgcaaaca tctttgcata acagcagtgg gactgactca ttcttagagc ccttccctt
3781 ggaatattaa tggatacaat agtaattatt catggttctg cgtaacagag aagaccact
3841 tatgtgtatg cctttatcat tgctcctaga tagtgtgaac tacctaccac cttgcattaa
3901 tatgtaaaac actaattgcc catagtccca ctcattagtc taggatgtcc tctttgccat
3961 tgctgctgag ttctgactac ccaagtttcc ttctcttaaa cagttgatat gcataattgc
4021 atatattcat ggttctgtgc aataaaaatg gattctcacc ccatcccacc ttctgtggga
4081 tgttgctaac gagtgcagat tattcaataa cagctcttga acagttaatt tgcacagttg
4141 caattgtcca gagtcctgtc cattagaaag ggactctgta tctatttgc acgctacaat
4201 gtgggctgat cacccaagga ctcttcttgt gcattgatgt tcataattgt atttgtccac
4261 gatcttgtgc actaacccttt ccactccctt tgtattccag caggggaccc ttactactca
4321 agacctctat actaggacag tttatgtgca caatcctaat tgattagaac tgagtctttt
4381 atatcaaggt ccctgcatca tctttgcttt acatcaagag ggtgctggtt acctaatgcc
4441 cctcctccag aaattattga tgtgcaaaat gcaatttccc tatctgctgt tagtctgggg
4501 tctcatcccc tcatattcct tttgtcttac agcagggggt acttgggact gttaatgcgc
4561 ataattgcaa ttatggtctt ttccattaaa ttaagatccc aactgctcac accctcttag
4621 cattacagta gagggtgcta atcacaagga catttctttt gtactgttaa tgtgctactt
4681 gcatttgtcc ctcttcctgt gcactaaaga ccccactcac ttccctagtg ttcagcagtg
4741 gatgacctct agtcaagacc tttgcactag gatagttaat gtgaaccatg gcaactgatc
4801 acaacaatgt ctttcagatc agatccattt tatcctcctt gttttacagc aagggatatt
4861 aattacctat gttacctttc cctgggacta tgaatgtgca aaattccaat gttcatggtc
4921 tctccctta aacctatatt ctacccttt tacattatag aaagggatgc tggaaaccca
4981 gagtccttct cttgggactc ttaatgtgta tttctaatta tccatgactc ttaatgtgca
5041 tattttcaat tgcctaattg atttcaattg tctaagacat ttcaaatgtc taattgatta
5101 gaactgagtc ttttatatca agctaatatc tagctttat atcaagctaa tatcttgact
5161 tctcagcatc atagaagggg gtactgattt cctaaagtct ttcttgaatt tctattatgc
5221 aaaattgccc tgaggccggg tgtggtggct cacacctgta atcccagcac tttgggaggc
5281 tgaggtggga agatcccta ctgccaggag tttgagacca gctggccaa cattaaaaaa
5341 aaaaaaagt aagacaattg ccctggaatc ccatcccct cacacctcct tggcaaagca
5401 gcaggagtgc taactagcta gtgcttcttc tcttatactg cttaaatgcg cataattagc
5461 agtagttgat gtgcccctat gttagagtag aatccgcttt ccttgctcca tttgcattac
5521 tgcaggagct tctaactagc ctgaattcac tctcttggac tgttaatgtg catacttata
5581 tttgctgctg tacttttta ccatgtaagg accccaccca ctgtatttac atcccagctg
5641 gaagtaccta ctacttaaga ccctttagact agtaaagtta gcgtgcataa tcttaggtgt
5701 tatatacaca ttttcagttg catacagttg tgccttttat caggactcct gtacttatca
5761 aagcagagag tgctaatcaa tattaagccc ttctcttcga actgtagatg gcatgtaatt
5821 gcagttgtca atggtccttc aattagactt gggtttctga cctatcacac cctctttgct
5881 ttattgcatg gggtactatt cacttaaggc ccctttctca aactgttaat gtgcctaatg
5941 acaattacat cagtatcctt ccttttgaag gacagcatgg ttggtgacac ctaaggcccc
6001 atttcttggc ctcccaatat gtgtgattgt atttgtcgag gttgctatgc actagagaag
6061 gaaagtgctc ccctcatccc cactttccc ttccagcagg aagtgcccac cccataagac
6121 cctttattt ggagagtcta ggtgcacaat tgtaagtgac cacaagcatg catcttggac
6181 atttatgtgc gtaatcgcac actgctcatt ccatgtgaat aaggtcctac tctccgaccc
6241 cttttgcaat acagaagggt tgctgataac gcagtccct tttcttggca tgttgtgtgt
6301 gattataatc gtctgggatc ctatgcacta gaaaggagg gtcctctcca catacctcag
6361 tctcaccttt ccttccagc agggagtgcc cactccataa gactctcaca tttggacagt
6421 caaggtgcgt aattgttaag tgaacacaac catgcacctt agacatggat ttgcataact
6481 acacacagct caacctatct gaataaaatc ctactctcag acccctttg cagtacagca
6541 ggggtgctga tcaccaaggc ccttttcct ggcctggtat gcgtgtgatt atgtttgtcc
```

FIG. 7B

```
6601 cggttcctgt gtattagaca tggaagcctc cctgccaca ctccaccccc aatcttcctt
6661 tcccttccgg cagggagtgc cctctccata agacgcttac gtttggacaa tcaaggtgca
6721 cagttgtaag tgaccacagg catacacctt ggacattaat gtgcataacc actttgccca
6781 ttccatctga ataaggtcct actctcagac cccttttgca gtacagcagg ggtgctgatc
6841 accaaggccc cttttcttgg cctgttatgt gcgtgattat atttgtctgg gttcctgtgt
6901 attagacaag gaagccttcc cccgccccc accccactc ccagtcttcc tttcccttcc
6961 agcagggagt gcccctcca taagatcatt acatttggac aatcaaggtg cacaattata
7021 agtgaccaca gccatgcacc ttggacatta ttggacatta atgtgcgtaa ctgcacatgg
7081 cccatcccat ctgaataagg tcctactctc agatgccctt gcagtacag cagggtact
7141 gaatcaccaa ggcccttttt cttggcctgt tatgtgtgtg attatattta tcccagtttc
7201 tgtgtaatag acatgaaagc ctccctgcc acacccacc tccaatcttc ctttcccttc
7261 caccaggag tgtccactcc atatacccctt acatttggac aatcaaggtg cacaattgta
7321 agtgagcata ggcactcacc ttggacatga atgtgcataa ctgcacatgg cccatcccat
7381 ctgaataagg tcctactctc agacccttt tgcagtacag cagggtgct gatcaccaag
7441 gccccttttc ctggcctgtt atgtgtgtga ttatattgt tccagttcct gtgtaataga
7501 catggaagcc tccctgcca cactccacc ccaatcttcc tttccttct ggcaggaagt
7561 acccgctcca taagacccctt acatttggac agtcaaggtg cacaattgta tgtgaccaca
7621 accatgcacc ttggacataa atgtgtgtaa ctgcacatgg cccatcccat ctgaataagg
7681 tcctactctc agacccctt tgcagtacag taggtgtgct gataaccaag gcccctcttc
7741 ctggcctgtt aacgtatgtg attatatttg tctgggttcc agtgtataag acatggaagc
7801 ctccctgcc ccaccccacc ctcaatcttc ctttccctt tggcagggag tgccagctcc
7861 ataagaacct tacatttgga cagtcaaggt gcacaattct aagtgaccgc agccatgcac
7921 cttggtcaat aatgtgtgta actgcacacg gcctatctca tctgaataag gccttactct
7981 cagacccctt ttgcagtaca gcagggtgc tgataaccaa ggcccatttt cctggcctgt
8041 tatgtgtgtg attatatttg tccaggtttc tgtgtactag acaaggaagc ctcctctgcc
8101 ccatcccatc tacgcataat ctttcttttc ctcccagcag ggagtgctca ctccataaga
8161 cccttacatt tggacaatca aggtgcacaa ttgtaagtga ccacaaccat gcatcttgga
8221 aatttatgtg cataactgca catggcttat cctatttgaa taagtcccta ctctcagacc
8281 cccttgcag tatagctggg gtgctgatca ctgaggcctc tttgcttggc ttgtctatat
8341 tcttgtgtac tagataaggg caccttctca tggactccct ttgcttttca acaaggagta
8401 cccactactt tttaagattc ttatatttgt ccaaagtaca tggttttaat tgaccacaac
8461 aatgtccctt ggacattaat gtatgtaatc accacatggt tcatcctaat taaacaaagt
8521 tctaccttct caccctccat ttgcagtata ccaggggttgc tgaccccta agtcccctt
8581 tcttggcttg ttgacatgca taattgcatt tatgttggtt cttgtgccct agacaaggat
8641 gccccacctc ttttcaatag tgggtgccca ctccttatga tctttacatt tgaacagtta
8701 atgtgaataa ttgcagttgt ccacaacct atcacttcta ggaccattat acctcttttg
8761 cattactgtg gggtatactg tttccctca aggccccttc tggtggacta tcaacatata
8821 attgaaattt tcttttgtct ttgtcagtag attaaggtca tacccccatca cctttcctt
8881 gtagtacaac agggtgtcct gatcaaccaa agtcctgttg ttttggactg ttaatatgtg
8941 caattacatt tgctcctgat ctgtgcacta gataaggatc ctacctactt tcttagtgtt
9001 tttagcaggt agtgcccact actcaagact gtcacttgga atgttcatgt gcacaaactc
9061 aattctctaa gcatgttcct gtaccaccctt tgctttagag caggggatg atattcacta
9121 agtgcccctt cttttggact taatatgcat taatgcaatt gtccacctct tctttagac
9181 taagagttga tctccacata ttccccttgc atcaggggca tgttaattat gaatgaaccc
9241 ttttctttta atattaatgt cataattgta tttgtggacc tgtgtaggag aaaaagaccc
9301 tatgttcctc ccattacct ttggattgct gctgagaagt gttaactact cataatctca
9361 gctcttggac aattaatagc attaataaca attacaaggcaactgatca ttagataaga
9421 ctcctgctc ctcgttgctt acatcggggg tactgaccca ctaaggcccc ttgtactgtt
9481 aatgtgaata tttgcaatta tatatgtctc cttctggtag agtgggatat tatgccctag
9541 tatcccctttt gcattactgc agggctgct gactactcaa aacttctcct gggactgtta
9601 ataggcacaa tggcagttat caatggtttt ctccctccct gaccttgtta agcaagcgcc
9661 ccacccacc cttagttcc catggcataa taaagtataa gcattggagt attccatgca
9721 cttgtctatc aaacagtggt ccatactccc aaccctttg cattcgccca gtgtgtaaaa
9781 tcacaggtag ccatggtgtc atgcttata tacgaagtct tccctctctc tgccccttgt
9841 gtgcccttgg ccccttttta cagactattg ctcacaatct caggtgtcca tatttgcagc
```

FIG. 7C

```
 9901 tattaggtaa gattgtgctg tctccctctt cccttccctc tgccctgccc cttttgcctc
 9961 tttgctgggt aatgttgacc agacaaggcc ctttctcttg gacttaaaca attctcagtt
10021 gcactttcct tggtcccacc cattatacat gaacccctct acttccttc gcattgcttc
10081 tgagtatgct gactacccaa agcccttct gtgttattaa taaacacagt actgattgtc
10141 ccatttttca gcccatcagt ccaagatctc cctaccactt tggtgtgttg gtgcagtgtt
10201 gactatgaaa agcaggcctg aactaggtgg ataagccttc actcattttc tttcatttat
10261 taatgatcct agtttcaatt attgtcagat tctggggaca agaaccattc ttgcccacct
10321 gtgttactgc tttactgtgc aaaatactga aggcaagtca gacccaggga gctggattgc
10381 catcctttat tttgtgtttc cagtgtacac tataaaattg tctccccagg aaggaaggtt
10441 ggcactttct ctgcattctt cttccagag cagattgcct ggttaagaat ctcttgttgt
10501 cccctttgta tattgttatt gtaaagtgcc aaatgccagg atacagccag aaaaattgct
10561 tattattatt aaaaaaattt ttttaagaaa gacatctgga ttgtagggtg gactcgataa
10621 cctggtcatt attttttga agccaaaata tccatttata ctatgtacct ggtgaccagt
10681 gtctctcatt ttaactgagg gtggtgggtc tgtggataga acactgactc ttgctatttt
10741 aatatcaaag atattctaga gtggaactct taagaccagt atctttgtgt gggcttacc
10801 agcattcact tttagaaaaa ctacctaaat tttataatcc tttaattct tcatctggag
10861 cacctgcccc tacttatttc aagaagattg cagtaaaacg attaaatgag ggaacatatg
10921 cagaggtgct tttaaaaagc atatgccacc tttttatta attattatat aaaatgaagc
10981 atttaattat agtaataatt tgaagtagtt tgaagtacca cactgaggtg aggacttaaa
11041 aatgataaga cgagttccct attttataag aaaaataagc caaaattaaa tattctttg
11101 gatataaatt tcaacagtga gatagctgcc tagtggaaat gaataatatc ccagccacta
11161 gtgtacaggg tgttttgtgg cacaggatta tgtaatatgg aactgctcaa gcaaataact
11221 agtcatcaca acagcagttc tttgtaataa ctgaaaaga atattgtttc tcggagaagg
11281 atgtcaaaag atcggcccag ctcagggagc agtttgccct actagctcct cggacagctg
11341 taaagaagag tctctggctc tttagaatac tgtaagtact acttcgtagc tattaagtaa
11401 tcttttcct attctatttt ctttctctta gatgccacct atagaaaagt cagagggtcc
11461 agtaagttc tttccttctt cccacctcat ctgcaatata tatatataga gagagaaata
11521 gatacataca tacatgcata aatacacata tgtgagttaa ccagcagaac tgtagaatta
11581 atattgtgga cccagctcta tgctaggtta cactgataac ctgggtagga atgatatcat
11641 cctatataat ttcattcctg agatgatttt atcgttgagg agctaatgtg agcacatttg
11701 aaataacttt agaaaataat aagtgctgtt ttgtgtgaat cataagtagt agttttagga
11761 agggaaccca caaggatttg aagttgatag aataaactta aggaagtggg tttgcttttt
11821 ctcttaagc caagatagga ttaatattgc agccatctgg atagtccagt tggtttattt
11881 taatttcatt tgttttttac ctctttggaa gccatggaaa gagatgaaag ggatagagca
11941 tagccattgt gtttggctat ttgcgaaggt tggcaaatta gtgattgcta aatctcataa
12001 gcttgagtat tttaaagttc agagattgag ggcataaatc taatacttcg gctccttcca
12061 caatttact acatttctgc ccaagaacag atgaccatgg ataatgcata tcgtagatac
12121 tttttaagtt tggaaccttt ttgccaagag ggtagtggag aagtgaagtc aaaaccttga
12181 ccttccttgc ctactttatg ctgtagttta tatccttct ttcctcccac ctttcgtaaa
12241 gctaaaagaa gcttagcctc cttaatgttt tccagctgac aaaatattgt ttaacataac
12301 attcgaaact ttttttctgg tgcacattca tgcatcacag caggagcaac aagaaccata
12361 taagtgaact ggcttccactt atagcccgtt ttaattcata tccatatttc ctcagggctt
12421 gtttccatgc ctcccagccc cactccatat gcttaacaac attgtctgc tgactgaggg
12481 ttatatacat catggtcttg aaccttcttg gaaacatggt ctgtgccatt gtttctcaaa
12541 cccaagtaat gcttcatgat gaaacacctt ctaaggaac aaaattttct gagatcctaa
12601 aaaaatgtgt tttgaggaac actgacttaa caaagatatt tgaaatgtaa atatgttttc
12661 caatttcacg ttgtctttgt caaagatgtg ttttatataa cttatgtaga acttggggat
12721 ccattagaat atattcacaa atcccagggg ttatcacccc aatttgagaa accctggtct
12781 atgcttatga aatcttctat tggtaattaa attgtcattc attgtcaaca tacaattata
12841 attattattg gaattgtttt taaatgaatg aatttggagg tgattctgta ccttaagtca
12901 agaggaagga tggctgatt ttaggtggat tgattatact agatagcatc caaaggtgaa
12961 tcttgaagct gtatttaaat tcattgcttg aaataatttc caccttaag aaaaatctct
13021 agcaattgta aaaagggatg ctctggaaat gtgggcatct tcaaaataga gataattctt
13081 gtgttagttc aacaaatatt attgtaccag gtgctggaat aaatagcaaa accaaagaca
13141 ggatttatat caaggaattt gctttcttat ggaggatgca gaaggaaatc attatggttt
```

FIG. 7D

```
13201 tgggcagaaa tgcttagact ttagtcctgg ctctgagttt ggttcagatc accatcaatc
13261 tgaccatctc gagactgcta gtgaaataag ataggggctt atatcaaata cctaaatccc
13321 tgaaaatgac attttgtgat ttggaaaatt ttcaaagtc taatgaagga aacttttttg
13381 gcatttcttt aaatgattat tgtcatttct tttctgactt ttccctttat aaaaccttaa
13441 catgtaggat tggaggaagt tttctgacca ttttctcata tcctctttca gctttatctt
13501 tctgtaactt ccatttctct agccacctcc ctaaattaca gaagactgtg agacccaggg
13561 ctgctgtgat taggcattca taatttcttt tcagggtgtt tgtgcctga ttatcaaatg
13621 tacagcttga agggagttca tgtcttaaag taatgaatta agagttgacc tttgttgact
13681 gctaaaatat tcttatatgt gaaagcatcc tggaaaaata cgttaccagc ttaaagagaa
13741 agaaactaat gattatatct gaactgagct aatgcctctt ctcttccccc aaaccttatc
13801 agtttggatg gcaaagagta atgatgtgtc agttaaacag agctaatgcc ttcctctgcc
13861 ttgtcttaaa gactggattg ggagaaaatt gatattctca ctaccatatt ttgggctgta
13921 ggcaagtagc attttacaca ggtttccttc aaaaatccaa ctcaagttgg agctcatgta
13981 tttaagacat agctggcctg ctgaatttaa caagttaaac ttcagtggcc atgtacagtt
14041 atatatcact atatatatgt gtattaggct gtcgagttgg tcatgttttt gttggtgact
14101 taggctttac ttgatagctc ttccttgacc tttccaaatt gagtactgat acatggagct
14161 tgggcttctt ctgcatctta tacaaatgag tttggtaaag aagcctctcc tttactgttt
14221 tgatgtttat attagaaata acttttgatt attttttttc atgttaggat gagaaactga
14281 aacaaaatgt aaatttgacc ggtgctagac ttcttaaatt atgggtagac ttaaagtatt
14341 attttcctta accaattaga atgctagtct tctagtgttc ccggaaacat gagaggttat
14401 gcagtagacc caagcaatac cctcttatta cataatcaag tgcgtataag aatttaaaaa
14461 tagggatatg actggaacat cactgtactt taccaggtcc cattataaaa ttatctatgt
14521 tactttacca atagctttga aaactgatgg catagtatat tttatagtat gctgttagtg
14581 tgattggcat tgaacagtga tgggatataa tcactctaca atctatatgt tattaaagtt
14641 ttccagcctt atagatctcc cttgactgaa aattagctac taacttacga cttattttt
14701 acagcagatt gactaggtct ttccaggaaa tctgttgatg tacaaaaaca aagtttaatt
14761 gctaatgttt ttttaaaaaa taacttttg atattacgga tacctggtta tttgggcctt
14821 gtatatttta acatcaaaat taccctatat aaatccatat aaacagaaaa gaagagagt
14881 aagtctttag atcagatctg caaacaatga tggtacgtac tgtagaaaaa tctggaacat
14941 agacttacca gttcttaggt tccatttgc ttgctttta aaaactgtgt cttataagtc
15001 ttcagcaact ggttgggaga ttttagaaa aaataacctt ttaatgttag aacagtgtag
15061 agatttacag aatgattctg aagatagagt ttctgtgtac ttcacaccca gttttttccca
15121 gtgttaacat tttacattag tttggtacat ttgtcacaac aaaccaatat tgatacatta
15181 ttattaacta gagtccatat tttattcaga tttccttagt ttttccttaa tgttcttttt
15241 gtgttccagg atcccattga agataccacg ctgcatgtgt ccttagtagt catgtctcct
15301 taggctcctc ttggtaatga cagtttctca gactctttgt ttttgatgaa cttcacagtt
15361 ttgaggacta atggtccagt attctataga atgtctctct attggaattt gtctgatgtt
15421 cttctcatga ctagattggg tttatgagtg tttaggagga agaccacaaa ggtagagtgc
15481 cattcttatc acttatcaag agtacatact atcaacatga cttatcactg tttatgttat
15541 ccttaatcac ctgtctgagg tactatttgt caggtttctc cagcgtaaaa ttagtctttta
15601 tttctccatt tccctactat actgttcaca taggaagtca ctatgtgcag ccagcactta
15661 aggaatggga aattaccttc cacctcattg agggcagagt attacataa attatttgga
15721 attcttttgc acaggatgtc ttttctccac aatgtattgt gtttattcag tcatttatat
15781 cagtatgatc tcagggatat tttatactct gggttataat acagtattac ttattctgt
15841 tgttcaaatt gttccagctt tggccattgg gaggtctttc atttggcttt gatataaccc
15901 catgaatgtg ggtttttttgt ttgagcactt tcttattttt ggaactacaa catgcttcag
15961 actcatttgc atatctcctg cctggaccta aaatgatgta tttctgcaag gagccttgat
16021 acttttttatt ggagagtaat attagaaatc aagaagtgaa tgctaggtgc gctcattact
16081 actggagtgt cattccttca agacctttc agttgacaag agcaaggaga tatatatttg
16141 cattctaacg tgtctatatg cacatagcta taaatatata taaccatctg tatctatatt
16201 aaactaaatg tgtttatacc tacgtctcca actctaatca ttgccacatg gatcattata
16261 gtctcaccc ctgcttatc tgttacctcc catttctaca gtgagaaacc tggcttggtt
16321 gggaaatttt tctgttaata ttacggtagt gagtgtttga catttgcttc tatggttaag
16381 tttaggagaa gtttagctgt agggtattct tgaaactaga aatgaccctt ctgccctaaa
16441 tgtttctgcc agttttgaaa cgtaaaatag gttgcagaaa caaactttat cttaagaacc
```

FIG. 7E

```
16501  agaatttact  tcaatccaca  ttttgacatt  gattttcaga  ttaaattatt  ctgatatcgc
16561  caggtaagct  gttccttggg  tatgcatttc  ttctttccgt  ttttttctaa  gagctaaagg
16621  accctgagaa  cactggaggt  gggaaaggaa  gggaaaggca  tgttcacacg  tgggatagga
16681  aaggttcatt  tactgacctc  cagctagcct  tccaaagtgc  ctattaaga  cccaaggagt
16741  agatgtcttc  cttggcaatt  gtaacccaaa  tataattttt  aacctttcaa  ttttagtcaa
16801  gaaagttggt  gtgctgttac  aaaaagtgcc  ctgattaaca  gcattgtcat  gtgcattgca
16861  tattaatcag  caatttaaaa  taacatgaaa  ttatgttgag  tataatttta  atatttttata
16921  ttagatatta  gtttgagaca  gtgtttctca  agtctgtata  ataagtttga  tagtagggag
16981  gttttctctc  aagaaaagaa  ttattcagtg  tgcacctaca  taatcactgc  ttagattcta
17041  caattaatat  tttgctatat  ttgattaaac  gttttctgta  aagaaaaat   attattatgt
17101  actatttagg  tttatgggaa  taattgttaa  gttaaagtgt  atgaacaaac  ctggaatgaa
17161  atctgtttgc  ctacatctat  aatacaacta  taaaacatag  cagatgtaca  aattagtagt
17221  taatagataa  ctaaaatgca  aatatggcac  tactattata  gtattatagt  ttcttttgag
17281  tggcgtgtct  gtaatatcac  atgctgtgtt  gatgcacttc  accaaactgc  tgttttcaaa
17341  ctgctttaaa  tcctgccatt  atagcacata  gcaatgctat  ttcactttca  tttggcacaa
17401  aacacattta  tatattgttt  gcttctcttc  tttctgtaa   tccccaggca  acaaaactag
17461  aacatttgcc  actaatctgg  caacgtggtc  ctatattatg  aagtagtcat  atagctgatc
17521  taaactatcc  ttacagtgaa  atgagagtat  tgtgaaagtt  ttgtagaaag  ctccccatat
17581  gtcctgagaa  tctatgcaca  gaccccacag  ttaaaagacc  tttgaattgt  gggaagacat
17641  gggtttaagt  atcacttggt  taccttctat  ttgtgtaaca  ttgaggtagt  ttcatcttct
17701  gggttcccag  tttccttaga  gaatgaaaat  gttgaattat  gtgattttt   ttttttttttg
17761  agacggagtt  ttgctctttc  gcccaggctg  gagtgaagta  gcacgatctc  gactcactgc
17821  aacctcctc   ccccatgatc  aagcaattct  cctgcctcag  cctcccaagt  agctgggatt
17881  acaggcaccc  gccccccacc  cccgccccc   agctaatgtt  tgtattttta  gtacagatgg
17941  agtttcgcg   tgttggccag  gctggtctcg  aactctgtga  ctcaggtgat  ccactcgcct
18001  tggcctccca  aagtgctagg  attacaggca  tgagccactg  cgcctggcct  atgtgattat
18061  taatatcacg  tctagctgtg  acaattctgt  ctgatgctgg  agtatttgaa  ccagatggct
18121  ggctgtgcca  ctcagttatt  ctctccataa  gactttgata  ttttgttggt  ctgcaagatg
18181  acggattctc  aaaattcttg  tcagtgaata  ttgaacccta  gtgaaatgta  tggttctgta
18241  tcagttccaa  aatgtaacca  ctttctctag  ccttagatcc  ccagttccaa  aatgtaacca
18301  ttttctctag  ccttagattc  ccgttaaggg  aaagggaatg  ctctttgagt  atgtcatcac
18361  catagtaaca  ggcaaaacta  gagggctttg  atgctaaagc  aagatactcc  ataaatatgc
18421  ttaagaagac  ttggggagac  tggaatagtt  gttccctttt  agatgccagt  gtataaatga
18481  atttgagcta  ggatccgttt  atttaaaatt  tctttaggtg  tatttgcttg  catatggagt
18541  gcacatttac  tctcattaat  ggagttttag  gaagcagtag  agtaaatgca  taaacatgta
18601  tgaaccgcca  tgtttaactg  gaagcctgca  tttggaagtc  aagtatctaa  tcttagatta
18661  aattaggatg  gggaaggatg  ttggcaagag  atttgaagc   ttgttctgct  tatattgaga
18721  acatcataga  acagtttggc  cttttttaaag ctagagaata  gtgttgaata  agtgatgttc
18781  catatattcc  tgtttgacat  tgacataaag  gtttcctcat  gatacagtaa  tccctgatca
18841  gggatctgga  agcctgtatt  catttaaggt  actcaggttt  aacatactgg  gtgcttttca
18901  caccatacta  tacagtacca  tgcaaagtgc  tttcaagact  gcaaatttgg  cttagatccc
18961  cttagtgag   ctcctatgct  atagtaaagg  tagatagcca  attattaaaa  acagtcaaga
19021  caattgcacc  tctaagcagt  agtagcagtt  gccacaccac  cttgaatctt  gaagtatttt
19081  cagcaacagg  atgaccatta  gccacaaatt  tagtgtcagc  ccttaaggtc  ggtattggtt
19141  tgacccatat  tttcatgtag  ttcttttttct tcacttgtct  aatcttcccg  tgtactgcca
19201  gggcttgtca  ttagaggact  ttagggagac  caagcaggct  agaaagtaga  gacagggagat
19261  acctatgtct  aatgcttcag  tttatacttc  ctaggttttt  ttcattgggg  ttttttgtaac
19321  tcttttggta  tcctaccggt  gcttggtag   cctactgaac  cctgtcttttc ttcttaagga
19381  cattctgagc  atgtgagacc  tgaggactgc  aaacagctat  aagaggctcc  aaattaatca
19441  tatctttccc  tttgagaatc  tggccaagct  ccagctaatc  tacttggatg  ggttgccagc
19501  tatctggaga  aaaaggtagt  ttgggaatt   tattgttgta  gtgcttctgt  ctttggattg
19561  aacttcccac  aactctcctt  tttaaagcag  aacacagctg  ggcatggtgg  ctcctgcttg
19621  taattccagg  gctttgggag  gttgaggtgg  gggatcact   tgaggccagg  agttgaagac
19681  ccatgtctct  acaataaaat  aaaattagtt  gggcatggtg  gtacgtgcct  gtagtcctac
19741  ctactctgga  ggctgaggca  gcaggattgc  ttgagcccag  gagttcaagg  ctgcagtgag
```

FIG. 7F

```
19801 ccatcattag ccactgcact ccagcctagg tggcagagcg ggacccagtc tcttaaaaag
19861 aaagaaaagc agaacgtgag ccagttttca tcaattccta tactttttct tttgcatgta
19921 cacatacatt ttaactttac ataatgagtt cggcctgttt catttatccc tcagagctgg
19981 gctccagtga ggtctgtaag ggcaagcata cttgatcccc aatgaagaat gagagatgca
20041 aagcactaaa ttatttcttt tctcaccaca cagcaagata gatttaatga acttaacacc
20101 ttttgattag tggcctttta aattattccc actttccttt ggcagatggg tattaagttc
20161 tcaggatttg tttacaaata agactaactt catctgtatt agctcagttt tggtaggcct
20221 aattccatta tcactgccat ttccttgttt taagaaatca aaatttctta gcttgaaaaa
20281 caattgaaat tgttaaaaag tggaatagga gagcccggg ggctgtata aggaatttac
20341 tgaatccctg gttttctgta ccttgttttt ccttctgcat agatttgctt aactgttttt
20401 gtggcgtgta ttttttttt ttcgcagttt cgctcttgtt gcccaggctg gagtgcaatg
20461 gcgcaatctc agctcactgc aacctctgtc tctgggttc aagttattct cctgcctcag
20521 cctctcgagt agctgagatt acaggcatgc gcgaccacgc caggctaatt ttgtattttt
20581 agtagagacg gggtttctcc atgttggtca ggctggtctc aaactcctga cctcaggtga
20641 ttcaccgcc tcgactccc aaactgctgg gattacaggc gtgagccacc acgcctggcc
20701 agctgttgtt ataactggag ttctatgtgc ttgtgaccat tcttggtttc tccgaatatc
20761 ctagaacttt ggtggcgccc tattatacag gttgttgaag aaatgttacc atgtggattg
20821 agtaggaaac aattctcttt atcttggcaa tattatgcca tggcactact taaagtacaa
20881 attaaaagag ggggatgcta cagaactagc tgacaggcac tttgatagag gtggattct
20941 cagttcttaa aatagctctt tataaaggaa gccagaggca ttgtgagga gaattcttac
21001 ataactcata gggttagacc acatccgacc ttttctgtgt ggcttcatgg ctctcttggt
21061 tgagaaagca ttagtttctc cttccattag tttcaacctc ttgatttctt gaccccccta
21121 ctatattttg tgctgagaac acaagggtat taacaaccca cattgtagag gatcgctcag
21181 taataaagac tggagaataa aatgcagcat gggaatattg gcaattactc agttctaaat
21241 ttctcttgga aatgagggaa agcatacaga atagagctgg aatgaataggg ataatttttt
21301 ttttttttgc taagttggta gccagaatat aacagctccg cacaactgta aatgtccact
21361 cttcaatcca catgaagaaa agggtaaaaa tatggttgaa ctcaaccact agttgcccat
21421 tagaacagac tttcccagtg tactgcattt caatactttt tcttttatct cttttcagat
21481 cttcctcaga agaataggct tgttgtttta cagtgttagt gatccattcc ctttgacgat
21541 ccctaggtgg agatggggca tgaggatcct ccaggggaaa agctcactac cactgggcaa
21601 caaccctagg tcaggaggtt ctgtcaagat actttcctgg tcccagatag gaagataaag
21661 tctcaaaaac aaccaccaca cgtcaaggtg cgtaagctgt ccctaaaagc ataataagta
21721 gtcttaattt tgattttgtt ttccagtata cattgcactt agtgtttcac tgaggtcgta
21781 ttcatcatta ttctgcatat gatttggtaa aaacagcttc ctaactaacc tgggaagcaa
21841 ctgggtgtga gattaactgg ttaaagtgat gatgtaaaga gggtagcggg ttgcatgtgt
21901 tcgggtgttt ggagtgggac tatagcacgt ggcagaggct tacagctaag ttgttctttt
21961 aggagaacat ggacaactgt cacatcagtg acattgatca catgggcaaa tcattctgtt
22021 ccatgtggtc cccaaagtct ctcttaaagc cttacagaag aactttgcca atcatttaca
22081 tacttcagga tggcttggga tgccatggtg tataatacaa caagtgagag gtgtgtctt
22141 ttatgctatg gttgctgatt gatggaagcc gcataaatac aaatggaaac ctgactaaaa
22201 atggcacaaa gttatctgtc atcaggcagg agctaaagaa ccaggaccct acattctcta
22261 ggtcagtgtt gggagaggct gattagcgag tgagaattgg cagataaagg tgaccattcg
22321 gtgcaataaa tcctgaacgt ataggctttg cccagcattc ttcgtaaata gtgggtagct
22381 ataaatttca tgaaatattt tcatgggtaa gaacttttga aatgttataa ttgactagaa
22441 atctctgtag atttagaaat agagagttac taacaaattg ttagaaagtc taggaactag
22501 aaagctaagt tgagagttat ctaggaagat ctatctattg tactcataat ctttagataa
22561 attcctag ggccagtagt ctatgtgaat tttctttttc ttcttcttct tcttctttt
22621 tttgtatt tagctgcaat gttaaacaac ctatgtgaat tttcttattg tgagaatatt
22681 tgccttccag agtgactcac ctttatctca aagagcaata ttgtgagttt tgaaaatgct
22741 gctctaaggc tgtgttttgt tagtcctgag ccaggagact taaagcaaac ttgaggggtc
22801 ttaaaacatc gaagtgagcc ttaaacattg ggaagacctt atgttttcc ctctcatatc
22861 tattatttt gtgatctcag ttattaatca tttaagggga ctcttccta gctgattgc
22921 acttaaaaca ggatggaagt cttttttttt tttttttttt ttgagatgga gtttgctct
22981 tgttgcccag gctggagtgc aatggtgcaa tctcagctca ctgcaacctc tgcctcccgg
23041 gttcaagcga ttctcctgcc tcagcctccc aagtagctgg gattacagtc atgcaccacc
```

FIG. 7G

```
23101 acgcccggct aattttgtat ttttaataga gacggtgttt ctccatgttg gtcaggctgg
23161 tctcaaactc ctgacctcag gtgatccgcc cacctcaacc tcccaaagtg ctgggattat
23221 gggcgtgagc caccgcgccc ggcagttctg gtctttaact aaggtataag gctatgactg
23281 gtagtggtgt ctctagtgac tcatcaagtg atatttggca agacattttc ccatttatgc
23341 cagtttccta ttctgttgaa tgaggaaatt ttctctctaa agacctaaaa gttttgactt
23401 tataggtttc aaagttctgt ggaaacatttt tctattgctt attaatttga atcttatgta
23461 actctagcac agtactcaat atttatggca tttacatggt ttatctcatg ttttttttata
23521 gctcttcatt gttcctatct gccaaatcat tatacttcct acaagcagtg cagagagctg
23581 agtcttcagc aggtccaaga aatttgaaca cactgaagga agtcagcctt cccacctgaa
23641 gatcaacatg cctggcactc tagcacttga ggatagctga atgaagtaag ttgttgatgt
23701 tgcagtcctg tgaggatcac ttcagaactg ttataacagc tgttttttgg gagctggtgt
23761 tggatgggt gtgttggtct aatgtgaagt gggctaaat gtgagatgga aagatgacca
23821 gtcttccata ttactgactg ggttcactga agcaactcaa agacattatg gtcttcttac
23881 cagttgtatc acagaagaat ttagcctttg cttgtgtgtt ctatgtcttc actgtatagg
23941 ccctctgtca ttcttagagc cttaaacgtt gagaagctta aaacaccatt tctgctttct
24001 gctgaaaggg taaccctttc tcatctccgt ttgtgagaga ctctgtcgtc agttaagatt
24061 agtgtaaaaa gaaaactaaa ctctgaagta gccattataa aagtgtgaga atgaagtcag
24121 ttttctaaag agttgggaa aggtgatgct aaaggagggg attgagcaag tcctatcaaa
24181 gagccttta tgaaaatact tagtcatctg tgacatccca tttggctctt ccagaaatcc
24241 tagtaaatag ttgtaacagg atgttaagag gcatacattg tgtgttttaa atcctctgct
24301 actcattagg tatatgacct ttgacaactt aaagtctcta gacttctctg tttgtgaggg
24361 ttaaatgaaa tcatgtatgt aaagtgctca cctattgcag tgcctggcac atgtcaagta
24421 aaaggtaacc caagaagact cataagttca tttcccacaa tataagtgac cactagcact
24481 atcaggtagc aggcagagtt ggcatgcttt ggttctatgt aagaaatcct aaggtaaaa
24541 gtttataaat agaagagcat ctgtgttggt attggtggtt gttattattg tagtactata
24601 agtagtattc gtagtaacaa tagtttatta taattactaa tgacacttt tgattttttt
24661 tatctttctg tgatgctttt catgcctctt gtgccctca ctgtatcttg cctcttctac
24721 tacttacttc ctctgaatgt ctgcctttgc ttatctcttg cactcaagtg tgtatttctt
24781 tgtctcttc tttcttgtct ttgctctttg ttctctatct aaagtgtgtc ttacccattt
24841 ccatgtttct cttgctaatt tctttcgtgt gtgcctttgc ctcatttct cttttttgttc
24901 acaagagtgg tctgtgtctt gtcttagaca tatctctcat ttttcattt gttgctattt
24961 ctctttgctc tcctagatgt ggctcttctt tcacgcttta tttcatgtct cctttttggg
25021 tcacatgctg tgtgcttttt gtccttttct tgttctgtct acctctcctt tctctgccta
25081 cctctctttt ctctttgtga actgtgatta tttgttaccc cttcccttc tgttcgttt
25141 taaatttcac cttttttctg agtctggcct cctttctgct gtttctactt tttatctcac
25201 atttctcatt tctgcatttc ctttctgcct ctcttgggct attctctctc tcctcccctg
25261 cgtgcctcag catctcttgc tgtttgtgat tttctatttc agtattaatc tctgttggct
25321 tgtatttgtt ctctgcttct tcccttttcta ctcacctttg agtatttcag cctcttcatg
25381 aatctatctc cctctctttg atttcatgta atctctcctt aaatatttct ttgcatatgt
25441 gggcaagtgt acgtgtgtgt gtgtcatgtg tggcagaggg gcttcctaac cctgcctga
25501 taggtgcaga acgtcggcta tcagagcaag cattgtggag cggttcctta tgccaggctg
25561 ccatgtgaga tgatccaaga ccaaaacaag gccctagact gcagtaaaac ccagaactca
25621 agtagggcag aaggtccgag gctcatatgg atagaaggcc caaagtataa gacagatggt
25681 ttgagacttg agacccgagg actaagatgg aaagcccatg ttccaagata gatagaagcc
25741 tcaggcctga aaccaacaaa agcctcaaga gccaagaaaa cagagggtgg cctgaattgg
25801 accgaaggcc tgagttggat ggaagtctca aggcttgagt tagaagtctt aagacctggg
25861 acaggacaca tggaaggcct aagaactgag acttgtgaca caaggccaac gacctaagat
25921 tagcccaggg ttgtagctgg aagacctaca acccaaggat ggaaggcccc tgtcacaaag
25981 cctacctaga tggatagagg acccaagcga aaaggtatc tcaagactaa cggccggaat
26041 ctggagccc atgacccaga acccaggaag gatagaagct tgaagacctg gggaaatccc
26101 aagatgagaa ccctaaaccc tacctctttt ctattgttta cacttcttac tcttagatat
26161 ttccagttct cctgtttatc tttaagcctg attcttttga gatgtacttt tgatgttgc
26221 cggttacctt tagattgaca gtattatgcc tgggccagtc ttgagccagc tttaaatcac
26281 agcttttacc tatttgttag gctatagtgt tttgtaaact tctgttccta ttcacatctt
26341 ctccacttga gagagacacc aaaatccagt cagtatctaa tctggctttt gttaacttcc
```

FIG. 7H

```
26401 ctcaggagca gacattcata taggtgatac tgtatttcag tcctttcttt tgacoccaga
26461 agccctagac tgagaagata aaatggtcag gttgttgggg aaaaaaaagt gccaggctct
26521 ctagagaaaa atgtgaagag atgctccagg ccaatgagaa gaattagaca agaaatacac
26581 agatgtgcca gacttctgag aagcacctgc cagcaacagc ttccttcttt gagcttaggt
26641 gagcaggatt ctggggtttg ggatttctag tgatggttat ggaagggtg actgtgcctg
26701 ggacaaagcg aggtcccaag gggacagcct gaactccctg ctcatagtag tggccaaata
26761 atttggtgga ctgtgccaac gctactcctg ggtttaatac ccatctctag gcttaaagat
26821 gagagaacct gggactgttg agcatgttta atactttcct tgatttttt cttcctgttt
26881 atgtgggaag ttgatttaaa tgactgataa tgtgtatgaa agcactgtaa aacataagag
26941 aaaaaccaat tagtgtattg gcaatcatgc agttaacatt tgaagtgca gtgtaaattg
27001 tgaagcatta tgtaaatcag gggtccacag tttttctgta agggtcaaa tcataaatac
27061 tttagactgt gggccatatg gtttctgtta catatttgtt ttttaaacaa cgtttttata
27121 aggtcaaaat cattcttagt ttttgagcca attggatttg gcctgctgtt catagcttac
27181 caccccctga tgtattattt gttattcaga gaaaatttct gaatactact agtttccttt
27241 tctgtgcctg tccctgtgct aggcactaaa aatgcaatga ttattgatat ctaggtgacc
27301 tgaaaaaaaa tagtgaatgt gctttgtaaa ctgtaaagca cttgtattct actgtgataa
27361 gcgttgtgga tacaaagaaa ggagcaagca taaaaagtg ctctttcaaa aggatatagt
27421 actatgcaga cacaaggaat tgtttgataa atgaataaat tatatgtata tttgaggcca
27481 atttgtgttt gctgctctgg taattttgag taaaaatgca gtattccagg tatcagaaac
27541 gaaaacacat ggaaactgct tttaaacttt aaaatatact gaaaacataa gggactaagc
27601 ttgttgtggt cacctataat gtgccagata ccatgctggg tgctagagct accaaagggg
27661 gaaagtatt ctcatagaac aaaaaatttc agaaaggtgc atattaaagt gctttgtaaa
27721 ctaaagcatg atacaaatgt caatgggcta catatttatg aatgaatgaa tggatgaatg
27781 aatattaagt gcctcttaca taccagctat tttgggtact gtaaaataca agattaattc
27841 tcctatgtaa taagaggaaa gtttatcctc tatactattc agatgtaagg aatgatatat
27901 tgcttaattt taaacaatca agactttact ggtgaggtta agttaaatta ttactgatac
27961 attttccag gtaaccagga aagagctagt atgaggaaat gaagtaatag atgtgagatc
28021 cagacgaaa gtcacttaat tcagcttgcg aatgtgctt ctaaattata aagcacttgt
28081 aaatgaaaaa tttgatgctt tctgtatgaa taaaacttc tgtaagctag gtattgtctc
28141 tacaaaattc tcattgtata gttaaaccac agtgagaagg gttctataag tagttataca
28201 aaccaagggt ttaaatacct gttaaataga tcaatttga ttgcctacta tgtgaactca
28261 ctgttaaagg cactgaaaat ttatcatatt tcatttagcc acagccaaaa ataaggcaat
28321 acctagtgtta gcatttgtg aactctaagg caccatataa atgtaactgt tgattttctc
28381 acttggtgct gggtactagg tttataaaat tgtatgatag ttattatatt gtgcaaataa
28441 agtaggaaaa tttgaataac aatgattatc ttttgaatac gcatacgcaa gggattggtt
28501 gtctgaagaa tgccactata gtagttatct attgtgtgcc aatctcattg ctaggcattg
28561 gggatgcaaa gataaaccat ctttattgtg tcttgggtag cagaagaaaa tatgtgtaaa
28621 atcaatttat aatttgtaaa ctgccaccca tatataagct atatctgctg aatgatcatt
28681 gattactctt atccttagag ataacaactg ggggcacaaa catttattat cattattgaa
28741 cctacaacag agatctatgt gtagatttac aaagcctaca gttctataca gataggaatg
28801 aactattggc ttactgaatg gtgattactt tctgtggggc tcggaactac atgccctagg
28861 atataaaaat gatgttatca ttatagagtg ctcacagaga gaaatgaagt aataggtg
28921 tgagatccag accaaaagtc atttaaccaag tttattcagt gatgaaaaca tgggacaaat
28981 ggactaatat aaggcagtgt actaagctga gtagagagat aaagtcctgt ccagaagata
29041 catgcttcct ggctgattg aggagatgga aaattttgc aaaaaacaag gtgttgtggt
29101 cttccatcca gtttcttaag tgctgatgat aaaagtgaat tagacccacc ttgacctggc
29161 ctacagaagt aaaggagtaa aaataaatgc ctcaggcgtg ctttttgatt catttgataa
29221 acaaagcatc ttttatgtgg aatataccat tctgggtcct gaggataaga gagatgaggg
29281 cattagatca ctgacagctg aagatagaag aacatctttg gtttgattgt ttaaataata
29341 tttcaatgcc tattctctgc aaggtactat gtttcgtaaa ttaaataggt ctggcccaga
29401 agaccactc aattgccttt gagattaaaa aaaaaaaaaa aagaaagaa aaatgcaagt
29461 ttctttcaaa ataaagagca attttttccta gtttcaggaa tccccaaat cacttcctca
29521 ttggcttagt ttaaagccag gagactgaata aaagggctca gggtttgttc tttaattcat
29581 taactaaaca ttctgctttt attacagtta aatggttcaa gatgtaacaa ctagttttaa
29641 aggtatttgc tcattggtct ggcttagaga caggaagaca tatgagcaat aaaaaaaaga
```

FIG. 7I

```
29701  ttcttttgca tttaccaatt tagtaaaaat ttattaaaac tgaataaagt gctgttctta
29761  agtgcttgaa agacgtaaac caaagtgcac tttatctcat ttatcttatg gtggaaacac
29821  aggaacaaat tctctaagag actgtgtttc tttagttgag aagaaacttc attgagtagc
29881  tgtgatatgt tcgatactaa ggaaaaacta aacagatcac ctttgacatg cgttgtagag
29941  tgggaataag agagggcttt ttattttttc gttcatacga gtattgatga agatgatact
30001  aaatgctaaa tgaaatatat ctgctccaaa aggcatttat tctgacttgg agatgcaaca
30061  aaaacacaaa aatggaatga agtgatactc ttcatcaaac agaagtgact gttatctcaa
30121  ccattttgtt aaatcctaaa cagaaaacaa aaaaaatcat gacgaaaaga cacttgctta
30181  ttaattggct tggaaagtag aatataggag aaaggttact gtttattttt tttcatgtat
30241  tcattcattc tacaaatata ttcgggtgcc aataggtact tggtataagg tttttggccc
30301  cagagacatg ggaaaaaaat gcatgccttc ccagagaatg cctaatactt tccttttggc
30361  ttgtttttctt gttaggggca tggcttagtc cctaaataac attgtgtggt ttaattccta
30421  ctccgtatct cttctaccac tctggccact acgataagca ggtagctggg ttttgtagtg
30481  agcttgctcc ttaagttaca ggaactctcc ttataataga cacttcalttt tcctagtcca
30541  tccctcatga aaaatgactg accactgctg ggcagcagga gggatgatga ccaactaatt
30601  cccaaacccc agtctcattg gtaccagcct tggggaacca cctacacttg agccacaatt
30661  ggttttgaag tgcatttaca aggtttgtct attttcagtt ctttactttt tacatgctga
30721  cacatacata cactgcctaa atagatctct ttcagaaaca atcctcagat aacgcatagc
30781  aaaatggaga tggagacatg atttctcatg caacagcttc tctaattata ccttagaaat
30841  gttctccttt ttatcatcaa atctgctcaa gaaggctttt ttatagtaga ataatatcag
30901  tggatgaaaa cagcttaaca ttttaccatg cttaagtttt aagaataaaa taaaaattgg
30961  aaataattgg ccaaaattga aaggaaaaat tttttttaaaa tttctctaaa tgtaggcctg
31021  gctgggcttt gaccttttcc gtttttaaat cactcacaga gggtgggaca ggaggaagag
31081  tgaaggaaaa ggtcaaacct gttttaaggg caacctgcct ttgttctgaa ttggtcttaa
31141  gaacattacc agctccaggt ttaaattgtt cagtttcatg cagttccaat agctgatcat
31201  tgttgagatg aggacaaaat cctttgtcct cactagtttg ctttacattt ttgaaaagta
31261  ttattttgt ccaagtgctt atcaactaaa ccttgtgtta ggtaagaatg gaatttatta
31321  agtgaatcag tgtgaccctt cttgtcataa gattatctta aagctgaagc caaaatatgc
31381  ttcaaaagaa gaggacttta ttgttcattg tagttcatac attcaaagca tctgaactgt
31441  agtttctata gcaagccaat tacatccaata agtggagaag gaaatagata aatgtcaaag
31501  tatgattggt ggagggagca aggttgaaga taatctgggg ttgaaatttt ctagttttca
31561  ttctgtacat ttttagttag acatcagatt tgaaatatta atgtttacct ttcaatgtgt
31621  ggtatcagct ggactcagta acacccecttt cttcagctgg ggatggggaa tggattattg
31681  gaaatggaa agaagaaagt aactaaaagc cttcctttca cagtttctgg catcactacc
31741  actactgatt aaacaagaat aagagaacat tttatcatca tctgctttat tcacataaat
31801  gaagttgtga tgaataaatc tgcttttatg cagacacaag gaattaagtg gcttcgtcat
31861  tgtccttcta cctcaaagat aatttattcc aaaagctaag ataaatggaa gactcttgaa
31921  cttgtgaact gatgtgaaat gcagaatctc ttttgagtct ttgctgtttg gaagattgaa
31981  aaatattgtt cagcatgggt gaccaccaga aagtaatctt aagccatcta gatgtcacaa
32041  ttgaaacaaa ctggggagtt ggttgctatt gtaaaataaa atatactgtt ttga
       (SEQ ID NO:2)
```

FIG. 7J

SEQUENCE LISTING

<160> NUMBER OF SEQ ID NOS: 2

<210> SEQ ID NO 1
<211> LENGTH: 16481
<212> TYPE: DNA
<213> ORGANISM: Homo sapiens

<400> SEQUENCE: 1

| | | | | | | |
|---|---|---|---|---|---|---|
| ccttcagttc | ttaaagcgct | gcaattcgct | gctgcagcca | tatttcttac | tctctcgggg | 60 |
| ctggaagctt | cctgactgaa | gatctctctg | cacttggggt | tctttctaga | acattttcta | 120 |
| gtcccccaac | accctttatg | gcgtatttct | ttaaaaaaat | cacctaaatt | ccataaaata | 180 |
| ttttttttaaa | ttctatactt | tctcctagtg | tcttcttgac | acgtcctcca | tattttttta | 240 |
| aagaaagtat | ttggaatatt | tgaggcaat | ttttaatatt | taaggaattt | ttctttggaa | 300 |
| tcattttttgg | tgacatctct | gttttttgtg | gatcagtttt | ttactcttcc | actctcttt | 360 |
| ctatattttg | cccatcgggg | ctgcggatac | ctggttttat | tatttttct | ttgcccaacg | 420 |
| gggccgtgga | tacctgcctt | ttaattcttt | tttattcgcc | catcggggcc | gcggatacct | 480 |
| gcttttatt | ttttttcct | tagcccatcg | gggtatcgga | tacctgctga | ttcccttccc | 540 |
| ctctgaaccc | ccaacactct | ggcccatcgg | ggtgacggat | atctgctttt | taaaaatttt | 600 |
| ctttttttgg | cccatcgggg | cttcggatac | ctgcttttt | tttttttatt | ttccttgccc | 660 |
| atcgggggcct | cggatacctg | ctttaatttt | tgttttcctg | cccatcgggg | ccgcggatac | 720 |
| ctgctttgat | tttttttttt | catcgcccat | cggtgcttt | tatggatgaa | aaaatgttgg | 780 |
| ttttgtgggt | tgttgcactc | tctggaatat | ctacactttt | ttttgctgct | gatcatttgg | 840 |
| tggtgtgtga | gtgtacctac | cgcttttggca | gagaatgact | ctgcagttaa | gctaagggcg | 900 |
| tgttcagatt | gtggaggaaa | agtggccgcc | attttagact | tgccgcataa | ctcggcttag | 960 |
| ggctagtcgt | ttgtgctaag | ttaaactagg | gaggcaagat | ggatgatagc | aggtcaggca | 1020 |
| gaggaagtca | tgtgcattgc | atgagctaaa | cctatctgaa | tgaattgatt | tggggcttgt | 1080 |
| taggagcttt | gcgtgattgt | tgtatcggga | ggcagtaaga | atcatctttt | atcagtacaa | 1140 |
| gggactagtt | aaaaatggaa | ggttaggaaa | gactaaggtg | cagggcttaa | aatggcgatt | 1200 |
| ttgacattgc | ggcattgctc | agcatggcgg | gctgtgcttt | gttaggttgt | ccaaaatggc | 1260 |
| ggatccagtt | ctgtcgcagt | gttcaagtgg | cgggaaggcc | acatcatgat | gggcgaggct | 1320 |
| tgttaagtg | gttagcatgg | tggtggacat | gtgcggtcac | acaggaaaag | atggcggctg | 1380 |
| aaggtcttgc | cgcagtgtaa | aacatggcgg | gcctctttgt | ctttgctgtg | tgcttttcgt | 1440 |
| gttgggtttt | gccgcaggga | caatatggca | ggcgttgtca | tatgtatatc | atggcttttg | 1500 |
| tcacgtggac | atcatggcgg | gcttgccgca | ttgttaaaga | tggcgggttt | tgccgcctag | 1560 |
| tgccacgcag | agcgggagaa | aaggtgggat | ggacagtgct | ggattgctgc | ataacccaac | 1620 |
| caattagaaa | tggggggtgga | attgatcaca | gccaattaga | gcagaagatg | gaattagact | 1680 |
| gatgacacac | tgtccagcta | ctcagcgaag | acctgggtga | attagcatgg | cacttcgcag | 1740 |
| ctgtctttag | ccagtcagga | gaaagaagtg | gaggggccac | gtgtatgtct | cccagtgggc | 1800 |
| ggtacaccag | gtgttttcaa | ggtcttttca | aggacattta | gcctttccac | ctctgtcccc | 1860 |
| tcttatttgt | cccctcctgt | ccagtgctgc | ctcttgcagt | gctggatatc | tggctgtgtg | 1920 |
| gtctgaacct | ccctccattc | ctctgtattg | gtgcctcacc | taaggctaag | tatacctccc | 1980 |
| cccccacccc | ccaaccccc | caactcccca | ccccacccc | ccaccccca | cctcccacc | 2040 |
| cccctacccc | cctaccccc | taccccctc | tggtctgccc | tgcactgcac | tgttgccatg | 2100 |

```
ggcagtgctc caggcctgct tggtgtggac atggtggtga gccgtggcaa ggaccagaat    2160
ggatcacaga tgatcgttgg ccaacaggtg gcagaagagg aattcctgcc ttcctcaaga    2220
ggaacaccta ccccttggct aatgctgggg tcggattttg atttatattt atcttttgga    2280
tgtcagtcat acagtctgat tttgtggttt gctagtgttt gaatttaagt cttaagtgac    2340
tattatagaa atgtattaag aggctttatt tgtagaattc actttaatta catttaatga    2400 gttttttgttt tgagttcctt aaaattcctt aaagttttta gcttctcatt acaaattcct    2460 taacctttt ttggcagtag atagtcaaag tcaaatcatt tctaatgttt taaaaatgtg    2520
ctggtcattt tctttgaaat tgacttaact attttccttt gaagagtctg tagcacagaa    2580
acagtaaaaa atttaacttc atgacctaat gtaaaaaaga gtgtttgaag gtttacacag    2640
gtccaggcct tgctttgttc ccatccttga tgctgcacta attgactaat cacctactta    2700
tcagacagga aacttgaatt gctgtggtct ggtgtcctct attcagactt attatattgg    2760
agtatttcaa ttttcgttg tatcctgcct gcctagcatc cagttcctcc ccagccctgc    2820
tcccagcaaa cccctagtct agccccagcc ctactcccac ccggcccagc cctgcccca    2880 ggcccagtcc cctaacccc cagccctagg cccagtccca gtcctagttc ctcagtctgt    2940
ccagcttctc tcgaaagtca ctctaatttt cattgattca gtgctcaaaa taagttgtcc    3000
attggtatcc tattatactg ggatattccg tttaccttg gcattgctga tcttcagtac    3060
tgactccttg accattttca gttaagcata caatcccatt tgtctgtgat ctcaggacaa    3120
agaatttcct tactcggtac gttgaagtta gggaatgtca attgagagct ttctatcaga    3180
gcattattgc ccacaattg agttacttat cattttctcg atccctgcc cttaaaggag    3240 aaaccatttc tctgtcattg cttctgtagt cacagtccca atttgagta gtgatctttt    3300 cttgtgtact gtgttggcca cctaaaactc tttgcattga gtaaaattct aattgccaat    3360
aatcctaccc attggattag acagcactct gaaccccatt tgcattcagc aggggtcgc    3420 agacaaccg tcttttgttg gacagttaaa atgctcagtc ccaattgtca tagctttgcc    3480
tattaaacaa aggcaccta ctgcgctttt tgctgtgctt ctggagaatc ctgctgttct    3540
tggacaatta agaacaaag tagtaattgc taattgtctc acccattaat catgaagact    3600
accagtcgcc cttgcatttg ccttgaggca gcgctgacta cctgagattt aagagtttct    3660
taaattattg agtaaaatcc caattatcca tagttctgtt agttacacta tggcctttgc    3720
aaacatcttt gcataacagc agtgggactg actcattctt agagcccctt cccttggaat    3780
attaatggat acaatagtaa ttattcatgg ttctgcgtaa cagagaagac ccacttatgt    3840
gtatgccttt atcattgctc ctagatagtg tgaactacct accaccttgc attaatatgt    3900 aaacactaa ttgcccatag tcccactcat agtctagga tgtcctcttt gccattgctg    3960
ctgagttctg actacccaag tttccttctc ttaaacagtt gatatgcata attgcatata    4020
ttcatggttc tgtgcaataa aaatggattc tcaccccatc ccaccttctg tgggatgttg    4080
ctaacgagtg cagattattc aataacagct cttgaacagt taatttgcac agttgcaatt    4140
gtccagagtc ctgtccatta gaaagggact ctgtatccta tttgcacgct acaatgtggg    4200
ctgatcaccc aaggactctt cttgtgcatt gatgttcata attgtatttg tccacgatct    4260
tgtgcactaa cccttccact cccttttgtat tccagcaggg gacccttact actcaagacc    4320
tctgtactag gacagtttat gtgcacaatc ctaattgatt agaactgagt cttttatatc    4380
aaggtccctg catcatcttt gctttacatc aagagggtgc tggttaccta atgcccctcc    4440
```

```
tccagaaatt attgatgtgc aaaatgcaat ttccctatct gctgttagtc tggggtctca    4500
tccccctcata ttccttttgt cttacagcag ggggtacttg ggactgttaa tgcgcataat   4560
tgcaattatg gtcttttcca ttaaattaag atcccaactg ctcacaccct cttagcatta   4620
cagtagaggg tgctaatcac aaggacattt cttttgtact gttaatgtgc tacttgcatt   4680
tgtccctctt cctgtgcact aaagacccca ctcacttccc tagtgttcag cagtggatga   4740
cctctagtca agacctttgc actaggatag ttaatgtgaa ccatggcaac tgatcacaac   4800
aatgtctttc agatcagatc cattttatcc tccttgtttt acagcaaggg atattaatta   4860
cctatgttac ctttccctgg gactatgaat gtgcaaaatt ccaatgttca tggtctctcc   4920
ctttaaacct atattctacc ccttttacat tatagaaagg gatgctggaa acccagagtc   4980
cttctcttgg gactcttaat gtgtatttct aattatccat gactcttaat gtgcatattt   5040
tcaattgcct aattgatttc aattgtctaa gacatttcaa atgtctaatt gattagaact   5100
gagtctttta tatcaagcta atatctagct tttatatcaa gctaatatct tgacttctca   5160
gcatcataga aggggtact gatttcctaa agtcttcttt gaatttctat tatgcaaaat    5220
tgccctgagg ccgggtgtgg tggctcacac ctgtaatccc agcactttgg gaggctgagg   5280
tgggaagatc ccttactgcc aggagtttga ccagcctg gccaacatta aaaaaaaaaa    5340
aaaaagtaag acaattgccc tggaatccca tcccctcac acctccttgg caaagcagca    5400
ggagtgctaa ctagctagtg cttcttctct tatactgctt aaatgcgcat aattagcagt   5460
agttgatgtg cccctatgtt agagtagaat cccgcttcct tgctccattt gcattactgc   5520
aggagcttct aactagcctg aattcactct cttggactgt taatgtgcat acttatattt   5580
gctgctgtac ttttttacca tgtaaggacc ccacccactg tatttacatc ccagctggaa   5640
gtacctacta cttaagaccc ttagactagt aaagttagcg tgcataatct taggtgttat    5700
atacacattt tcagttgcat acagttgtgc cttttatcag gactcctgta cttatcaaag    5760
cagagagtgc taatcaatat taagcccttc tcttcgaact gtagatggca tgtaattgca    5820
gttgtcaatg gtccttcaat tagacttggg tttctgacct atcacaccct ctttgcttta   5880
ttgcatgggg tactattcac ttaaggcccc tttctcaaac tgttaatgtg cctaatgaca   5940
attacatcag tatccttcct tttgaaggac agcatggttg gtgacaccta aggcccatt    6000
tcttggcctc ccaatatgtg tgattgtatt tgtcgaggtt gctatgcact agagaaggaa   6060
agtgctcccc tcatccccac ttttcccttc cagcaggaag tgcccacccc ataagaccct   6120
tttatttgga gagtctaggt gcacaattgt aagtgaccac aagcatgcat cttggacatt   6180
tatgtgcgta atcgcacact gctcattcca tgtgaataag gtcctactct ccgacccctt   6240
ttgcaataca gaagggttgc tgataacgca gtccccttt cttggcatgt tgtgtgtgat    6300
tataatcgtc tgggatccta tgcactagaa aaggagggtc ctctccacat acctcagtct   6360
cacctttccc ttccagcagg gagtgcccac tccataagac tctcacattt ggacagtcaa   6420
ggtgcgtaat tgttaagtga acacaaccat gcaccttaga catggatttg cataactaca   6480
cacagctcaa cctatctgaa taaaatccta ctctcagacc ccttttgcag tacagcaggg   6540
gtgctgatca ccaaggccct ttttcctggc ctggtatgcg tgtgattatg tttgtcccgg   6600
ttcctgtgta ttagacatgg aagcctcccc tgccacactc cacccccaat cttcctttcc   6660
cttccggcag gagtgccctc tccataagac gcttacgttt ggacaatcaa ggtgcacagt   6720
tgtaagtgac cacaggcata caccttggac attaatgtgc ataaccactt tgcccattcc   6780
atctgaataa ggtcctactc tcagaccccct tttgcagtac agcaggggtg ctgatcacca   6840
```

```
aggccccttt tcttggcctg ttatgtgcgt gattatattt gtctgggttc ctgtgtatta    6900
gacaaggaag ccttccccccc gcccccaccc ccactcccag tcttcctttc ccttccagca    6960
gggagtgccc cctccataag atcattacat ttggacaatc aaggtgcaca attataagtg    7020
accacagcca tgcaccttgg acattattgg acattaatgt gcgtaactgc acatggccca    7080
tcccatctga ataaggacct actctcagat gcctttgcag tacagcaggg gtactgaatc    7140
accaaggccc ttttcttgg cctgttatgt gtgtgattat atttatccca gtttctgtgt     7200
aatagacatg aaagcctccc ctgccacacc ccacctccaa tcttcctttc ccttccacca    7260
gggagtgtcc actccatata cccttacatt tggacaatca aggtgcacaa ttgtaagtga    7320
gcataggcac tcaccttgga catgaatgtg cataactgca catggcccat cccatctgaa    7380
taaggtccta ctctcagacc cttttttgcag tacagcaggg gtgctgatca ccaaggcccc   7440
ttttcctggc ctgttatgtg tgtgattata tttgttccag ttcctgtgta atagacatgg    7500
aagcctcccc tgccacactc caccccccaat cttccttttcc ttctggcagg aagtacccgc  7560
tccataagac ccttacattt ggacagtcaa ggtgcacaat tgtatgtgac cacaaccatg    7620
caccttggac ataaatgtgt gtaactgcac atggcccatc ccatctgaat aaggtcctac    7680
tctcagaccc cttttgcagt acagtaggtg tgctgataac caaggcccct cttcctggcc    7740
tgttaacgta tgtgattata tttgtctggg ttccagtgta taagacatgg aagcctcccc    7800
tgccccaccc caccctcaat cttcctttcc cttctggcag ggagtgccag ctccataaga    7860
accttacatt tggacagtca aggtgcacaa ttctaagtga ccgcagccat gcaccttggt    7920
caataatgtg tgtaactgca cacggcctat ctcatctgaa taaggcctta ctctcagacc    7980
ccttttgcag tacagcaggg gtgctgataa ccaaggccca ttttcctggc ctgttatgtg    8040
tgtgattata tttgtccagg tttctgtgta ctagacaagg aagcctcctc tgccccatcc    8100
catctacgca taatctttct tttcctccca gcagggagtg ctcactccat aagacccctta   8160 catttggaca atcaaggtgc acaattgtaa gtgaccacaa ccatgcatct tggaaattta    8220
tgtgcataac tgcacatggc ttatcctatt tgaataaagt cctactctca gaccccctt    8280 gcagtatagc tggggtgctg atcactgagg cctctttgct tggcttgtct atattcttgt    8340
gtactagata agggcacctt ctcatggact cccttttgctt ttcaacaagg agtacccact    8400 acttttaag attcttatat ttgtccaaag tacatggttt taattgacca caacaatgtc     8460
ccttggacat taatgtatgt aatcaccaca tggttcatcc taattaaaca aagttctacc    8520
ttctcaccct ccatttgcag tataccaggg ttgctgaccc cctaagtccc cttttcttgg    8580
cttgttgaca tgcataattg catttatgtt ggttcttgtg ccctagacaa ggatgcccca    8640
cctcttttca atagtgggtg cccactcctt atgatcttta catttgaaca gttaatgtga    8700
ataattgcag ttgtccacaa ccctatcact tctaggacca ttatacctct tttgcattac    8760
tgtggggtat actgtttccc tccaaggccc cttctggtgg actatcaaca tataattgaa    8820
attttctttt gtctttgtca gtagattaag gtcataccccc atcacctttc ctttgtagta   8880
caacagggtg tcctgatcaa ccaaagtcct gttgttttgg actgttaata tgtgcaatta    8940
catttgctcc tgatctgtgc actagataag gatcctacct actttcttag tgttttttagc   9000 aggtagtgcc cactactcaa gactgtcact tggaatgttc atgtgcacaa actcaattct    9060
ctaagcatgt tcctgtacca ccttttgcttt agagcagggg gatgatattc actaagtgcc   9120 ccttctttttg gacttaatat gcattaatgc aattgtccac ctcttctttt agactaagag   9180
```

```
ttgatctcca catattcccc ttgcatcagg ggcatgttaa ttatgaatga acccttttct    9240
tttaatatta atgtcataat tgtatttgtg gacctgtgta ggagaaaaag accctatgtt    9300
cctcccatta ccctttggat tgctgctgag aagtgttaac tactcataat ctcagctctt    9360
ggacaattaa tagcattaat aacaattatc aagggcactg atcattagat aagactcctg    9420
cttcctcgtt gcttacatcg ggggtactga cccactaagg ccccttgtac tgttaatgtg    9480
aatatttgca attatatatg tctccttctg gtagagtggg atattatgcc ctagtatccc    9540 cttttgcatta ctgcagggggc tgctgactac tcaaaacttc tcctgggact gttaataggc   9600
acaatggcag ttatcaatgg ttttctccct ccctgacctt gttaagcaag cgccccaccc    9660 caccctagt ttcccatggc ataataaagt ataagcattg gagtattcca tgcacttgtc    9720
tatcaaacag tggtccatac tcccaacccct tttgcattgc gccagtgtgt aaaatcacag   9780
gtagccatgg tgtcatgctt tatatacgaa gtcttccctc tctctgcccc ttgtgtgccc    9840 ttggccccctt tttacagact attgctcaca atctcaggtg tccatatttg cagctattag   9900
gtaagattgt gctgtctccc tcttcccttc cctctgccct gccccttttg cctctttgct    9960
gggtaatgtt gaccagacaa ggcccctttct cttggactta aacaattctc agttgcactt   10020
tccttggtcc acccattata catgaacccc tctacttcct ttcgcattgc ttctgagtat    10080
gctgactacc caaagcccct tctgtgttat taataaacac agtactgatt gtcccatttt    10140
tcagcccatc agtccaagat ctccctacca cttggtgtg ttggtgcagt gttgactatg     10200
aaaagcaggc ctgaactagg tggataagcc ttcactcatt ttctttcatt tattaatgat    10260
cctagtttca attattgtca gattctgggg acaagaacca ttcttgccca cctgtgttac    10320
tgctttactg tgcaaaatac tgaaggcaag tcagacccag ggagctggat tgccatcctt    10380 tatttttgtgt ttccagtgta cactataaaa ttgtctcccc aggaaggaag gttggcactt   10440
tctctgcatt cttctttcca gagcagattg cctggttaag aatctcttgt tgtcccttct    10500
gtatattgtt attgtaaagt gccaaatgcc aggatacagc cagaaaaatt gcttattatt    10560
attaaaaaaa ttttttttaag aaagacatct ggattgtagg gtggactcga taacctggtc   10620
attatttttt tgaagccaaa atatccattt atactatgta cctggtgacc agtgtctctc    10680
attttaactg agggtggtgg gtctgtggat agaacactga ctcttgctat tttaatatca    10740
aagatattct agagtggaac tcttaagacc agtatctttg tgtgggcttt accagcattc    10800
acttttagaa aaactaccta aatttttataa tcctttaatt tcttcatctg gagcacctgc   10860
ccctacttat ttcaagaaga ttgcagtaaa acgattaaat gagggaacat atgcagaggt    10920
gcttttaaaa agcatatgcc accttttta ttaattatta tataaaatga agcatttaat     10980
tatagtaata atttgaagta gtttgaagta ccacactgag gtgaggactt aaaaatgata    11040
agacgagttc cctatttat aagaaaaata agccaaaatt aaatattctt ttggatataa    11100
atttcaacag tgagatagct gcctagtgga aatgaataat atcccagcca ctagtgtaca   11160
gggtgttttg tggcacagga ttatgtaata tggaactgct caagcaaata actagtcatc   11220
acaacagcag ttctttgtaa taactgaaaa agaatattgt ttctcggaga aggatgtcaa   11280
aagatcggcc cagctcaggg agcagttttgc cctactagct cctcggacag ctgtaaagaa   11340
gagtctctgg ctctttagaa tactgatccc attgaagata ccacgctgca tgtgtccta   11400 gtagtcatgt ctccttaggc tcctcttgga cattctgagc atgtgagacc tgaggactgc   11460
aaacagctat aagaggctcc aaattaatca tatctttccc tttgagaatc tggccaagct   11520
ccagctaatc tacttggatg ggttgccagc tatctggaga aaaagatctt cctcagaaga   11580
```

```
ataggcttgt tgttttacag tgttagtgat ccattcccctt tgacgatccc taggtggaga    11640
tggggcatga ggatcctcca ggggaaaagc tcactaccac tgggcaacaa ccctaggtca    11700
ggaggttctg tcaagatact ttcctggtcc cagataggaa gataaagtct caaaaacaac    11760
caccacacgt caagctcttc attgttccta tctgccaaat cattatactt cctacaagca    11820
gtgcagagag ctgagtcttc agcaggtcca agaaatttga acacactgaa ggaagtcagc    11880
cttcccacct gaagatcaac atgcctggca ctctagcact tgaggatagc tgaatgaatg    11940
tgtatttctt tgtctctttc tttcttgtct ttgctctttg ttctctatct aaagtgtgtc    12000
ttacccattt ccatgtttct cttgctaatt tctttcgtgt gtgcctttgc ctcattttct    12060 cttttttgttc acaagagtgg tctgtgtctt gtcttagaca tatctctcat ttttcatttt    12120
gttgctattt ctctttgctc tcctagatgt ggctcttctt tcacgctttta tttcatgtct    12180 cctttttggg tcacatgctg tgtgcttttt gtcctttttct tgttctgtct acctctcctt    12240
tctctgccta cctctctttt ctctttgtga actgtgatta tttgttaccc cttccccttc    12300
tcgttcgttt taaatttcac cttttttctg agtctggcct cctttctgct gtttctactt    12360
tttatctcac atttctcatt tctgcattttc ctttctgcct ctcttgggct attctctctc    12420 tcctccccctg cgtgcctcag catctcttgc tgtttgtgat tttctatttc agtattaatc    12480
tctgttggct tgtatttgtt ctctgcttct tcccttttcta ctcacctttg agtatttcag    12540
cctcttcatg aatctatctc cctctctttg atttcatgta atctctcctt aaatatttct    12600
ttgcatatgt gggcaagtgt acgtgtgtgt gtgtcatgtg tggcagaggg gcttcctaac    12660
ccctgcctga taggtgcaga acgtcggcta tcagagcaag cattgtggag cggttcctta    12720
tgccaggctg ccatgtgaga tgatccaaga ccaaaacaag gccctagact gcagtaaaac    12780
ccagaactca agtagggcag aaggtggaag gctcatatgg atagaaggcc caaagtataa    12840
gacagatggt ttgagacttg agacccgagg actaagatgg aaagcccatg ttccaagata    12900
gatagaagcc tcaggcctga aaccaacaaa agcctcaaga gccaagaaaa cagagggtgg    12960
cctgaattgg accgaaggcc tgagttggat ggaagtctca aggcttgagt tagaagtctt    13020
aagacctggg acaggacaca tggaaggcct aagaactgag acttgtgaca caaggccaac    13080
gacctaagat tagcccaggg ttgtagctgg aagacctaca acccaaggat ggaaggcccc    13140
tgtcacaaag cctacctaga tggatagagg acccaagcga aaaaggtatc tcaagactaa    13200
cggccggaat ctggaggccc atgacccaga acccaggaag gatagaagct tgaagacctg    13260
gggaaatccc aagatgagaa ccctaaaccc tacctctttt ctattgttta cacttcttac    13320
tcttagatat ttccagttct cctgtttatc tttaagcctg attcttttga gatgtacttt    13380
ttgatgttgc cggttacctt tagattgaca gtattatgcc tgggccagtc ttgagccagc    13440
tttaaatcac agcttttacc tatttgttag gctatagtgt tttgtaaact tctgtttcta    13500
ttcacatctt ctccacttga gagagacacc aaaatccagt cagtatctaa tctggctttt    13560
gttaacttcc ctcaggagca gacattcata taggtgatac tgtatttcag tcctttctttt    13620 tgacccccaga agccctagac tgagaagata aaatggtcag gttgttgggg aaaaaaaaag    13680
tgccaggctc tctagagaaa aatgtgaaga gatgctccag gccaatgaga agaattagac    13740
aagaaataca cagatgtgcc agacttctga gaagcacctg ccagcaacag cttccttctt    13800
tgagcttagg tgagcaggat tctggggttt gggattccta gtgatggtta tggaaagggt    13860
gactgtgcct gggacaaagc gaggtcccaa ggggacagcc tgaactccct gctcatagta    13920
```

```
gtggccaaat aatttggtgg actgtgccaa cgctactcct gggtttaata cccatctcta    13980
ggcttaaaga tgagagaacc tgggactgtt gagcatgttt aatactttcc ttgatttttt    14040
tcttcctgtt tatgtgggaa gttgatttaa atgactgata atgtgtatga aagcactgta    14100
aaacataaga gaaaaccaa ttagtgtatt ggcaatcatg cagttaacat ttgaaagtgc     14160
agtgtaaatt gtgaagcatt atgtaaatca ggggtccaca gttttctgt aagggtcaa      14220 atcataaata ctttagactg tgggccatat ggtttctgtt acatatttgt ttttaaaca    14280 acgttttat aaggtcaaaa tcattcttag ttttgagcc aattggattt ggcctgctgt      14340
tcatagctta ccaccccctg atgtattatt tgttattcag agaaaatttc tgaatactac    14400
tagtttcctt ttctgtgcct gtccctgtgc taggcactaa aaatgcaatg attattgata   14460
tctaggtgac ctgaaaaaaa atagtgaatg tgctttgtaa actgtaaagc acttgtattc   14520
tactgtgata agcgttgtgg atacaaagaa aggagcaagc ataaaaagt gctctttcaa    14580 aaggatatag tactatgcag acacaaggaa ttgtttgata atgaataaa ttatatgtat    14640 atttgaggcc aatttgtgtt tgctgctctg gtaattttga gtaaaaatgc agtattccag   14700
gtatcagaaa cgaaaacaca tggaaactgc ttttaaactt taaaatatac tgaaaacata   14760
agggactaag cttgttgtgg tcacctataa tgtgccagat accatgctgg gtgctagagc   14820
taccaagggg ggaaaagtat tctcatagca acaaaaaatt tcagaaaggt gcatattaaa   14880
gtgctttgta aactaaagca tgatacaaat gtcaatgggc tacatattta tgaatgaatg   14940
aatggatgaa tgaatattaa gtgcctctta cataccagct attttgggta ctgtaaaata   15000
caagattaat tctcctatgt aataagagga aagtttatcc tctatactat tcagatgtaa   15060
ggaatgatat attgcttaat tttaaacaat caagacttta ctggtgaggt taagttaaat   15120
tattactgat acatttttcc aggtaaccag gaaagagcta gtatgaggaa atgaagtaat   15180
agatgtgaga tccagaccga aagtcactta attcagcttg cgaatgtgct ttctaaatta   15240
taaagcactt gtaaatgaaa aatttgatgc tttctgtatg aataaaactt tctgtaagct   15300
aggtattgtc tctacaaaat tctcattgta tagttaaacc acagtgagaa gggttctata   15360
agtagttata caaaccaagg gtttaaatac ctgttaaata gatcaatttt gattgcctac   15420
tatgtgaact cactgttaaa ggcactgaaa atttatcata tttcatttag ccacagccaa   15480
aaataaggca atacctatgt tagcattttg tgaactctaa ggcaccatat aaatgtaact   15540
gttgattttc tcacttggtg ctgggtacta ggtttataaa attgtatgat agttattata   15600
ttgtgcaaat aaagtaggaa aatttgaata acaatgatta tcttttgaat acgcatacgc   15660
aagggattgg ttgtctgaag aatgccacta tagtagttat ctattgtgtg ccaatctcat   15720
tgctaggcat tggggatgca aagataaacc atctttattg tgtcttgggt agcagaagaa   15780
aatatgtgta aaatcaattt ataatttgta aactgccacc catatataag ctatatctgc   15840
tgaatgatca ttgattactc ttatccttag agataacaac tgggggcaca acatttatt    15900 atcattattg aacctacaac agagatctat gtgtagattt acgaagccta cagttctata   15960
cagataggaa tgaactattg gcttactgaa tggtgattac tttctgtggg gctcggaact   16020
acatgcccta ggatataaaa atgatgttat cattatagag tgctcacaga aggaaatgaa   16080
gtaatatagg tgtgagatcc agaccaaaag ttatttaaca agtttattca gtgatgaaaa   16140
catgggacaa atggactata taaggcagtg tactaagctg agtagagaga taaagtcctg   16200
tccagaagat acatgctttc ctggcctgat tgaggagatg gaaaattttt gcaaaaaaca   16260
aggtgtttgt ggtcttccat ccagtttctt aagtgctgat gataaaagtg aattagaccc   16320
```

| | | | | |
|---|---|---|---|---|
| accttgacct | ggcctacaga | agtaaaggag | taaaaataaa | tgcctcaggc gtgcttttg | 16380 |
| attcatttga | taaacaaagc | atcttttatg | tggaatatac | cattctgggt cctgaggata | 16440 |
| agagagatga | gggcattaga | tcactgacag | ctgaagatag | a | 16481 |

<210> SEQ ID NO 2
<211> LENGTH: 32094
<212> TYPE: DNA
<213> ORGANISM: Homo sapiens

<400> SEQUENCE: 2

| | | | | |
|---|---|---|---|---|
| cttcagttct | taaagcgctg | caattcgctg | ctgcagccat | atttcttact ctctcggggc | 60 |
| tggaagcttc | ctgactgaag | atctctctgc | acttggggtt | cttctagaa cattttctag | 120 |
| tcccccaaca | cccttttatgg | cgtatttctt | taaaaaaatc | acctaaattc cataaaatat | 180 |
| tttttttaaat | tctatacttt | ctcctagtgt | cttcttgaca | cgtcctccat atttttttaa | 240 |
| agaaagtatt | tggaatattt | tgaggcaatt | tttaatattt | aaggaatttt tctttggaat | 300 |
| cattttggt | tgacatctct | gttttttgtg | gatcagtttt | ttactcttcc actctctttt | 360 |
| ctatattttg | cccatcgggg | ctgcggatac | ctggttttat | tatttttttct ttgcccaacg | 420 |
| gggccgtgga | tacctgcctt | ttaattcttt | tttattcgcc | catcggggcc gcggatacct | 480 |
| gcttttatt | tttttttcct | tagcccatcg | gggtatcgga | tacctgctga ttcccttccc | 540 |
| ctctgaaccc | ccaacactct | ggcccatcgg | ggtgacggat | atctgctttt taaaaatttt | 600 |
| cttttttttgg | cccatcgggg | cttcggatac | ctgcttttt | ttttttttatt tttccttgcc | 660 |
| catcggggcc | tcggatacct | gctttaattt | ttgttttttct | ggcccatcgg ggccgcggat | 720 |
| acctgctttg | attttttttt | ttcatcgccc | atcggtgctt | tttatggatg aaaaaatgtt | 780 |
| ggttttgtgg | gttgttgcac | tctctggaat | atctacactt | ttttttgctg ctgatcattt | 840 |
| ggtggtgtgt | gagtgtacct | accgcttttgg | cagagaatga | ctctgcagtt aagctaaggg | 900 |
| cgtgttcaga | ttgtggagga | aaagtggccg | ccatttttaga | cttccgcat aactcggctt | 960 |
| agggctagtc | gtttgtgcta | agttaaacta | gggaggcaag | atggatgata gcaggtcagg | 1020 |
| cagaggaagt | catgtgcatt | gcatgagcta | aacctatctg | aatgaattga tttgggggctt | 1080 |
| gttaggagct | ttgcgtgatt | gttgtatcgg | gaggcagtaa | gaatcatctt ttatcagtac | 1140 |
| aagggactag | ttaaaaatgg | aaggttagga | aagactaagg | tgcagggctt aaaatggcga | 1200 |
| ttttgacatt | gcggcattgc | tcagcatggc | gggctgtgct | ttgttaggtt gtccaaaatg | 1260 |
| gcggatccag | ttctgtcgca | gtgttcaagt | ggcgggaagg | ccacatcatg atgggcgagg | 1320 |
| ctttgttaag | tggttagcat | ggtggtggac | atgtgcggtc | acacaggaaa agatggcggc | 1380 |
| tgaaggtctt | gccgcagtgt | aaaacatggc | gggcctcttt | gtctttgctg tgtgcttttc | 1440 |
| gtgttgggtt | ttgccgcagg | gacaatatgg | caggcgttgt | catatgtata tcatggcttt | 1500 |
| tgtcacgtgg | acatcatggc | gggcttgccg | cattgttaaa | gatggcgggt tttgccgcct | 1560 |
| agtgccacgc | agagcgggag | aaaaggtggg | atggacagtg | ctggattgct gcataaccca | 1620 |
| accaattaga | aatgggggtg | gaattgatca | cagccaatta | gagcagaaga tggaattaga | 1680 |
| ctgatgacac | actgtccagc | tactcagcga | agacctgggt | gaattagcat ggcacttcgc | 1740 |
| agctgtcttt | agccagtcag | gagaaagaag | tggaggggcc | acgtgtatgt ctcccagtgg | 1800 |
| gcggtacacc | aggtgttttc | aaggtctttt | caaggacatt | tagccttttcc acctctgtcc | 1860 |
| cctcttattt | gtcccctcct | gtccagtgct | gcctcttgca | gtgctggata tctggctgtg | 1920 |

```
tggtctgaac ctccctccat tcctctgtat tggtgcctca cctaaggcta agtatacctc    1980 ccccccacc cccaacccc cccaactccc caccccacc ccccacccc cacctcccca        2040 ccccctacc cccctacccc cctaccccc tctggtctgc cctgcactgc actgttgcca     2100
tgggcagtgc tccaggcctg cttggtgtgg acatggtggt gagccgtggc aaggaccaga    2160
atggatcaca gatgatcgtt ggccaacagg tggcagaaga ggaattcctg ccttcctcaa    2220
gaggaacacc tacccttgg ctaatgctgg ggtcggattt tgatttatat ttatcttttg    2280
gatgtcagtc atacagtctg attttgtggt ttgctagtgt ttgaatttaa gtcttaagtg    2340
actattatag aaatgtatta agaggcttta tttgtagaat tcactttaat tacatttaat    2400 gagttttgt tttgagttcc ttaaaattcc ttaaagtttt tagcttctca ttacaaattc    2460
cttaaccttt ttttggcagt agatagtcaa agtcaaatca tttctaatgt tttaaaaatg    2520
tgctggtcat tttctttgaa attgacttaa ctattttcct ttgaagagtc tgtagcacag    2580
aaacagtaaa aaatttaact tcatgaccta atgtaaaaaa gagtgtttga aggtttacac    2640
aggtccaggc cttgctttgt tcccatcctt gatgctgcac taattgacta atcacctact    2700
tatcagacag gaaacttgaa ttgctgtggt ctggtgtcct ctattcagac ttattatatt    2760
ggagtatttc aattttcgt tgtatcctgc ctgcctagca tccagttcct ccccagccct    2820
gctcccagca aaccctagt ctagcccag ccctactccc accccgcccc agccctgccc    2880
cagccccagt cccctaaccc cccagcccta gccccagtcc cagtcctagt tcctcagtcc    2940
cgcccagctt ctctcgaaag tcactctaat tttcattgat tcagtgctca aaataagttg    3000
tccattgctt atcctattat actgggatat tccgttacc cttggcattg ctgatcttca    3060
gtactgactc cttgaccatt ttcagttaat gcatacaatc ccatttgtct gtgatctcag    3120
gacaaagaat ttccttactc ggtacgttga agttagggaa tgtcaattga gagctttcta    3180
tcagagcatt attgcccaca atttgagtta cttatcattt tctcgatccc ctgcccttaa    3240
aggagaaacc atttctctgt cattgcttct gtagtcacag tcccaatttt gagtagtgat    3300
cttttcttgt gtactgtgtt ggccacctaa aactctttgc attgagtaaa attctaattg    3360
ccaataatcc tacccattgg attagacagc actctgaacc ccatttgcat tcagcagggg    3420
gtcgcagaca acccgtcttt tgttggacag ttaaaatgct cagtcccaat tgtcatagct    3480
ttgcctatta aacaaaggca ccctactgcg ctttttgctg tgcttctgga gaatcctgct    3540
gttcttggac aattaaagaa caaagtagta attgctaatt gtctcaccca ttaatcatga    3600
agactaccag tcgcccttgc atttgccttg aggcagcgct gactacctga gatttaagag    3660
tttcttaaat tattgagtaa aatcccaatt atccatagtt ctgttagtta cactatggcc    3720
tttgcaaaca tctttgcata acagcagtgg gactgactca ttcttagagc cccttcccctt    3780 ggaatattaa tggatacaat agtaattatt catggttctg cgtaacagag aagacccact    3840
tatgtgtatg cctttatcat tgctcctaga tagtgtgaac tacctaccac cttgcattaa    3900
tatgtaaaac actaattgcc catagtccca ctcattagtc taggatgtcc tctttgccat    3960
tgctgctgag ttctgactac ccaagtttcc ttctcttaaa cagttgatat gcataattgc    4020
atatattcat ggttcgtgc aataaaaatg gattctcacc ccatcccacc ttctgtggga    4080
tgttgctaac gagtgcagat tattcaataa cagctcttga acagttaatt tgcacagttg    4140
caattgtcca gagtcctgtc cattagaaag ggactctgta tcctatttgc acgctacaat    4200
gtgggctgat cacccaagga ctcttcttgt gcattgatgt tcataattgt atttgtccac    4260
gatcttgtgc actaacccctt ccactccctt tgtattccag caggggaccc ttactactca    4320
```

```
agacctctgt actaggacag tttatgtgca caatcctaat tgattagaac tgagtctttt    4380
atatcaaggt ccctgcatca tctttgcttt acatcaagag ggtgctggtt acctaatgcc    4440
cctcctccag aaattattga tgtgcaaaat gcaatttccc tatctgctgt tagtctgggg    4500
tctcatcccc tcatattcct tttgtcttac agcaggggga acttgggact gttaatgcgc    4560
ataattgcaa ttatggtctt ttccattaaa ttaagatccc aactgctcac accctcttag    4620
cattacagta gagggtgcta atcacaagga catttctttt gtactgttaa tgtgctactt    4680
gcatttgtcc ctcttcctgt gcactaaaga ccccactcac ttccctagtg ttcagcagtg    4740
gatgacctct agtcaagacc tttgcactag atagttaat gtgaaccatg caactgatc     4800 acaacaatgt ctttcagatc agatccattt tatcctcctt gttttacagc aagggatatt    4860
aattacctat gttacctttc cctgggacta tgaatgtgca aaattccaat gttcatggtc    4920
tctcccttta aacctatatt ctaccccttt tacattatag aaagggatgc tggaaaccca    4980
gagtccttct cttgggactc ttaatgtgta tttctaatta ccatgactc ttaatgtgca     5040 tattttcaat tgcctaattg atttcaattg tctaagacat ttcaaatgtc taattgatta    5100
gaactgagtc ttttatatca agctaatatc tagcttttat atcaagctaa tatcttgact    5160
tctcagcatc atagaagggg gtactgattt cctaaagtct ttcttgaatt tctattatgc    5220
aaaattgccc tgaggccggg tgtggtggct cacacctgta atcccagcac tttgggaggc    5280
tgaggtggga agatccctta ctgccaggag tttgagacca gcctggccaa cattaaaaaa    5340 aaaaaaagt aagacaattg ccctggaatc ccatccccct cacacctcct ggcaaagca     5400 gcaggagtgc taactagcta gtgcttcttc tcttatactg cttaaatgcg cataattagc    5460
agtagttgat gtgcccctat gttagagtag aatcccgctt ccttgctcca tttgcattac    5520
tgcaggagct tctaactagc ctgaattcac tctcttggac tgttaatgtg catacttata    5580
tttgctgctg tacttttta ccatgtaagg acccccaccca ctgtatttac atcccagctg    5640
gaagtaccta ctacttaaga cccttagact agtaaagtta gcgtgcataa tcttaggtgt    5700
tatatacaca ttttcagttg catacagttg tgccttttat caggactcct gtacttatca    5760
aagcagagag tgctaatcaa tattaagccc ttctcttcga actgtagatg gcatgtaatt    5820
gcagttgtca atggtccttc aattagactt gggtttctga cctatcacac cctctttgct    5880
ttattgcatg gggtactatt cacttaaggc cccttcttca aactgttaat gtgcctaatg    5940
acaattacat cagtatcctt ccttttgaag gacagcatgg ttggtgacac ctaaggcccc    6000
atttcttggc ctcccaatat gtgtgattgt atttgtcgag gttgctatgc actagagaag    6060
gaaagtgctc ccctcatccc cacttttccc ttccagcagg aagtgcccac cccataagac    6120 ccttttatt ggagagtcta ggtgcacaat tgtaagtgac cacaagcatg catcttggac     6180
atttatgtgc gtaatcgcac actgctcatt ccatgtgaat aaggtcctac tctccgaccc    6240
cttttgcaat acagaagggt tgctgataac gcagtcccct tttcttggca tgttgtgtgt    6300
gattataatc gtctgggatc ctatgcacta gaaaggagg gtcctctcca catacctcag    6360 tctcacccttt cccttccagc agggagtgcc cactccataa gactctcaca tttggacagt    6420
caaggtgcgt aattgttaag tgaacacaac catgcacctt agacatggat ttgcataact    6480
acacacagct caacctatct gaataaaatc ctactctcag acccctttttg cagtacagca    6540 ggggtgctga tcaccaaggc ccttttttcct ggcctggtat gcgtgtgatt atgtttgtcc    6600
cggttcctgt gtattagaca tggaagcctc ccctgccaca ctccacccc aatcttcctt     6660
```

```
tcccttccgg cagggagtgc cctctccata agacgcttac gtttggacaa tcaaggtgca      6720
cagttgtaag tgaccacagg catacacctt ggacattaat gtgcataacc actttgccca      6780
ttccatctga ataaggtcct actctcagac ccctttttgca gtacagcagg ggtgctgatc     6840
accaaggccc cttttcttgg cctgttatgt gcgtgattat atttgtctgg gttcctgtgt      6900
attagacaag gaagccttcc ccccgccccc accccactc ccagtcttcc tttcccttcc       6960
agcagggagt gcccctcca taagatcatt acatttggac aatcaaggtg cacaattata       7020
agtgaccaca gccatgcacc ttggacatta ttggacatta atgtgcgtaa ctgcacatgg      7080
cccatcccat ctgaataagg tcctactctc agatgccctt tgcagtacag caggggtact      7140
gaatcaccaa ggccctttttt cttggcctgt tatgtgtgtg attatattta cccagtttc     7200 tgtgtaatag acatgaaagc ctcccctgcc acccccacc tccaatcttc ctttcccttc       7260
caccagggag tgtccactcc atatacccctt acatttggac aatcaaggtg cacaattgta    7320
agtgagcata ggcactcacc ttggacatga atgtgcataa ctgcacatgg cccatcccat      7380
ctgaataagg tcctactctc agaccctttt tgcagtacag caggggtgct gatcaccaag      7440
gccccttttc ctggcctgtt atgtgtgtga ttatatttgt tccagttcct gtgtaataga      7500 catgaagcc tcccctgcca cactccaccc ccaatcttcc tttcccttct ggcaggaagt       7560
acccgctcca taagacccctt acatttggac agtcaaggtg cacaattgta tgtgaccaca     7620
accatgcacc ttggacataa atgtgtgtaa ctgcacatgg cccatcccat ctgaataagg      7680
tcctactctc agacccctttt tgcagtacag taggtgtgct gataaccaag gccctcttc     7740 ctggcctgtt aacgtatgtg attatatttg tctgggttcc agtgtataag acatggaagc     7800 ctccccctgcc ccacccccacc ctcaatcttc cttttccttc tggcagggag tgccagctcc   7860
ataagaacct tacatttgga cagtcaaggt gcacaattct aagtgaccgc agccatgcac     7920
cttggtcaat aatgtgtgta actgcacacg gcctatctca tctgaataag gccttactct      7980
cagacccctt tgcagtaca gcaggggtgc tgataaccaa ggcccatttt cctgggcctgt     8040 tatgtgtgtg attatatttg tccaggtttc tgtgtactag acaaggaagc ctcctctgcc     8100
ccatcccatc tacgcataat cttttcttttc ctcccagcag ggagtgctca ctccataaga    8160
cccttacatt tggacaatca aggtgcacaa ttgtaagtga ccacaaccat gcatcttgga     8220
aatttatgtg cataactgca catggcttat cctatttgaa taaagtccta ctctcagacc     8280
ccctttgcag tatagctggg gtgctgatca ctgaggcctc tttgcttggc ttgtctatat     8340
tcttgtgtac tagataaggg caccttctca tggactcccct tgcttttca acaaggagta    8400 cccactactt tttaagattc ttatatttgt ccaaagtaca tggttttaat tgaccacaac     8460 aatgtcccctt ggacattaat gtatgtaatc accacatggt tcatcctaat taaacaaagt    8520
tctaccttct caccctccat ttgcagtata ccagggttgc tgaccccta agtcccctt       8580 tcttggcttg ttgacatgca taattgcatt tatgttggtt cttgtgccct agacaaggat     8640
gccccacctc ttttcaatag tgggtgccca ctccttatga tctttacatt tgaacagtta     8700
atgtgaataa ttgcagttgt ccacaaccct atcacttcta ggaccattat acctcttttg     8760
cattactgtg gggtatactg ttttccctca aggcccctcc tggtgggacta tcaacatata    8820 attgaaattt tctttgtct tgtcagtag attaaggtca taccccatca cctttcctt        8880 gtagtacaac agggtgtcct gatcaaccaa agtcctgttg ttttggactg ttaatatgtg     8940
caattacatt tgctcctgat ctgtgcacta gataaggatc ctacctactt tcttagtgtt    9000
tttagcaggt agtgcccact actcaagact gtcacttgga atgttcatgt gcacaaactc    9060
```

```
aattctctaa gcatgttcct gtaccacctt tgctttagag caggggatg atattcacta    9120 agtgccccctt cttttggact taatatgcat taatgcaatt gtccacctct tcttttagac    9180
taagagttga tctccacata ttccccttgc atcaggggca tgttaattat gaatgaaccc    9240
ttttctttta atattaatgt cataattgta tttgtggacc tgtgtaggag aaaaagaccc    9300
tatgttcctc ccattaccct ttggattgct gctgagaagt gttaactact cataatctca    9360
gctcttggac aattaatagc attaataaca attatcaagg gcactgatca ttagataaga    9420
ctcctgcttc ctcgttgctt acatcggggg tactgaccca ctaaggcccc ttgtactgtt    9480
aatgtgaata tttgcaatta tatatgtctc cttctggtag agtgggatat tatgccctag    9540
tatccccttt gcattactgc aggggctgct gactactcaa aacttctcct gggactgtta    9600
ataggcacaa tggcagttat caatggtttt ctccctccct gaccttgtta agcaagcgcc    9660
ccaccccacc cttagtttcc catggcataa taaagtataa gcattggagt attccatgca    9720
cttgtctatc aaacagtggt ccatactccc aaccccttttg cattgcgcca gtgtgtaaaa    9780
tcacaggtag ccatggtgtc atgctttata tacgaagtct tccctctctc tgccccttgt    9840
gtgcccttgg ccccttttta cagactattg ctcacaatct caggtgtcca tatttgcagc    9900
tattaggtaa gattgtgctg tctccctctt cccttccctc tgccctgccc cttttgcctc    9960
tttgctgggt aatgttgacc agacaaggcc ctttctcttg gacttaaaca attctcagtt    10020
gcactttcct tggtcccacc cattatacat gaaccctct acttcctttc gcattgcttc    10080
tgagtatgct gactacccaa agcccccttct gtgttattaa taaacacagt actgattgtc    10140
ccattttcca gcccatcagt ccaagatctc cctaccactt tggtgtgttg gtgcagtgtt    10200
gactatgaaa agcaggcctg aactaggtgg ataagcctcc actcatttct tttcatttat    10260
taatgatcct agtttcaatt attgtcagat tctggggaca agaaccatcc ttgcccacct    10320
gtgttactgc tttactgtgc aaaatactga aggcaagtca gacccaggga gctggattgc    10380
catcctttat tttgtgtttc cagtgtacac tataaaattg tctccccagg aaggaaggtt    10440
ggcactttct ctgcattctt ctttccagag cagattgcct ggttaagaat ctcttgttgt    10500
cccctttgta tattgttatt gtaaagtgcc aaatgccagg atacagccag aaaaattgct    10560
tattattatt aaaaaaattt ttttaagaaa gacatctgga ttgtagggtg gactcgataa    10620
cctggtcatt attttttga agccaaaata tccatttata ctatgtacct ggtgaccagt    10680
gtctctcatt ttaactgagg gtggtgggtc tgtggataga acactgactc ttgctatttt    10740
aatatcaaag atattctaga gtggaactct taagaccagt atctttgtgt gggctttacc    10800
agcattcact tttagaaaaa ctacctaaat tttataatcc tttaatttct tcatctggag    10860
cacctgcccc tacttatttc aagaagattg cagtaaaacg attaaatgag gaacatatg    10920 cagaggtgct tttaaaaagc atatgccacc tttttatta attattatat aaaatgaagc    10980
atttaattat agtaataatt tgaagtagtt tgaagtacca cactgagtg aggacttaaa    11040 aatgataaga cgagttccct attttataag aaaaataagc caaaattaaa tattcttttg    11100
gatataaatt tcaacagtga gatagctgcc tagtggaaat gaataatatc ccagccacta    11160
gtgtacaggg tgttttgtgg cacaggatta tgtaatatgg aactgctcaa gcaaataact    11220
agtcatcaca acagcagttc tttgtaataa ctgaaaaaga atattgtttc tcggagaagg    11280
atgtcaaaag atcggcccag ctcagggagc agtttgccct actagctcct cggacagctg    11340
taaagaagag tctctggctc tttagaatac tgtaagtact acttcgtagc tattaagtaa    11400
```

```
tcttttttcct attctattttt ctttctctta gatgccacct atagaaaagt cagagggtcc    11460
agtaagtttc tttccttctt cccacctcat ctgcaatata tatatataga gagagaaata    11520
gatacataca tacatgcata aatacacata tgtgagttaa ccagcagaac tgtagaatta    11580
atattgtgga cccagctcta tgctaggtta cactgataac ctgggtagga atgatatcat    11640
cctatataat ttcattcctg agatgatttt atcgttgagg agctaatgtg agcacatttg    11700
aaataacttt agaaaataat aagtgctgtt tgtgtgaat cataagtagt agttttagga    11760
agggaaccca caaggatttg aagttgatag aataaactta aggaagtggg tttgcttttt    11820
ctctttaagc caagatagga ttaatattgc agccatctgg atagtccagt tggtttattt    11880
taatttcatt tgttttttac ctcttttgga gccatggaaa gagatgaaag ggatagagca    11940
tagccattgt gtttggctat ttgcgaaggt tggcaaatta tgattgcta aatctcataa    12000 gcttgagtat tttaaagttc agagattgag ggcataaatc taatacttcg gctccttcca    12060
caattttact acatttctgc ccaagaacag atgaccatgg ataatgcata tcgtagatac    12120 ttttttaagtt tggaaccttt ttgccaagag ggtagtggag aagtgaagtc aaaaccttga    12180
ccttccttgc ctactttatg ctgtagttta tataccttct ttcctcccac ctttcgtaaa    12240
gctaaaagaa gcttagcctc cttaatgttt tccagctgac aaaatattgt ttaacataac    12300
attcgaaact ttttttctgg tgcacattca tgcatcacag caggagcaac aagaaccata    12360
taagtgaact ggcttcactt atagcccgtt ttaattcata tccatatttc ctcagggctt    12420
gtttccatgc ctcccagccc cactccatat gcttaacaac attgtctggc tgactgaggg    12480
ttatatacat catggtcttg aaccttcttg gaaacatggt ctgtgccatt gtttctcaaa    12540
cccaagtaat gcttcatgat gaaacacctt ctaaggaac aaaattttct gagatcctaa    12600
aaaaatgtgt tttgaggaac actgacttaa caaagatatt tgaaatgtaa atatgttttc    12660
caatttcacg ttgtctttgt caaagatgtg ttttatataa cttatgtaga acttggggat    12720
ccattagaat atattcacaa atccccaggg ttatcacccc aatttgagaa accctggtct    12780
atgcttatga aatcttctat tggtaattaa attgtcattc attgtcaaca tacaattata    12840
attattattg gaatttgttt taaatgaatg aatttggagg tgattctgta ccttaagtca    12900
agaggaagga tggcttgatt ttaggtggat tgattatact agatagcatc caaaggtgaa    12960
tcttgaagct gtatttaaat tcattgcttg aaataatttc cacccttaag aaaaatctct    13020
agcaattgta aaagggatg ctctggaaat gtgggcatct tcaaaataga gataattctt    13080
gtgttagttc aacaaatatt attgtaccag gtgctggaat aaatagcaaa accaaagaca    13140
ggatttatat caaggaattt gctttcttat ggaggatgca gaaggaaatc attatggttt    13200
tgggcagaaa tgcttagact ttagtcctgg ctctgagttt ggttcagatc accatcaatc    13260
tgaccatctc gagactgcta gtgaaataag ataggggctt atatcaaata cctaaatccc    13320
tgaaaatgac attttgtgat ttggaaaatt ttcaaaagtc taatgaagga aactttttg    13380 gcatttcttt aaatgattat tgtcatttct tttctgactt ttccctttat aaaaccttaa    13440
catgtaggat tggaggaagt tttctgacca ttttctcata tcctcttca gctttatctt    13500 tctgtaactt ccatttctct agccactctc ctaaattaca gaagactgtg agacccaggg    13560
ctgctgtgat taggcattca taatttcttt tcagggtgtt tgtgccctga ttatcaaatg    13620
tacagcttga agggagttca tgtcttaaag taatgaatta agagttgacc tttgttgact    13680
gctaaaatat tcttatatgt gaaagcatcc tggaaaaata cgttaccagc ttaaagaaa    13740 agaaactaat gattatatct gaactgagct aatgcctctt ctcttccccc aaaccttatc    13800
```

```
agtttggatg gcaaagagta atgatgtgtc agttaaacag agctaatgcc ttcctctgcc    13860
ttgtcttaaa gactggattg ggagaaaatt gatattctca ctaccatatt tgggctgta     13920 ggcaagtagc attttacaca ggtttccttc aaaaatccaa ctcaagttgg agctcatgta    13980
tttaagacat agctggcctg ctgaatttaa caagttaaac ttcagtggcc atgtacagtt    14040
atatatcact atatatatgt gtattaggct gtcgagttgg tcatgttttt gttggtgact    14100
taggctttac ttgatagctc ttccttgacc tttccaaatt gagtactgat acatggagct    14160
tgggcttctt ctgcatctta tacaaatgag tttggtaaag aagcctctcc tttactgttt    14220
tgatgtttat attagaaata acttttgatt attttttttc atgttaggat gagaaactga    14280
aacaaaatgt aaatttgacc ggtgctagac ttcttaaatt atgggtagac ttaaagtatt    14340
attttcctta accaattaga atgctagtct tctagtgttc ccggaaacat gagaggttat    14400
gcagtagacc caagcaatac cctcttatta cataatcaag tgcgtataag aatttaaaaa    14460
tagggatatg actggaacat cactgtactt taccaggtcc cattataaaa ttatctatgt    14520
tactttaccc atagctttga aaactagtgg catagtatat tttatagtat gctgttagtg    14580
tgattggcat tgaacagtga tgggatataa tcactctaca atctatatgt tattaaagtt    14640
ttccagcctt atagatctcc cttgactgaa aattagctac taacttacga cttatttttt    14700
acagcagatt gactaggtct ttccaggaaa tctgttgatg tacaaaaaca aagtttaatt    14760
gctaatgttt ttttaaaaaa taacttttg atattacgga tacctggtta tttgggcctt     14820
gtatatttta acatcaaaat tacctattat aaatccatat aaacagaaaa gaaagagagt    14880
aagtctttag atcagatctg caaacaatga tggtacgtac tgtagaaaaa tctggaacat    14940
agacttacca gttcttaggt tccatttttgc ttgcttttta aaaactgtgt cttataagtc    15000
ttcagcaact ggttgggaga ttttagaaa aaataacctt ttaatgttag aacagtgtag     15060
agatttacag aatgattctg aagatagagt ttctgtgtac ttcacaccca gttttttccca   15120 gtgttaacat tttacattag tttggtacat ttgtcacaac aaaccaatat tgatacatta    15180
ttattaacta gagtccatat tttattcaga tttccttagt ttttccttaa tgttcttttt    15240
gtgttccagg atcccattga agataccacg ctgcatgtgt ccttagtagt catgtctcct    15300
taggctcctc ttggtaatga cagtttctca gactctttgt ttttgatgaa cttcacagtt    15360
ttgaggacta atggtccagt attctataga atgtctctct attggaattt gtctgatgtt    15420
cttctcatga ctagattggg tttatgagtg tttaggagga agaccacaaa ggtagagtgc    15480
cattcttatc acttatcaag agtacatact atcaacatga cttatcactg tttatgttat    15540
ccttaatcac ctgtctgagg tactatttgt caggtttctc cagcgtaaaa ttagtcttta    15600
tttctccatt tccctactat actgttcaca taggaagtca ctatgtgcag ccagcactta    15660
aggaatggga aattaccttc cacctcattg agggcagagt atttacataa attatttgga    15720
attcttttgc acaggatgtc ttttctccac aatgtattgt gtttattcag tcatttatat    15780
cagtatgatc tcagggatat tttatactct gggttataat acagtattac tttattctgt    15840
tgttcaaatt gttccagctt tggccattgg gaggtctttc atttggcttt gatataaccc    15900
catgaatgtg ggttttttgt ttgagcactt tcttattttt ggaactacaa catgcttcag    15960
actcatttgc atatctcctg cctggaccta aaatgatgta tttctgcaag gagccttgat    16020 acttttatt ggagagtaat attagaaatc aagaagtgaa tgctaggtgc gctcattact     16080
actggagtgt cattccttca agaccttttc agttgacaag agcaaggaga tatatatttg    16140
```

```
cattctaacg tgtgtatatg cacatagcta taaatatata taaccatctg tatctatatt    16200
aaactaaatg tgtttatacc tacgtctcca actctaatca ttgccacatg gatcattata    16260
gtctcacctc cttgcttatc tgttacctcc catttctaca gtgagaaacc tggcttggtt    16320
gggaaatttt tctgttaata ttacggtagt gagtgtttga catttgcttc tatggttaag    16380
tttagggaga gtttagctgt agggtattct tgaaactaga aatgacccct ctgccctaaa    16440
tgtttctgcc agttttgaaa cgtaaaatag gttgcagaaa caaactttat cttaagaacc    16500
agaatttact tcaatccaca ttttgacatt gattttcaga ttaaattatt ctgatatcgc    16560
caggtaagct gttccttggg tatgcatttc ttctttccgt tttttttctaa gagctaaagg    16620 accctgagaa cactggaggt gggaaaggaa gggaaaggca tgttcacacg tgggatagga    16680
aaggttcatt tactgacctc cagctagcct tccaaagtgc ctatttaaga cccaaggagt    16740
agatgtcttc cttggcaatt gtaacccaaa tataatttt aacctttcaa ttttagtcaa    16800
gaaagttggt gtgctgttac aaaaagtgcc ctgattaaca gcattgtcat gtgcattgca    16860
tattaatcag caatttaaaa taacatgaaa ttatgttgag tataatttta atattttata    16920
ttagatatta gtttgagaca gtgtttctca agtctgtata ataagtttga tagtagggag    16980
gttttctctc aagaaaagaa ttattcagtg tgcacctaca taatcactgc ttagattcta    17040
caattaatat tttgctatat ttgattaaac gttttctgta aagaaaaat attattatgt    17100 actatttagg tttatgggaa taattgttaa gttaaagtgt atgaacaaac ctggaatgaa    17160
atctgtttgc ctacatctat aatacaacta taaaacatag cagatgtaca aattagtagt    17220
taatagataa ctaaaatgca aatatggcac tactattata gtattatagt ttcttttgag    17280
tggcgtgtct gtaatatcac atgctgtgtt gatgcacttc accaaactgc tgtttttcaaa    17340 ctgctttaaa tcctgccatt atagcacata gcaatgctat ttcactttca tttggcacaa    17400
aacacattta tatattgttt gcttctcttc ttttctgtaa tccccaggca acaaaactag    17460
aacatttgcc actaatctgg caacgtggtc ctatattatg aagtagtcat atagctgatc    17520
taaactatcc ttacagtgaa atgagagtat tgtgaaagtt ttgtagaaag ctccccatat    17580
gtcctgagaa tctatgcaca gaccccacag ttaaaagacc tttgaattgt gggaagacat    17640
gggtttaagt atcacttggt taccttctat ttgtgtaaca ttgaggtagt ttcatcttct    17700
gggttcccag tttccttaga gaatgaaaat gttgaattat gtgatttttt tttttttttg    17760
agacggagtt ttgctctttc gcccaggctg gagtgaagta gcacgatctc gactcactgc    17820
aacctccttc ccccatgatc aagcaattct cctgcctcag cctcccaagt agctgggatt    17880
acaggcaccc gcccccacc cccgccccc agctaatgtt tgtatttta gtacagatgg    17940 agttttgccg tgttggccag gctggtctcg aacttctgac ctcaggtgat ccactcgcct    18000
tggcctccca aagtgctagg attacaggca tgagccactg cgcctggcct atgtgattat    18060
taatatcacg tctagctgtg acaattctgt ctgatgctgg agtatttgaa ccagatggct    18120
ggctgtgcca ctcagttatt ctctccataa gactttgata ttttgttggt ctgcaagatg    18180
acggattctc aaaattcttg tcagtgaata ttgaaccta gtgaaatgta tggttctgta    18240
tcagttccaa aatgtaacca cttttctctag ccttagattc ccagttccaa aatgtaacca    18300
ttttctctag ccttagattc ccgttaaggg aaagggaatg ctctttgagt atgtcatcac    18360
catagtaaca ggcaaaacta gagggctttg atgctaaagc aagatactcc ataaatatgc    18420
ttaagaagac ttggggagac tggaatagtt gttcccttt agatgccagt gtataaatga    18480
atttgagcta ggatccgttt atttaaaatt tctttaggtg tatttgcttg catatggagt    18540
```

```
gcacatttac tctcattaat ggagttttag gaagcagtag agtaaatgca taaacatgta   18600
tgaaccgcca tgtttaactg gaagcctgca tttggaagtc aagtatctaa tcttagatta   18660
aattaggatg gggaaggatg ttggcaagag attttgaagc ttgttctgct tatattgaga   18720
acatcataga acagtttggc cttttttaaag ctagagaata gtgttgaata agtgatgttc   18780
catatattcc tgtttgacat tgacataaag gtttcctcat gatacagtaa tccctgatca   18840
gggatctgga agcctgtatt catttaaggt actcaggttt aacatactgg gtgcttttca   18900
caccatacta tacagtacca tgcaaagtgc tttcaagact gcaaatttgg cttagatccc   18960
ctttagtgag ctcctatgct atagtaaagg tagatagcca attattaaaa acagtcaaga   19020
caattgcacc tctaagcagt agtagcagtt gccacaccac cttgaatctt gaagtatttt   19080
cagcaacagg atgaccatta gccacaaatt tagtgtcagc ccttaaggtc ggtattggtt   19140
tgacccatat tttcatgtag ttcttttttct tcacttgtct aatcttcccg tgtactgcca   19200
gggcttgtca ttagaggact ttagggagac caagcaggct agaaagtaga gacaggagat   19260
acctatgtct aatgcttcag tttatacttc ctaggttttt ttcattgggg tttttgtaac   19320
tcttttggta tcctaccggt gctttggtag cctactgaac cctgtctttc ttcttaagga   19380
cattctgagc atgtgagacc tgaggactgc aaacagctat aagaggctcc aaattaatca   19440
tatctttccc tttgagaatc tggccaagct ccagctaatc tacttggatg ggttgccagc   19500
tatctggaga aaaggtagt ttgggaatt tattgttgta gtgcttctgt ctttggattg   19560
aacttcccac aactctcctt tttaaagcag aacacagctg gcatggtgg ctcctgcttg   19620 taattccagg gctttgggag gttgaggtgg ggggatcact tgaggccagg agttgaagac   19680
ccatgtctct acaataaaat aaaattagtt gggcatggtg gtacgtgcct gtagtcctac   19740
ctactctgga ggctgaggca gcaggattgc ttgagcccag gagttcaagg ctgcagtgag   19800
ccatcattag ccactgcact ccagcctagg tggcagagcg ggacccagtc tcttaaaaag   19860
aaagaaaagc agaacgtgag ccagttttca tcaattccta tacttttct tttgcatgta   19920 cacatacatt ttaactttac ataatgagtt cggcctgttt catttatccc tcagagctgg   19980
gctccagtga ggtctgtaag ggcaagcata cttgatcccc aatgaagaat gagagatgca   20040
aagcactaaa ttatttcttt tctcaccaca cagcaagata gatttaatga acttaacacc   20100
ttttgattag tggcctttta aattattccc actttccttt ggcagatggg tattaagttc   20160
tcaggatttg tttacaaata agactaactt catctgtatt agctcagttt tggtaggcct   20220
aattccatta tcactgccat ttccttgttt taagaaatca aaatttctta gcttgaaaaa   20280
caattgaaat tgttaaaaag tggaatagga gagccccggg ggcctgtata aggaatttac   20340
tgaatccctg gttttctgta ccttgttttt ccttctgcat agatttgctt aactgttttt   20400
gtggcgtgta ttttttttttt ttcgcagttt cgctcttgtt gcccaggctg gagtgcaatg   20460
gcgcaatctc agctcactgc aacctctgtc tcctgggttc aagttattct cctgcctcag   20520
cctctcgagt agctgagatt acaggcatgc gcgaccacgc caggctaatt ttgtattttt   20580
agtagagacg gggtttctcc atgttggtca ggctggtctc aaactcctga cctcaggtga   20640
ttcacccgcc tcgacctccc aaactgctgg gattacaggc gtgagccacc acgcctggcc   20700
agctgttgtt ataactggag ttctatgtgc ttgtgaccat tcttggtttc tccgaatatc   20760
ctagaacttt ggtggcgccc tattatacag gttgttgaag aaatgttacc atgtggattg   20820
agtaggaaac aattctctttt atcttggcaa tattatggca tggcactact taaagtacaa   20880
```

```
attaaaagag ggggatgcta cagaactagc tgacaggcac tttgatagag gtggatttct   20940
cagttcttaa aatagctctt tataaaggaa gccagaggca ttgtggagga gaattcttac   21000
ataactcata gggttagacc acatccgacc ttttctgtgt ggcttcatgg ctctcttggt   21060
tgagaaagca ttagtttctc cttccattag tttcaacctc ttgatttctt gaccccccta   21120
ctatattttg tgctgagaac acaagggtat taacaaccca cattgtagag gatcgctcag   21180
taataaagac tggagaataa aatgcagcat gggaatattg gcaattactc agttctaaat   21240
ttctcttgga aatgagggaa agcatacaga atagagctgg aatgaatagg ataatttttt   21300
ttttttttgc taagttggta gccagaatat aacagctccg cacaactgta aatgtccact   21360
cttcaatcca catgaagaaa agggtaaaaa tatggttgaa ctcaaccact agttgcccat   21420
tagaacagac tttcccagtg tactgcattt caatactttt tcttttatct cttttcagat   21480
cttcctcaga agaataggct tgttgtttta cagtgttagt gatccattcc ctttgacgat   21540
ccctaggtgg agatgggggca tgaggatcct ccaggggaaa agctcactac cactgggcaa   21600
caaccctagg tcaggaggtt ctgtcaagat actttcctgg tcccagatag gaagataaag   21660
tctcaaaaac aaccaccaca cgtcaaggtg cgtaagctgt ccctaaaagc ataataagta   21720
gtcttaattt tgattttgtt ttccagtata cattgcactt agtgtttcac tgaggtcgta   21780
ttcatcatta ttctgcatat gatttggtaa aaacagcttc ctaactaacc tgggaagcaa   21840
ctgggtgtga gattaactgg ttaaagtgat gatgtaaaga gggtagcggg ttgcatgtgt   21900
tcgggtgttt ggagtgggac tatagcacgt ggcagaggct tacagctaag ttgttctttt   21960
aggagaacat ggacaactgt cacatcagtg acattgatca catgggcaaa tcattctgtt   22020
ccatgtggtc cccaaagtct ctcttaaagc cttacagaag aactttgcca atcatttaca   22080
tacttcagga tggcttggga tgccatggtg tataatacaa caagtgagag gtgtgtcttt   22140
ttatgctatg gttgctgatt gatggaagcc gcataaatac aaatggaaac ctgactaaaa   22200
atggcacaaa gttatctgtc atcaggcagg agctaaagaa ccaggaccct acattctcta   22260
ggtcagtgtt gggagaggct gattagcgag tgagaattgg cagataaagg tgaccattcg   22320
gtgcaataaa tcctgaacgt ataggctttg cccagcattc ttcgtaaata gtgggtagct   22380
ataaatttca tgaaatattt tcatgggtaa gaactcttga aatgttataa ttgactagaa   22440
atctctgtag atttagaaat agagagttac taacaaattg ttagaaagtc taggaactag   22500
aaagctaagt tgagagttat ctaggaagat ctatctattg tactcataat ctttagataa   22560
attctcctag ggccagtagt ctatgtgaat tttctttttc ttcttcttct tcttcttttt   22620
ttttgtattt tagctgcaat gttaaacaac ctatgtgaat tttcttattg tgagaatatt   22680
tgccttccag agtgactcac ctttatctca aagagcaata ttgtgagttt tgaaaatgct   22740
gctctaaggc tgtgttttgt tagtcctgag ccaggagact aaagcaaac ttgaggggtc   22800 ttaaaacatc gaagtgagcc ttaaacattg ggaagacctt atgttttttcc ctctcatatc   22860 tattattttt gtgatctcag ttattaatca tttaagggga ctcttttccta gctgattggc   22920 acttaaaaca ggatggaagt cttttttttt tttttttttt ttgagatgga gttttgctct   22980
tgttgcccag gctggagtgc aatggtgcaa tctcagctca ctgcaacctc tgcctcccgg   23040
gttcaagcga ttctcctgcc tcagcctccc aagtagctgg gattacagtc atgcaccacc   23100
acgcccggct aattttgtat ttttaataga cacggtgttt ctccatgttg gtcaggctgg   23160
tctcaaactc ctgacctcag gtgatccgcc cacctcaacc tcccaaagtg ctgggattat   23220
gggcgtgagc caccgcgccc ggcagttctg gtctttaact aaggtataag gctatgactg   23280
```

```
gtagtggtgt ctctagtgac tcatcaagtg atatttggca agacattttc ccatttatgc    23340
cagtttccta ttctgttgaa tgaggaaatt ttctctctaa agacctaaaa gttttgactt    23400
tataggtttc aaagttctgt ggaaacattt tctattgctt attaatttga atcttatgta    23460
actctagcac agtactcaat atttatggca tttacatggt ttatctcatg ttttttata     23520 gctcttcatt gttcctatct gccaaatcat tatacttcct acaagcagtg cagagagctg    23580
agtcttcagc aggtccaaga aatttgaaca cactgaagga agtcagcctt cccacctgaa    23640
gatcaacatg cctggcactc tagcacttga ggatagctga atgaagtaag ttgttgatgt    23700
tgcagtcctg tgaggatcac ttcagaactg ttataacagc tgttttttgg gagctggtgt    23760
tggatggggt gtgttggtct aatgtgaagt ggggctaaat gtgagatgga aagatgacca    23820
gtcttccata ttactgactg ggttcactga agcaactcaa agacattatg gtcttcttac    23880
cagttgtatc acagaagaat ttagcctttg cttgtgtgtt ctatgtcttc actgtatagg    23940
ccctctgtca ttcttagagc cttaaacgtt gagaagctta aaacaccatt tctgctttct    24000
gctgaaaggg taaccctttc tcatctccgt ttgtgagaga ctctgtcgtc agttaagatt    24060
agtgtaaaaa gaaaactaaa ctctgaagta gccattataa aagtgtgaga atgaagtcag    24120
ttttctaaag agttggggaa aggtgatgct aaaggagggg attgagcaag tcctatcaaa    24180 gagccttta tgaaaatact tagtcatctg tgacatccca tttggctctt ccagaaatcc    24240
tagtaaatag ttgtaacagg atgttaagag gcatacattg tgtgttttaa atcctctgct    24300
actcattagg tatatgacct ttgacaactt aaagtctcta gacttctctg tttgtgaggg    24360
ttaaatgaaa tcatgtatgt aaagtgctca cctattgcag tgcctggcac atgtcaagta    24420
aaaggtaacc caagaagact cataagttca tttcccacaa tataagtgac cactagcact    24480
atcaggtagc aggcagagtt ggcatgcttt ggttctatgt aagaaatccc taaggtaaaa    24540
gtttataaat agaagagcat ctgtgttggt attggtggtt gttattattg tagtactata    24600
agtagtattc gtagtaacaa tagtttatta taattactaa tgacacttt tgattttttt    24660 tatctttctg tgatgctttt catgcctctt gtgcccctca ctgtatcttg cctcttctac    24720
tacttacttc ctctgaatgt ctgcctttgc ttatctcttg cactcaagtg tgtatttctt    24780
tgtctctttc tttcttgtct ttgctctttg ttctctatct aaagtgtgtc ttacccattt    24840
ccatgtttct cttgctaatt tctttcgtgt gtgcctttgc ctcatttct cttttgttc     24900 acaagagtgg tctgtgtctt gtcttagaca tatctctcat ttttcatttt gttgctattt    24960
ctctttgctc tcctagatgt ggctcttctt tcacgcttta tttcatgtct cctttttggg    25020
tcacatgctg tgtgcttttt gtccttttct tgttctgtct acctctcctt tctctgccta    25080
cctctctttt ctctttgtga actgtgatta tttgttaccc cttcccctc tcgttcgttt     25140 taaatttcac cttttttctg agtctggcct cctttctgct gtttctactt tttatctcac    25200
atttctcatt tctgcatttc ctttctgcct ctcttgggct attctctctc tcctcccctg    25260
cgtgcctcag catctcttgc tgtttgtgat tttctatttc agtattaatc tctgttggct    25320
tgtatttgtt ctctgcttct tcccttctca ctcacctttg agtatttcag cctcttcatg    25380
aatctatctc cctctctttg atttcatgta atctctcctt aaatatttct ttgcatatgt    25440
gggcaagtgt acgtgtgtgt gtgtcatgtg tggcagaggg gcttcctaac ccctgcctga    25500
taggtgcaga acgtcggcta tcagagcaag cattgtggag cggttcctta tgccaggctg    25560
ccatgtgaga tgatccaaga ccaaaacaag gccctagact gcagtaaaac ccagaactca    25620
```

```
agtagggcag aaggtggaag gctcatatgg atagaaggcc caaagtataa gacagatggt    25680
ttgagacttg agacccgagg actaagatgg aaagcccatg ttccaagata gatagaagcc    25740
tcaggcctga aaccaacaaa agcctcaaga gccaagaaaa cagagggtgg cctgaattgg    25800
accgaaggcc tgagttggat ggaagtctca aggcttgagt tagaagtctt aagacctggg    25860
acaggacaca tggaaggcct aagaactgag acttgtgaca caaggccaac gacctaagat    25920
tagcccaggg ttgtagctgg aagacctaca acccaaggat ggaaggcccc tgtcacaaag    25980
cctacctaga tggatagagg acccaagcga aaaaggtatc tcaagactaa cggccggaat    26040
ctggaggccc atgacccaga acccaggaag gatagaagct tgaagacctg ggaaatccc    26100 aagatgagaa ccctaaaccc tacctctttt ctattgttta cacttcttac tcttagatat    26160
ttccagttct cctgtttatc tttaagcctg attcttttga gatgtacttt ttgatgttgc    26220
cggttacctt tagattgaca gtattatgcc tgggccagtc ttgagccagc tttaaatcac    26280
agcttttacc tatttgttag gctatagtgt tttgtaaact tctgtttcta ttcacatctt    26340
ctccacttga gagagacacc aaaatccagt cagtatctaa tctggctttt gttaacttcc    26400
ctcaggagca acattcata taggtgatac tgtatttcag tcctttcttt tgacccaga    26460 agccctagac tgagaagata aatggtcag gttgttgggg aaaaaaagt gccaggctct    26520 ctagagaaaa atgtgaagag atgctccagg ccaatgagaa gaattagaca agaaatacac    26580
agatgtgcca gacttctgag aagcacctgc cagcaacagc ttccttcttt gagcttaggt    26640
gagcaggatt ctggggtttg ggatttctag tgatggttat ggaaagggtg actgtgcctg    26700
ggacaaagcg aggtcccaag gggacagcct gaactccctg ctcatagtag tggccaaata    26760
atttggtgga ctgtgccaac gctactcctg ggtttaatac ccatctctag gcttaaagat    26820
gagagaacct gggactgttg agcatgttta atactttcct tgattttttt cttcctgttt    26880
atgtgggaag ttgatttaaa tgactgataa tgtgtatgaa agcactgtaa aacataagag    26940
aaaaaccaat tagtgtattg gcaatcatgc agttaacatt tgaaagtgca gtgtaaattg    27000
tgaagcatta tgtaaatcag gggtccacag ttttctgta aggggtcaaa tcataaatac    27060
tttagactgt gggccatatg gtttctgtta catatttgtt ttttaaacaa cgttttttata    27120 aggtcaaaat cattcttagt ttttgagcca attggatttg gcctgctgtt catagcttac    27180 cacccctga tgtattattt gttattcaga gaaaatttct gaatactact agtttccttt    27240
tctgtgcctg tccctgtgct aggcactaaa aatgcaatga ttattgatat ctaggtgacc    27300
tgaaaaaaaa tagtgaatgt gctttgtaaa ctgtaaagca cttgtattct actgtgataa    27360
gcgttgtgga tacaaagaaa ggagcaagca taaaaagtg ctctttcaaa aggatatagt    27420
actatgcaga cacaaggaat tgtttgataa atgaataaat tatatgtata tttgaggcca    27480
atttgtgttt gctgctctgg taattttgag taaaaatgca gtattccagg tatcagaaac    27540
gaaaacacat ggaaactgct tttaaacttt aaaatatact gaaaacataa gggactaagc    27600
ttgttgtggt cacctataat gtgccagata ccatgctggg tgctagagct accaaagggg    27660
gaaaagtatt ctcatagaac aaaaatttc agaaaggtgc atattaaagt gctttgtaaa    27720
ctaaagcatg atacaaatgt caatgggcta catatttatg aatgaatgaa tggatgaatg    27780
aatattaagt gcctcttaca taccagctat tttgggtact gtaaaataca agattaattc    27840
tcctatgtaa taagaggaaa gtttatcctc tatactattc agatgtaagg aatgatatat    27900
tgcttaattt taaacaatca agactttact ggtgaggtta agttaaatta ttactgatac    27960 attttttccag gtaaccagga aagagctagt atgaggaaat gaagtaatag atgtgagatc    28020
```

```
cagaccgaaa gtcacttaat tcagcttgcg aatgtgcttt ctaaattata aagcacttgt   28080
aaatgaaaaa tttgatgctt tctgtatgaa taaaactttc tgtaagctag gtattgtctc   28140
tacaaaattc tcattgtata gttaaaccac agtgagaagg gttctataag tagttataca   28200
aaccaagggt ttaaatacct gttaaataga tcaattttga ttgcctacta tgtgaactca   28260
ctgttaaagg cactgaaaat ttatcatatt tcatttagcc acagccaaaa ataaggcaat   28320
acctatgtta gcattttgtg aactctaagg caccatataa atgtaactgt tgattttctc   28380
acttggtgct gggtactagg tttataaaat tgtatgatag ttattatatt gtgcaaataa   28440
agtaggaaaa tttgaataac aatgattatc ttttgaatac gcatacgcaa gggattggtt   28500
gtctgaagaa tgccactata gtagttatct attgtgtgcc aatctcattg ctaggcattg   28560
gggatgcaaa gataaaccat ctttattgtg tcttgggtag cagaagaaaa tatgtgtaaa   28620
atcaatttat aatttgtaaa ctgccaccca tatataagct atatctgctg aatgatcatt   28680
gattactctt atccttagag ataacaactg ggggcacaaa catttattat cattattgaa   28740
cctacaacag agatctatgt gtagatttac aaagcctaca gttctataca gataggaatg   28800
aactattggc ttactgaatg gtgattactt tctgtggggc tcggaactac atgccctagg   28860
atataaaaat gatgttatca ttatagagtg ctcacagaag gaaatgaagt aatataggtg   28920
tgagatccag accaaaagtc atttaacaag tttattcagt gatgaaaaca tgggacaaat   28980
ggactaatat aaggcagtgt actaagctga gtagagagat aaagtcctgt ccagaagata   29040
catgcttcct ggcctgattg aggagatgga aaattttgc aaaaaacaag gtgttgtggt   29100
cttccatcca gtttcttaag tgctgatgat aaaagtgaat tagacccacc ttgacctggc   29160
ctacagaagt aaaggagtaa aaataaatgc ctcaggcgtg cttttttgatt catttgataa   29220 acaaagcatc ttttatgtgg aatataccat tctgggtcct gaggataaga gagatgaggg   29280
cattagatca ctgacagctg aagatagaag aacatctttg gtttgattgt ttaaataata   29340
tttcaatgcc tattctctgc aaggtactat gttttcgtaaa ttaaataggt ctggcccaga   29400
agacccactc aattgccttt gagattaaaa aaaaaaaaa aagaaagaa aaatgcaagt   29460 ttctttcaaa ataagagac atttttccta gtttcaggaa tcccccaaat cacttcctca   29520
ttggcttagt ttaaagccag gagactgata aaagggctca gggtttgttc tttaattcat   29580
taactaaaca ttctgcttt attacagtta aatggttcaa gatgtaacaa ctagttttaa   29640
aggtatttgc tcattggtct ggcttagaga caggaagaca tatgagcaat aaaaaaaaga   29700
ttcttttgca tttaccaatt tagtaaaaat ttattaaaac tgaataaagt gctgttctta   29760
agtgcttgaa agacgtaaac caaagtgcac tttatctcat ttatcttatg gtggaaacac   29820
aggaacaaat tctctaagag actgtgtttc tttagttgag aagaaacttc attgagtagc   29880
tgtgatatgt tcgatactaa ggaaaaacta aacagatcac ctttgacatg cgttgtagag   29940
tgggaataag agagggcttt ttatttttc gttcatacga gtattgatga agatgatact   30000
aaatgctaaa tgaaatatat ctgctccaaa aggcatttat tctgacttgg agatgcaaca   30060
aaaacacaaa aatggaatga agtgatactc ttcatcaaac agaagtgact gttatctcaa   30120
ccattttgtt aaatcctaaa cagaaaacaa aaaaatcat gacgaaaaga cacttgctta   30180
ttaattggct tggaaagtag aatataggag aaaggttact gtttattttt tttcatgtat   30240
tcattcattc tacaaatata ttcgggtgcc aataggtact tggtataagg ttttggccc   30300 cagagacatg ggaaaaaaat gcatgccttc ccagagaatg cctaatactt tccttttggc   30360
```

```
ttgttttctt gttaggggca tggcttagtc cctaaataac attgtgtggt ttaattccta    30420
ctccgtatct cttctaccac tctggccact acgataagca ggtagctggg ttttgtagtg    30480
agcttgctcc ttaagttaca ggaactctcc ttataataga cacttcattt tcctagtcca    30540
tccctcatga aaaatgactg accactgctg ggcagcagga gggatgatga ccaactaatt    30600
cccaaacccc agtctcattg gtaccagcct tggggaacca cctacacttg agccacaatt    30660
ggttttgaag tgcatttaca aggtttgtct attttcagtt cttactttt tacatgctga     30720 cacatacata cactgcctaa atagatctct ttcagaaaca atcctcagat aacgcatagc    30780
aaaatggaga tggagacatg atttctcatg caacagcttc tctaattata ccttagaaat    30840
gttctccttt ttatcatcaa atctgctcaa gaagggcttt ttatagtaga ataatatcag    30900
tggatgaaaa cagcttaaca ttttaccatg cttaagtttt aagaataaaa taaaaattgg    30960
aaataattgg ccaaaattga aaggaaaaat ttttttaaaa tttctctaaa tgtaggcctg    31020
gctgggcttt gaccttttcc gttttttaaat cactcacaga gggtgggaca ggaggaagag   31080
tgaaggaaaa ggtcaaacct gttttaaggg caacctgcct ttgttctgaa ttggtcttaa    31140
gaacattacc agctccaggt ttaaattgtt cagtttcatg cagttccaat agctgatcat    31200
tgttgagatg aggacaaaat cctttgtcct cactagtttg ctttacattt ttgaaaagta    31260
ttatttttgt ccaagtgctt atcaactaaa ccttgtgtta ggtaagaatg gaatttatta    31320
agtgaatcag tgtgaccctt cttgtcataa gattatctta aagctgaagc caaaatatgc    31380
ttcaaaagaa gaggacttta ttgttcattg tagttcatac attcaaagca tctgaactgt    31440
agtttctata gcaagccaat tacatccata agtggagaag gaaatagata aatgtcaaag    31500
tatgattggt ggagggagca aggttgaaga taatctgggg ttgaaatttt ctagttttca    31560
ttctgtacat ttttagttag acatcagatt tgaaatatta atgtttacct ttcaatgtgt    31620
ggtatcagct ggactcagta acacccttt cttcagctgg ggatggggaa tggattattg     31680
gaaaatggaa agaagaaagt aactaaaagc cttcctttca cagtttctgg catcactacc    31740
actactgatt aaacaagaat aagagaacat tttatcatca tctgctttat tcacataaat    31800
gaagttgtga tgaataaatc tgcttttatg cagacacaag gaattaagtg gcttcgtcat    31860
tgtccttcta cctcaaagat aatttattcc aaaagctaag ataaatggaa gactcttgaa    31920
cttgtgaact gatgtgaaat gcagaatctc ttttgagtct ttgctgtttg gaagattgaa    31980
aaatattgtt cagcatgggt gaccaccaga aagtaatctt aagccatcta gatgtcacaa    32040
ttgaaacaaa ctggggagtt ggttgctatt gtaaaataaa atatactgtt ttga          32094
```

NUCLEIC ACID SILENCING SEQUENCES

CROSS-REFERENCE TO RELATED APPLICATIONS

This application is a continuation of U.S. application Ser. No. 14/045,057, filed on Oct. 3, 2013, now U.S. Pat. No. 9,297,023, issued on Mar. 29, 2016, which is a continuation of U.S. application Ser. No. 13/483,240, filed on May 30, 2012, now U.S. Pat. No. 8,574,900, issued on Nov. 5, 2013, which is a continuation of U.S. application Ser. No. 12/512,964, filed on Jul. 30, 2009, now U.S. Pat. No. 8,212,019, issued on Jul. 3, 2012, which claims the benefit of the filing date of U.S. Application No. 61/084,918, filed on Jul. 30, 2008, each of which is incorporated herein by reference in its entirety.

STATEMENT REGARDING FEDERALLY SPONSORED RESEARCH OR DEVELOPMENT

This invention was made with government support under Grant Nos. GM053234, GM068138, HD007439, and GM096400 awarded by the National Institutes of Health. The U.S. Government has certain rights in the invention.

TECHNICAL FIELD

This invention relates to compositions and methods for silencing gene expression from a whole chromosome or chromosome segment, and more particularly to the use of an Xist gene or other chromosomal silencing RNA to silence expression from trisomic, translocated, duplicated, or partially duplicated genomic sequences.

BACKGROUND

Naturally occurring chromosomal imbalances are an exceptionally important clinical problem, in part because they are extremely common. Almost 1% of all live births and a much higher percentage of conceptions are affected. Many of the abnormalities involve "extra" chromosomal material, and many of these are so deleterious that they cause spontaneous abortion. Trisomies, in which the fetus carries three of a given chromosome rather than a pair, are usually lethal. Some are not; trisomy 13 (Patau syndrome), trisomy 18 (Edward syndrome), trisomy 21 (Down syndrome), triple-X syndrome, as well as duplications of the X and Y chromosomes (e.g., XXY and XYY) are seen in live births, although babies born with Patau syndrome or Edward syndrome usually do not live more than a year or two.

Down syndrome is extremely common relative to other severe genetic disorders. In the United States alone, over 350,000 people are living with the severe handicaps typical of Down syndrome, and there are millions of affected people around the world. Although Down syndrome children are often happy and highly loved, their disorder greatly impacts them, their entire families, and society. Mental retardation, with poor verbal functioning, is the most debilitating outcome, but there are also other medical issues, including much greater risks of early onset Alzheimer's disease, leukemia, and cardiac defects. Because Down syndrome individuals often are at or just below the threshold of independent functioning, even small increases in function could have significant positive consequences for them and their families.

Although the incidence of Down syndrome increases with the mother's age, 80% of Down syndrome babies are born to women under 35 who are not currently subject to prenatal screening. Upon birth of the Down syndrome baby, the whole family is faced with the enormous challenges associated with caring for and nurturing such a child. For older mothers who do have pre-natal screening, the parents are faced with the heart-wrenching decision of birthing a mentally retarded child or terminating the pregnancy, with no hope of systemic therapy. We believe that whole chromosome therapy would result in a paradigm shift in the minds of many scientists, families, and clinicians, who currently presume that gene therapy for this multi-gene disorder, with such pleiotropic effects, is just not possible.

SUMMARY

The present invention features compositions and methods for introducing, into cells, nucleic acids whose expression results in chromosomal silencing. The nucleic acids are targeted to specific chromosomal regions where they subsequently reduce the expression of deleterious genes, or cause the death of deleterious cells. Where the nucleic acid sequence is a silencing sequence, it may encode an Xist RNA or other non-coding, silencing RNA. Accordingly, the present invention features nucleic acid constructs that include a transgene (e.g., a silencing sequence encoding an Xist RNA or other non-coding RNA that silences a segment of a chromosome); first and second sequences that direct insertion of the silencing sequence into a targeted chromosome; and, optionally, a selectable marker. Below, we may refer to the first and second sequences that direct insertion of the silencing sequence into a targeted chromosome as "first and second targeting elements." These sequences or elements can be readily selected and inserted into the nucleic acid constructs using methods well known in the art.

In the present application, we use the term "Xist" to refer to an Xist gene or the encoded Xist RNA regardless of the origin of the sequence. For example, the present compositions can include, and the present methods can be carried out with, an Xist gene encoding an Xist RNA from humans or another mammal (e.g., a rodent such as a mouse, dog, cat, cow, horse, sheep, goat, or another mammalian or non-mammalian animal). We mention this as the scientific literature has adopted a loose convention whereby the term is fully capitalized (XIST) when referring to a human sequence but not fully capitalized (Xist) when referring to the murine sequence. That convention is not used here, and we wish to make clear that human and non-human sequences may be used as described herein.

The "silencing sequence" is a nucleotide sequence that encodes an RNA that silences a chromosome or a segment or region thereof. While the invention is not limited to the use of silencing sequences that work by any particular molecular mechanism, silencing sequences are believed to encode RNA that binds across the chromosome or chromosome segment and induces repressive changes to chromatin that silence gene expression at the level of transcription. The silencing sequence can include, but is not limited to, a naturally occurring DNA sequence, and "silencing" is a term of art that is understood to refer to a significant reduction in the level of transcription of a gene within the silenced or targeted region of a chromosome.

The silencing sequence can be a full-length Xist gene sequence, a sequence encoding another full-length silencing RNA (examples of which are provided below), or any biologically active fragment or other biologically active variant thereof. The sequence is "biologically active" where its activity is sufficient to effect a therapeutically beneficial outcome. The level of activity of a biologically active fragment or other variant may vary so long as a useful chromosomal silencing RNA is produced. Xist RNA is referred to as a chromosomal silencing RNA because it silences by binding across the chromosome or chromosome segment, and therefore silences at the level of transcription, by inducing repressive changes to chromatin. While Xist RNA is a well studied example of a chromosomal silencing RNA, other non-coding RNAs can silence specific clusters of imprinted genes or segments of a chromosome. These other chromosomal silencing RNAs include Air RNA, HOTAIR RNA, and Kcnq1ot1 RNA (see Goodrich and Kugel, *Crit. Rev. Biochem. and Mol. Biol.* 44:3-15, 2009), any of which can be formulated and used as described herein for Xist. Other intergenic noncoding RNAs, which may be useful in the present nucleic acid constructs and the silencing methods described herein are described by Khalil et al. (*Proc. Natl. Acad. Sci. USA* 106:11675-11680, 2009).

The silencing sequence can exclude one or more introns (wholly or partially) or one or more exons (wholly or partially). However, the silencing sequence cannot exclude all exons. For example, the silencing sequence can be an Xist gene sequence exclusive of one or more introns or one or more exons (but not all exons). For example, the silencing sequence can include about 6 kb to about 10 kb of exon 1 of an Xist gene sequence (e.g., about 6-7 kb, 7-8 kb, 8-9 kb, 6.5-8.5 kb, or about 7.5 kb). More specifically, the silencing sequence can be or can include the Xist cDNA sequence having accession number M97168 or a biologically active fragment or other variant thereof (SEQ ID NO:1).

The silencing sequence can be a mammalian sequence (e.g., a human sequence) and can further include a regulatory sequence (e.g., a regulatory sequence that promotes expression of the Xist RNA). More specifically, the regulatory sequence can include a promoter, which may be constitutively active, inducible, tissue-specific, or a developmental stage-specific promoter. Enhancers and polyadenylation sequences can also be included.

The targeted chromosome can be any autosome or an X or Y chromosome. For example, the targeted chromosome can be chromosome 13, chromosome 18, or chromosome 21. The targeted chromosome can be the third chromosome within a trisomic cell or any region of a chromosome that is aberrant (e.g., a gene or genetic sequence that is duplicated, partially duplicated and/or translocated).

Numerous selectable markers can be incorporated in the nucleic acid constructs. These markers are discussed further below and many such markers will be known to one of ordinary skill in the art. Sequences including a selectable marker can, for example, upon transcription and translation, confer resistance to a toxin or encode proteins that produce an observable characteristic. Thus, expression of the selectable marker sequence allows one to distinguish or "select" genetically modified cells from non-modified cells.

Numerous vectors are also known in the art, and any vector (including viral and non-viral vectors) can be used to deliver the present nucleic acids to a patient or a cell in culture. Accordingly, the invention features vectors and isolated or cultured cells that include any of the nucleic acid constructs described herein.

In another embodiment, the invention features compositions (e.g., pharmaceutically acceptable compositions) that include the nucleic acid constructs or vectors described above (and elsewhere herein) and, alternatively or in addition, a vector that facilitates delivery of the transgene to a cell and/or incorporation of the transgene into the targeted chromosome. Thus, the invention encompasses pharmaceutically acceptable compositions that include nucleic acid constructs carrying a transgene (e.g., a silencing sequence), first and second sequences that direct insertion of the silencing sequence into a targeted chromosome and, optionally, a selectable marker. The targeted integration may be facilitated by inclusion in the construct of sequences homologous to the site of desired chromosomal integration (i.e., the first and second sequences or targeting elements), coupled with the transgene (e.g., sequence encoding Xist RNA or other chromatin-associated silencing RNA).

As noted, the invention features compositions that also include vectors that facilitate delivery of the transgene. Well established targeting methods that rely on homologous recombination can be made more efficient by use of zinc finger nucleases to direct integration at specific sites. Thus, the present compositions can include a cleavage vector comprising a sequence encoding a first chimeric zinc finger nuclease (ZFN) or an adeno associated virus, which can specifically integrate the transgene and deliver it to cells. We describe the ZFNs as "chimeric" as they include at least one zinc finger DNA binding domain effectively linked to at least one nuclease capable of cleaving DNA. Ordinarily, cleavage by a ZFN at a target locus results in a double stranded break (DSB) at that locus.

Various combinations of the constructs and vectors described herein can also be formulated as pharmaceutical compositions. For example, the present compositions can include an adeno associated virus into which a silencing sequence has been inserted or a combination of (a) a nucleic acid construct or vector that silences a targeted chromosomal region or induces cell death following targeted chromosomal integration and (b) a cleavage vector encoding a chimeric ZFN.

The cleavage vector can include more than one chimeric ZFN, any of which can include a DNA binding domain and a cleavage domain. The DNA binding domain binds a genomic sequence that is present in each of the two strands of the targeted chromosome such that the cleavage domain generates a double stranded break in the targeted chromosome at a site into which the first and second sequences will direct insertion of the silencing sequence.

The same cleavage vector that encodes a first chimeric ZFN can include one or more additional sequences encoding one or more additional chimeric ZFNs (e.g., two, three, four, or more ZFNs). Alternatively, additional chimeric ZFNs can be carried on a separate vector. The second and any subsequent chimeric ZFNs can include a DNA binding domain and a cleavage domain. The first chimeric ZFN and the second chimeric ZFN bind, respectively, to distinct sequences in each of the two strands of the targeted chromosome such that the respective cleavage domains generate a double stranded break in the targeted chromosome at a site into which the first and second sequences within the nucleic acid construct will direct insertion of the silencing sequence (or other sequence (e.g., a sequence that causes cell death)). As when the nucleic acid constructs or vectors, including adeno associated vectors, are used alone, the ZFNs can target an autosome. For example, ZFNs can target chromosome 13, chromosome 18, or chromosome 21.

Also within the scope of the invention are RNAs and proteins encoded by the cleavage vector and compositions that include them (e.g., lyophilized preparations or solutions, including pharmaceutically acceptable solutions or other pharmaceutical formulations).

In another embodiment, the invention features cells that include the nucleic acid constructs, vectors (e.g., an adeno associated vector), and compositions described herein. The cell can be isolated in the sense that it can be a cell within an environment other than that in which it normally resides (e.g., the cell can be one that is removed from the organism in which it originated). The cell can be a germ cell, a stem cell (e.g., an embryonic stem cell, an adult stem cell, or an induced pluripotent stem cell (iPS cell or IPSC)), or a precursor cell. Where adult stem cells are used, the cell can be a hematopoietic stem cell, a cardiac muscle stem cell, a mesenchymal stem cell, or a neural stem cell. The cell can also be a differentiated cell (e.g., a fibroblast or neuron).

The methods of the invention can be used to treat patients who have a birth defect, genetic disease, or cancer associated with a genetic aberration (e.g., a trisomy, partial duplication of a chromosomal region, translocation, or ring X-chromosome). Any of the methods can include the step of identifying a patient in need of treatment; any of the patients can be human; and any of the methods can be carried out by either administering the present compositions to the patient or removing cells from the patient, treating the cells, and "readministering" those cells. For example, the invention features methods of treating a genetic disorder associated with a trisomic chromosome by identifying a patient in need of treatment; and administering to the patient a nucleic acid construct, vector, and/or cleavage vector as described herein. The targeted chromosome can be the trisomic chromosome, and the amount of the construct or vector administered will be an amount sufficient to improve a condition associated with the disorder. Where cells are harvested from a patient to treat a condition or disorder described herein (or an associated symptom), the methods can include the steps of identifying a patient in need of treatment; harvesting cells from the patient; transfecting the cells with one or more of the types of constructs and/or vectors described herein; and administering to the patient a sufficient number of the transfected cells to treat the condition or improve a condition or symptom associated with the disorder. The symptoms associated with many birth defects and other conditions are well known. For example, individuals having Down Syndrome often experience mental retardation, hypotonia, cardiac defects, Alzheimer's Disease, hematological abnormalities and leukemia (see Antonarakis and Epstein, *Trends Mol. Med.* 12:473-479, 2006). As noted above, treatment can also be carried out in vivo by administering present compositions to the patient via pharmaceutically acceptable compositions.

The cells can include differentiated cells (e.g., white blood cells or fibroblasts) and/or undifferentiated cells (e.g., stem cells or precursor cells). The cells can also be differentiated cells that are induced, ex vivo, into iPS cells, or multi-potent stem cells or stem cells of particular lineage, such as neural stem cells. The condition can be a neurological or blood disorder such as Alzheimer's Disease and leukemia, respectively, or a muscular defect, including defects of the heart. Where the condition is myelodysplastic disease which leads to leukemia, it can be an acute lymphocytic leukemia, an acute myelogenous leukemia, or an acute megakaryoblastic leukemia.

In any of the present methods, cells can be transfected with a cleavage vector that includes a sequence encoding a first chimeric zinc finger nuclease (ZFN) having a DNA binding domain and a cleavage domain. As in other embodiments, the DNA binding domain binds a genomic sequence that is present in each of the two strands of the targeted chromosome such that the cleavage domain generates a double stranded break in the targeted chromosome at a site into which the first and second sequences will direct insertion of the silencing sequence or other therapeutically useful sequence (e.g., a toxin or pro-apoptotic protein). Where desirable, the transgene (e.g., a silencing sequence encoding an Xist RNA) can be targeted to a polymorphic sequence that is present in just one chromosome (e.g., one of a set of trisomic chromosomes). Additionally, integration of the Xist transgene can be targeted so as to directly disrupt a particularly deleterious gene, such as the APP gene, over-expression of which leads to the exceptionally high rate and early onset of Alzheimer's Disease among Down Syndrome individuals.

The invention also includes compositions and methods for the silencing of a duplicated genomic region or trisomic chromosome using an approach of random transgene integration followed by cell selection, where the silencing of the trisomic chromosomal material provides a significant selective advantage as compared to silencing of other disomic chromosomes. As a result, patient cells in which the deleterious extra chromosomal material has been silenced by a large non-coding RNA may have a selective advantage; thus, even where Xist transgenes have been inserted at random into the genome of patient cells, cells in which the trisomic chromosome has been silenced may be selected for over those cells in which a disomic chromosome has been silenced (since the latter would generate a functional monosomy that is likely lethal to the cell). In the case of translocated chromosomes, targeting of the transgene can be directed to the unique site generated at the translocation junction, to selectively silence that abnormal chromosome, or to introduce a sequence encoding a toxin, pro-apoptotic protein, or other factor that results in cell death of deleterious cells. For example, using the present methods, one can introduce a sequence encoding a toxin, pro-apoptotic protein, or other factor that results in cell death into a translocated chromosome associated with cancer. This approach can be extended to silencing of duplicated regions of specific chromosomes that are associated with genetic conditions, such as duplication of segments of Chromosome 15q11-13 in Autism. This duplication, which is thought to be the most frequent cytogenetic abnormality in autism, can be targeted by the present methods and is described further in Nakatani et al. (*Cell* 137:1236-1246, 2009). This approach can also be extended to silencing the inappropriate expression of imprinted regions in genetic disease, as in Prader-Willi/Angelman syndrome, also on Chr 15 and associated with autism.

To illustrate a particular application, Xist mediated chromosomal therapy could be used to ameliorate transient myeloproliferative disorder (TMD) in Down Syndrome children and possibly prevent the later development of acute leukemia. Successful bone marrow transplants for diseases like leukemia depend upon immune compatibility, to avoid Graft versus Host Disease (GVHD). To avoid graft rejection, the patient's own cells can be used and transgenically modified prior to transplant. There are two scenarios to acquire and modify stem cells for bone marrow transplant. In the first, the patient's own bone marrow stem cells can be obtained and an Xist transgene can be introduced and targeted to chromosome 21. When Xist expression silences the trisomic chromosome, these cells can then be transplanted back into the patient following standard bone transplant procedures following the destruction of the patient's bone marrow using irritation. Alternatively modified patient bone marrow cells can be transplanted without first irradiating the patient to destroy the unmodified bone marrow. This would produce a situation where the patient's bone marrow would be mosaic for trisomy 21 (a mixture of modified and unmodified cells). We expect that the modified cells would have a growth advantage over the non-modified fully trisomic cells, and the modified cells would eventually out grow the "diseased" cells (see Douillard-Guilloux et al., *J. Gene Med.* 11:279-287, 2009). In the second approach, the patient's fibroblast (skin) cells can be used to produce iPS cells, into which a transgenic Xist gene is inserted and targeted to chromosome 21. IPS cells that silence one of the three trisomic chromosomes will then be differentiated into adult hemopoietic stem cells and introduced back into the patient as stated above.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 6A-E are a series of five contiguous panels showing the complete exon sequence of the *Homo sapiens* X (inactive)-specific transcript (Xist), GenBank Accession No. M97168.1, SEQ ID NO:1.

FIGS. 7A-J are a series of 10 contiguous panels showing the *Homo sapiens* DNA sequence from clone RP13-216E22 on chromosome Xq13.1-21.1 with the X (inactive)-specific transcript (non-protein coding) (Xist), non-coding RNA, GenBank Accession No. AL353804.22, SEQ ID NO:2.

DETAILED DESCRIPTION

Down Syndrome, caused by trisomy of chromosome 21, is the leading cause of mental retardation in newborns, impacting one in every 600-700 live births in the U.S. and across the world. Many families with Down Syndrome children find them loving, happy children, but they are challenged with mild to moderate mental retardation and frequently have a number of medical conditions requiring treatment or surgery. Despite the enormous clinical importance of Down Syndrome and related chromosomal imbalances, there has been little hope or effort for gene therapy in Down Syndrome. Historically, devising therapeutic strategies for trisomies has been particularly challenging because more is involved than a single defective gene or even several defective genes. Down syndrome, for example, involves a quantitative imbalance in tens or hundreds of genes across a 50 Mb chromosome, the most important of which are still not yet well understood (Antonarakis and Epstein, *Trends Mol. Med.* 12:473-479, 2006). Thus, unlike other genetic diseases in which silencing of an individual gene might produce an effective therapy, genetic therapy for trisomies such as Down syndrome is much more challenging. This is because chromosomal trisomies (and segmental duplications or translocations) involve the over-expression of potentially hundreds of genes across a ~50 Mb or larger chromosome, rendering ineffective standard approaches to gene therapy which treat single gene defects.

This invention makes possible an approach to "chromosome therapy" for trisomies or segmental duplications by reducing the challenge of individually correcting over-expression of tens or hundreds of genes, to the much more tractable approach of introducing just one gene, for example Xist, which then silences the whole chromosome.

Figure 1:
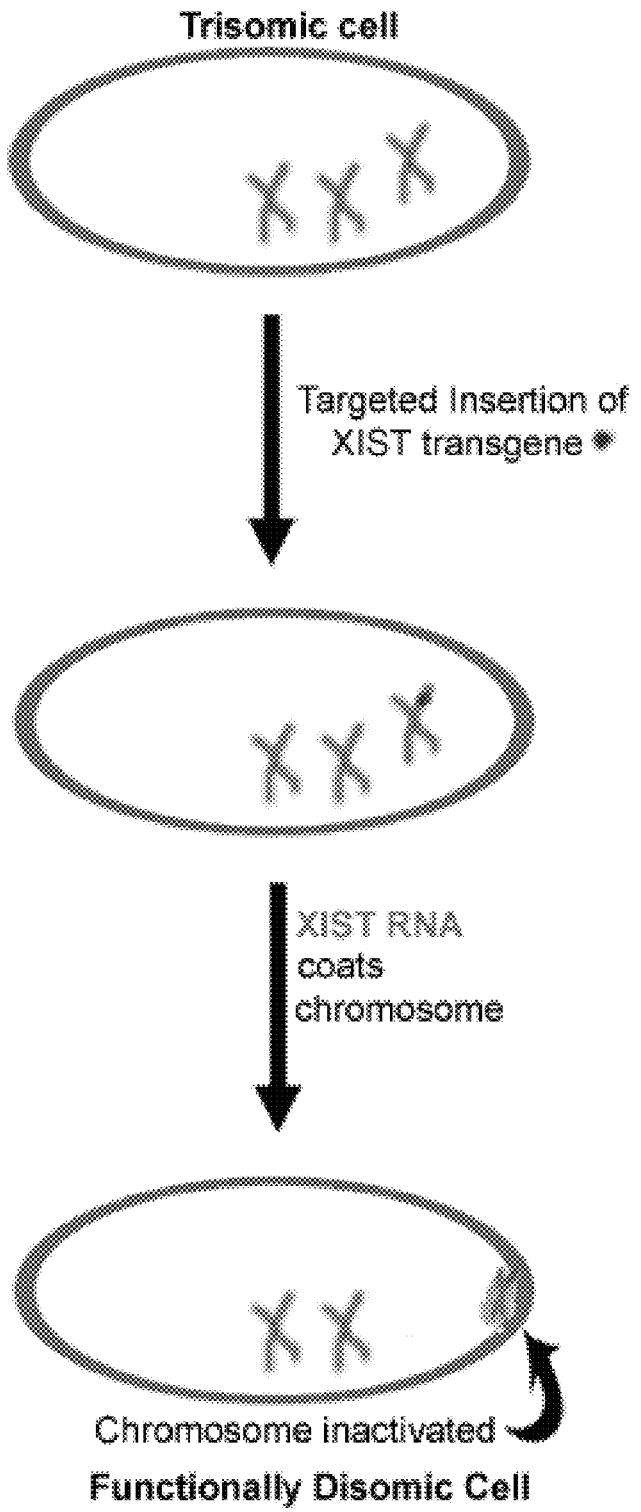
FIG. 1 is a schematic diagram illustrating the process of chromosomal inactivation. Three chromosomes are shown in the cell initially. Following targeted insertion of an Xist transgene, Xist RNA exerts its effect on chromosomal sequences that are cis to the Xist transgene, resulting in inactivation of one chromosome and a functionally disomic cell.
Figure 2:
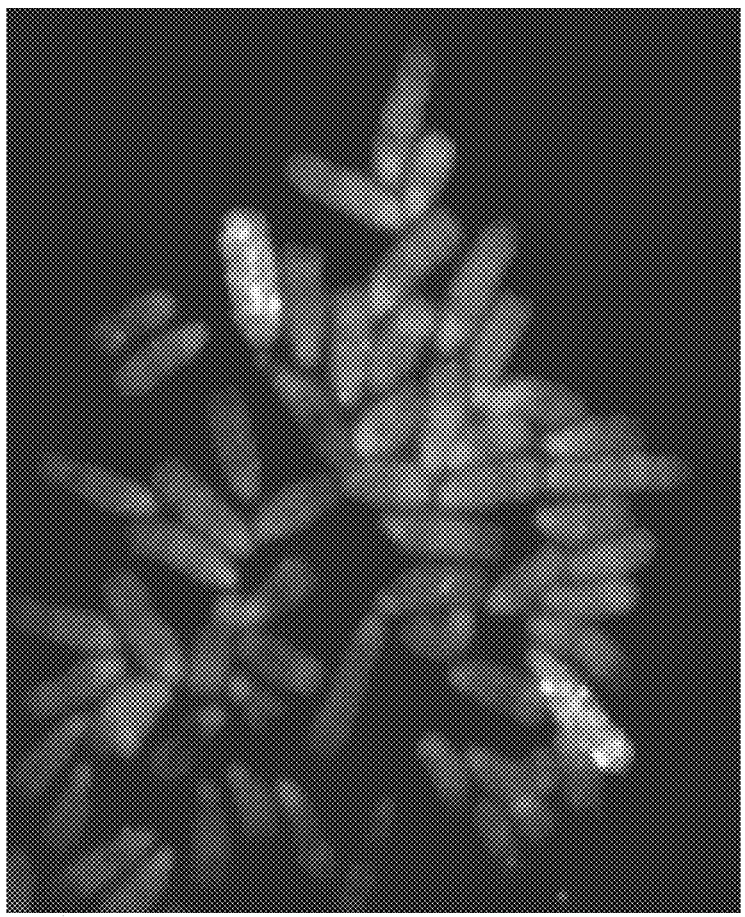
FIG. 2 is an image of chromosomes from an XXX mouse cell showing that Xist RNA (green in color and brighter in black-and-white) coats two X-chromosomes and inactivates both.

We set out to develop an innovative approach to chromosome therapy that would translate the system nature devised to dosage compensate the X chromosome in females. Nature assures proper "gene dosage" of X-linked genes between females (XX) and males (XY) via the Xist gene, which produces a large, non-coding RNA (Brown et al., *Cell*, 71:527-542, 1992; Clemson et al., *J. Cell Biol.* 132:259-275, 1996) that is expressed from and accumulates exclusively on the inactive X chromosome (Xi), "painting" the whole structure of the interphase chromosome territory (reviewed in Hall and Lawrence, *Semin. Cell Dev. Biol.* 14:369-378, 2003). Brown et al. discloses the cDNA sequence of Xist, which can be used in the design and construction of the nucleic acid constructs described herein. FIG. 2 shows mouse Xist RNA on two mitotic X chromosomes in a cell with X trisomy. Nature has also devised a counting mechanism such that all but one X chromosome is silenced (thus trisomy X has essentially normal gene dosage and is viable). Once Xist RNA coats the chromosome, a series of chromatin modifications occurs which are key hallmarks of the inactive X, including histone H3K27 methylation, H2A ubiquitination, macroH2A, and hypoacetylation of histone H4 (e.g., FIG. 5). Importantly, although Xist RNA is essential to initially enact this silencing process, once formed, the heterochromatic chromosome remains largely inactivated, even if Xist expression is later experimentally silenced (reviewed in Hall and Lawrence, *Semin. Cell Dev. Biol.* 14:369-378, 2003).

The new system would result in the silencing of additional or duplicated material (e.g., trisomies or segmental duplications) or translocated genomic material (e.g., the translocation of chromosomal arms that sometimes gives rise to birth defects or the translocations seen in certain cancers). The silencing would not be targeted to an intact X chromosome but could be targeted to an abnormal X chromosome lacking the Xist gene.

Where the intention is to "turn off" an extra chromosome, one can incorporate a silencing sequence using the compositions and methods described herein. The silencing sequence (e.g., an Xist gene of a human or other mammal such as a mouse or another silencing sequence described herein) is targeted to the region to be silenced (e.g., to the trisomic chromosome).

In another embodiment, where the intention is to kill a genetically aberrant cell (e.g., a cell in which a cancer-related translocation has occurred), one can incorporate a silencing sequence at the unique site of the translocation using the compositions and methods described herein. Silencing of the translocation would create a functional monosomy for the involved autosomal material which, depending on the chromosomal region silenced and the extent of the chromosomal region silenced would induce cell death or impede cell proliferation. In addition to incorporating a silencing sequence or as an alternative to incorporating a silencing sequence, one can use the present nucleic acid constructs and methods to target a "cell death" gene to the site of the translocation. For example, the nucleic acid construct can include an Xist gene and/or a gene encoding a toxin or pro-apoptotic factor. The toxins that can be expressed may include Shiga toxins 1 and 2 (Stx1 and Stx2); botulinum toxin from *Clostridium botulinum*; a virulence factor produced by *Bacillus anthracis* (e.g., a tripartite exotoxin referred to as anthrax toxin); a *Vibrio cholerae* multifunctional-autoprocessing RTX toxin; pertussis toxin from *Bordetella pertussis*; VacA from *Helicobacter pylori*; diphtheria exotoxin from *Corynebacterium diphtheriae*; *ricinus communis*; *pasteurella multocida* toxin (PMT); β-toxin-like peptide (named BmKBT) and two MkTx I homologues (named MkTx II and MkTx III), from a venom gland cDNA library of the Chinese scorpion *Buthus martensii* Karsch; haemorrhagic toxin acutolysin A from *Agkistrodon acutus: Bacillus thuringiensis* (Bt) toxin Cry1A and Cry1A(b); and Type A *Clostridium perfringens* cpb2. The pro-apoptotic proteins that can be expressed include, for example, Bcl-2-associated X protein (BAX), BH3 interacting domain death agonist (BID), Bcl-2 homologous antagonist killer (BAK), and Bcl-2-associated death promoter (BAD).

As noted, the translocation or duplication may be associated with a birth defect or may be a translocation associated with a cancer. The targeted chromosomal regions are then regions at or near the site of the translocation or duplication. These sites can be determined through genetic and sequence analysis, and several examples are known in the art. For example, one can target the following known sites of translocations: t(2;5)(p23;q35), which is associated with anaplastic large cell lymphoma; t(8;14), which is associated with Burkitt's lymphoma (c-myc); t(9;22)(q34;q11)/Philadelphia chromosome, which is associated with CML and ALL; t(11;14), which is associated with Mantle cell lymphoma (Bcl-1); t(11;22)(q24;q11.2-12), which is associated with Ewing's sarcoma; t(14;18)(q32;q21), which is associated with follicular lymphoma (Bcl-2); t(17;22), which is associated with dermatofibrosarcoma protuberans; t(15;17), which is associated with acute promyelocytic leukemia; t(1;12)(q21;p13), which is associated with acute myelogenous leukemia; t(9;12)(p24;p13), which is associated with CML and ALL (TEL-JAK2); t(X;18)(p11.2;q11.2), which is associated with synovial sarcomas; t(12;15)(p13;q25)-(TEL-TrkC), which is associated with acute myeloid leukemia, congenital fibrosarcoma, and secretory breast carcinoma.

Where the transgene is delivered to the patient, it will be useful to use a delivery system such as adeno associated virus, which also has the potential for site-specific integration.

Thus, the strategies described herein are applicable to trisomies, translocations, or any partial duplication of genomic DNA or aberration. For example, the present compositions and methods can be used to silence fragment or ring X-chromosomes associated with severe mental retardation.

Our strategies are based on our belief that trisomies can be treated by silencing essentially the whole trisomic chromosome, which would obviate the need to decipher the complex pathologies of the resulting syndromes and determining which specific genes are most "important" (if that is even possible at any practical level) (Antonarakis et al., *Trends Mol. Med.* 12:473-479, 2006). The silencing can be carried out in a variety of cell types which naturally represent or are induced to represent a variety of developmental stages (e.g., in early embryonic stem cells or induced pluripotent stem cells, fetal cells, neonatal cells, and other types of stem cells including hematopoietic cells, neural stem cells, mesenchymal stem cells, and other types of stem cells). In preparation for human therapies, the silencing can be carried out in a mouse model of Down syndrome. Several such models are available and known in the art. One could use any of the nucleic acid constructs described herein to determine if either the abnormal phenotype (or any aspect thereof) or embryonic lethality of a Down Syndrome mouse model could be rescued or ameliorated.

Figures 3A, 3B:
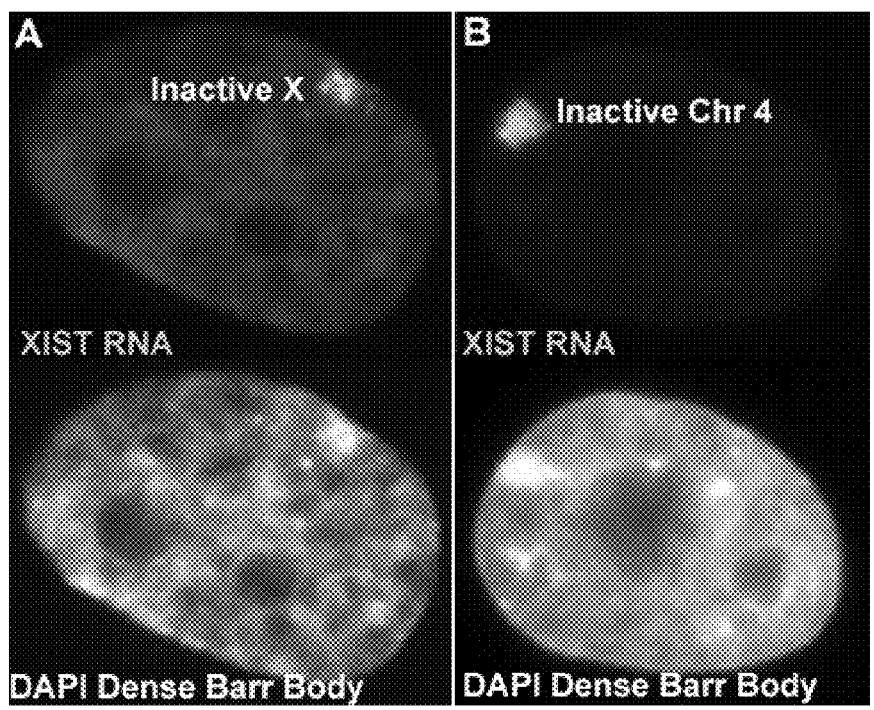
FIG. 3A is a photograph showing Xist RNA localized to an inactive X chromosome in a cell (upper photograph) and the corresponding DAPI dense Barr Body in the same cell (lower photograph).
FIG. 3B is a photograph showing Xist RNA localized to an inactive human Chr 4 carrying a transgenic Xist gene (upper photograph) and the lower panel shows the corresponding DAPI dense Barr Body in the same cell (lower photograph). Inactivation of the autosome occurred in an adult somatic cell (derived from a fibrosarcoma).
Figure 4:
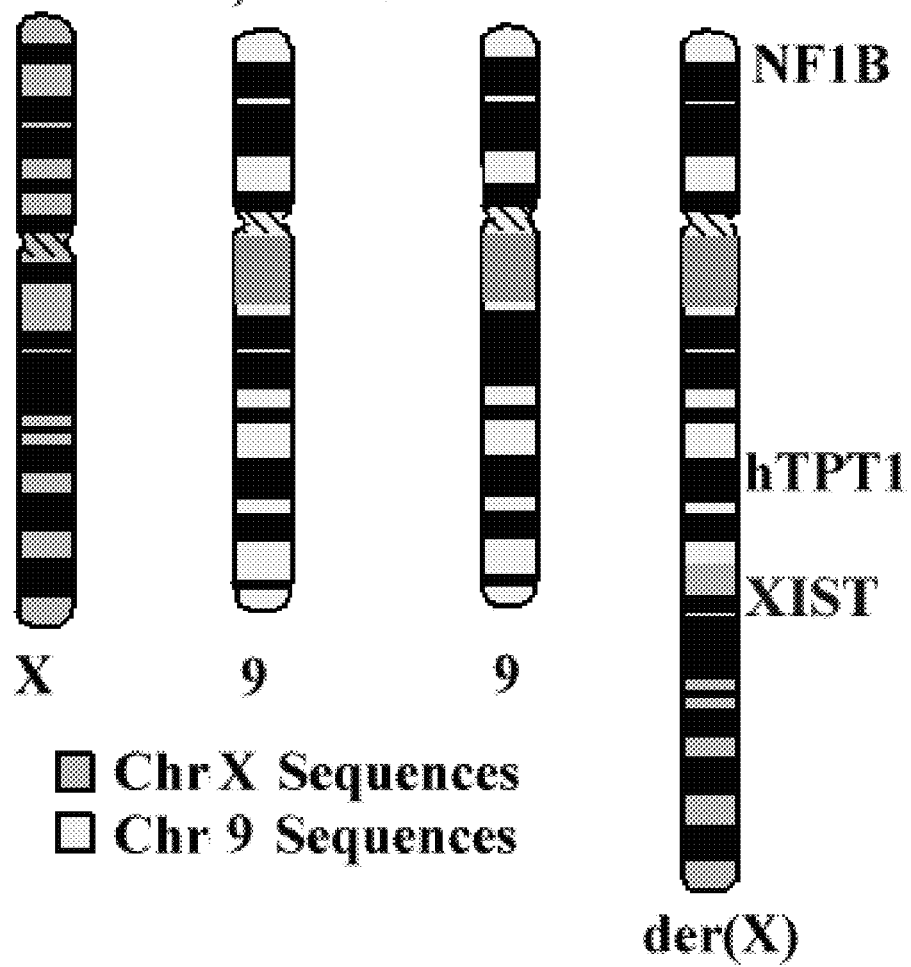
FIG. 4 is a schematic diagram of a karyotype of chromosomes involved in X;9 translocation, in which Xist RNA was shown to silence the duplicated Chromosome 9 material in the transgene, thereby avoiding the deleterious effects of partial Chr. 9 trisomy.

Although the potential therapeutic use of Xist transgenes for chromosomal trisomies has not been envisioned in the art, we believe that the mechanism whereby nature silences one X-chromosome in females can be extended to autosomal material, based on analysis of patients that carry naturally occurring X:autosome translocations. Two patients carrying X-autosome translocations in the context of trisomy for that autosome avoided otherwise devastating clinical consequences due to silencing of autosomal regions by endogenous Xic regions (Hall et al., *Proc. Natl. Acad. Sci. USA*, 99:8677-8682, 2002) (FIG. 4). In addition, we have shown that it is possible for an Xist transgene randomly integrated into a human autosome to induce silencing in somatic cells, when it had previously been believed that it could do so only in mouse embryonic stem cells (Hall et al., *Hum. Mol. Genet.*, 11:3157-3165, 2002) (e.g., see "Chr. 4 Barr Body in FIG. 3). We have cultured and used the transgenic cells described herein, and we have observed highly stable Xist expression and autosome silencing. We have also found evidence that two cultured (neoplastic) cell lines support chromosome silencing to a large degree at most of the random integration sites tested (Chow et al., *Proc. Natl. Acad. Sci. USA* 104:10104-10109, 2007). A caveat to these studies is that they were done in transformed cell lines, leaving open the possibility that the neoplastic changes somehow allow formation of Xi heterochromatin. However, several recent studies from our lab and others demonstrate that cancer cells most commonly lose heterochromatin, including the inactive X (Pageau et al., 2007), thus we believe this is unlikely to be the explanation. No prior studies have described the use of a transgenic construct that is integrated into an autosome in a site-specific manner. The present nucleic acid constructs include targeting elements (e.g., first and second targeting elements) that drive integration of a silencing sequence (e.g., an Xist transgene) into a selected or targeted region of the genome (e.g., into a trisomic chromosome). The first and second sequences and/or the first and second targeting elements are nucleic acid sequences that share sequence homology (including sequence identity) with a chromosomal site and, due to base pairing between the first and second sequences (and/or the first and second targeting elements) and sequences present at the chromosomal site, promote site-specific integration of all or part of a nucleic acid construct of which they are a part into the chromosomal site.

Integrated Mouse Xist or human Xist transgenes can silence an autosome, as shown by studies in mouse embryonic stem cells (Wutz and Jaenisch, *Mol. Cell,* 5:695-705, 2000; Savarese et al., *Mol. Cell Biol.* 26:7167-7177, 2006) and in human somatic (fibrosarcoma) cells (FIG. 3; Hall et al., *Hum. Mol. Genet.* 11:3157-3165, 2002; Chow et al., *Proc. Natl. Acad. Sci. USA* 104:10104-10109, 2007). Natural autosomal silencing by Xist was also shown in patient cells, with an autosomal trisomy due to X;autosome translocations (Hall et al., *Proc. Natl. Acad. Sci. USA* 99:8677-8682, 2002; (FIG. 4)). Although the silencing of autosomal material may not be quite as complete or may vary somewhat between autosomal regions, autosomes studied to date are largely if not entirely silenced in response to Xist RNA. While Chr. 21 has not been directly tested, its small (~50 Mb) acrocentric (essentially no short arm) structure is favorable, since Xist RNA would not need to spread far or across a centromere.

The fact that, to our knowledge, targeted inactivation of autosomes has never been discussed in the literature, possibly due to the belief that an Xist transgene cannot silence a chromosome outside a very narrow and early embryonic window and/or because the use of Xist transgenes for chromosomal therapeutic purposes was not envisioned. However, our studies of human Xist transgenes in adult cells and in differentiated embryonic cells (induced to express Xist post-differentiation) lead us to believe that the potential for Xist-mediated chromosome therapy in somatic cells is significant.

The present compositions and methods are applicable to abnormalities involving duplication of chromosomal material. Duplication of even a small chromosome fragment has severe clinical consequences. For example, Turner's syndrome (45, X) females have only one X-chromosome but typically have a quite mild phenotype, with normal intelligence but primary amenorrhea and sterility. However, Turner syndrome fetuses often have a fragment of the second X chromosome, which can result in either a very severe phenotype or the Turner-like mild one. A key to whether this fragment will be deleterious is whether or not it contains the Xist gene (Nussbaum et al., *Thompson and Thompson Genetics in Medicine,* Philadelphia, Pa., Saunders/Elsevier, 2007). If the Xist gene is present, the chromosome fragment is silenced and the deleterious effects are avoided. Thus, Xist could be inserted into an abnormal chromosome that lacks Xist sequences. Another category of duplication events arises via imbalanced translocations, and we have previously characterized two examples in which the imbalance was rescued by the Xist gene on the translocated chromosome. FIG. 4 shows the karyotype of an individual with a normal phenotype, even though they carried a Chr. 9 trisomy which would otherwise be lethal. Instead, the extra chr. 9 material was silenced by the Xist gene on the translocated chromosome. We showed that Xist RNA coated much of the Chr. 9 material, as it did Chr. 14 material in an analogous example, and in both cases Xist nullified what would have been a devastating trisomy (reviewed in Hall and Lawrence, *Semin. Cell Dev. Biol.* 14:369-378, 2003). Similarly, Xist transgenes could potentially silence any rearrangement which creates duplication (partial trisomy) for part of a chromosome.

Nucleic Acid Constructs:

Accordingly, the present invention features nucleic acid constructs that include a silencing sequence and one or more targeting sequences (e.g., first and second sequences that flank the silencing sequence and direct insertion of the silencing sequence into a targeted chromosome). The silencing sequence can be or can include the sequence of an XIC (X inactivation complex) locus or any portion thereof that encodes an RNA capable of silencing the chromosome into which it has been inserted. For example, the constructs can include an XIC locus lacking the sequences 3' to Xist that trigger the "counting" mechanism. Other constructs can include the Xist gene, with or without some or all of the intronic sequences, or a biologically active variant of the Xist gene (e.g., a fragment or other mutant). For information regarding the structure of XIC, one can consult Wutz and Gribnau (*Curr. Opin. Genetics Dev.* 17:387-393, 2007).

The silencing sequence (e.g., an Xist transgene) can silence the expression of one or more genes located within a trisomic and/or translocated chromosomal region located in cis to the integrated Xist transgene. In certain embodiments, the targeting elements are sequences homologous to those that occur naturally in the trisomic and/or translocated chromosomal region and will promote integration of the silencing sequence (e.g., an Xist transgene) to the corresponding trisomic and/or translocated chromosomal region. The targeted region may be a polymorphic region (i.e., a region where corresponding sequences differ between paired chromosomes in an individual). Whether the present nucleic acid constructs are used alone or in combination with a second moiety that enhances or facilitates homologous recombination (e.g., a zinc finger nuclease), the targeted region can be one having only one or more polymorphic sites, such as single nucleotide polymorphisms (SNPs). Zinc finger domains can recognize and target highly specific chromosomal sequences, including SNPs, which can be used to facilitate targeted integration of the transgene to particular alleles in just one of the homologous chromosomes. As noted, a vector that may facilitate both insertion of a transgene and delivery to a cell is an adeno associated virus, but delivery of the transgene to cells in vitro may be done by commonly used transfection methods, without the use of any adeno-associated, lenti or other virus.

In certain other embodiments, the targeting elements are homologous to non-naturally occurring sequences that have been introduced into a trisomic and/or translocated region by recombinant methods. In these embodiments, the targeting elements will promote integration of the transgene at a site defined by the non-naturally occurring sequences, such as FRT sequences, which can promote integration into that site.

Regardless of whether the silencing sequence is inserted with the assistance of a polymorphism on the targeted chromosome or whether the nucleic acid constructs are used in combination with a second moiety that enhances or facilitates homologous recombination, the present compositions and methods can be designed to target just one copy of a chromosome if desired. These methods can also be used to target one or more than one site on a targeted chromosome (e.g., two, three, or four sites), which may or may not be in close proximity to one another. While it is our expectation that the RNA encoded by the silencing sequence or transgene will silence most if not all of the genes residing on the targeted chromosome, one can nevertheless target specific genes (e.g., genes associated with Alzheimer's Disease (e.g., APP), leukemias (e.g., RUNX1) or other conditions that occur with increased frequency in patients with trisomies or translocation).

As would be understood in the art, the term "recombination" is used to indicate the process by which genetic material at a given locus is modified as a consequence of an interaction with other genetic material. Homologous recombination indicates that recombination has occurred as a consequence of interaction between segments of genetic material that are homologous or identical. In contrast, "non-homologous" recombination indicates a recombination occurring as a consequence of the interaction between segments of genetic material that are not homologous (and therefore not identical). Non-homologous end joining (NHEJ) is an example of non-homologous recombination.

As used herein, an Xist transgene refers to a nucleic acid sequence having the sequence of all or part of a naturally occurring Xic region so long as it (a) includes an Xist RNA coding sequence or a biologically active variant thereof and (b) is functional (e.g., the Xist transgene is capable of silencing the expression of one or more genes in cis when integrated into a chromosome). The Xist transgene may carry one or more regulatory elements found in the Xic region that are not a part of the Xist coding sequence. For example, deletion of the DXPas34 locus found 3' to the Xist coding sequence eliminates Xist expression in mammalian embryonic stem cells as described in Debrand et al. (*Mol. Cell. Bio.*, 19:8513-8525, 1999) herein incorporated by reference. As a further example, silencing by mouse Xist transgenes have been shown to require a conserved repeat sequence located at the 5' end of Xist (Wutz et al., *Nat. Genetics*, 30:167-174, 2002).

The Xist transgene need not include the whole of the Xist gene sequence, although it may. For example, the Xist transgene may be derived from an Xist cDNA cloned from one of multiple naturally occurring splice variants. This cDNA may lack sequences corresponding to one or more introns or exons or portions thereof. Additionally, the Xist transgene may include non-naturally occurring Xist coding sequences. For example, the Xist coding sequence may be mutated (e.g., truncated) or otherwise variant with respect to naturally occurring Xist coding sequences so long as it includes sequences that are required for transgene function. For example, deletion analysis demonstrates that the first exon of human Xist is sufficient for both transcript localization and the induction of silencing (Chow et al., *Proc. Natl. Acad. Sci. USA* 104:10104-10109, 2007). Thus, smaller Xist constructs can be generated that are more easily manipulated but still biologically active.

Non-limiting examples of Xist transgenes (derived from mouse and human sequences) that are useful in this invention are described in the following references which are herein incorporated by reference: Chow et al. (*Proc. Natl. Acad. Sci. USA* 104:10104-10109, 2007); Hall et al. (*Proc. Natl. Acad. Sci. USA* 99:8677-8682, 2002); Chow et al. (*Genomics*, 82:309-322, 2003); and Wutz et al. (*Nat. Genet.*, 2002, 30:167-174, 2002).

The nucleic acid constructs of this invention include targeting sequences or elements that promote sequence specific integration of an Xist transgene into a chromosomal site (e.g., by homologous recombination). Methods for achieving site-specific integration by ends-in or ends-out targeting are known in the art and in the nucleic acid constructs of this invention, the targeting elements are selected and oriented with respect to the Xist transgene according to whether ends-in or ends-out targeting is desired. In certain embodiments, two targeting elements flank the Xist transgene.

As described previously, the targeting element may be identical in sequence to a naturally occurring sequence found in a trisomic and/or translocated chromosomal region. For example, a targeting element may be identical in sequence to a sequence found in any one of human chromosomes 9, 13, 14, 18, or 21 (as described in Hattori et al., *Nature*, 405:311-319, 2000) or in any other chromosome. In another example, a targeting element may be identical in sequence to a sequence found in any one of mouse chromosomes 16, 17, or T($17^{16}$)65Dn.

A targeting sequence or element may vary in size. In certain embodiments, a targeting element may be at least or about 100, 200, 300, 400, 500, 600, 700, 800, 900, 1000, 2000, 3000, 4000, 5000, 6000, 7000, 8000, 9000, 10000 bp in length (or any integer value in between). In certain embodiments, a targeting element is homologous to a sequence that occurs naturally in a trisomic and/or translocated chromosomal region, including a polymorphic sequence which may be present on just one of the homologous chromosomes.

Accordingly, in one aspect, the invention provides an isolated or purified nucleic acid construct that includes a silencing sequence (e.g., an Xist transgene) and one or more targeting sequences that are oriented with respect to each other in such a way that the Xist transgene can be integrated in a site-specific fashion into a chromosomal site when the nucleic acid construct is introduced into a cell.

The construct elements as described here may be variants of naturally occurring sequences. Preferably, any construct element (e.g., an Xist transgene, other non-coding, silencing RNA, or a targeting element) includes a nucleotide sequence that is at least 60% identical to its corresponding naturally occurring sequence (its reference sequence, e.g., an Xist coding region, a human Chr 21 sequence, or any duplicated or translocated genomic sequence). More preferably, the silencing sequence or the sequence of a targeting element is at least 65%, 70%, 75%, 80%, 85%, 90%, 91%, 92%, 93%, 94%, 95%, 96%, 97%, 98%, 99% identical to its reference sequence (e.g., SEQ ID NO:1 or SEQ ID NO:2).

As used herein, "% identity" of two nucleic acid sequences is determined using the algorithm of Karlin and Altschul (*Proc. Natl. Acad. Sci. USA*, 87:2264-2268, 1990), modified as in Karlin and Altschul, *Proc. Natl. Acad. Sci. USA*, 90:5873-5877, 1993). Such an algorithm is incorporated into the NBLAST and XBLAST programs of Altschul et al. (*J. Mol. Biol.* 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (*Nucl. Acids Res.*, 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

The nucleic acid constructs of the invention can be prepared by recombinant methods that are known in the art.

Moreover, the present invention provides a vector containing one or more of the nucleic acid constructs described herein. The vector may be useful for propagating the nucleic acid construct or may contain elements useful for integrating the Xist transgene into a chromosome once the vector has been introduced into a mammalian cell. For example, the vector may be an expression vector designed to express a recombinase, such as Fok1 recombinase, coupled with a zinc finger nuclease, designed to aid in the integration of the silencing sequence (e.g., an Xist transgene) into a chromosome at a specific site.

For expression in animal cells, such as embryonic stem cells, adult bone marrow stem cells, CHO, COS, and NIH3T3 cells, the expression vector must have a promoter such as an SV40 promoter (Mulligan et al., *Nature* 277:108, 1979), MMLV-LTR promoter, EF1α promoter (Mizushima et al., *Nucl. Acids Res.* 18:5322, 1990), and CMV promoter. The vector may also carry an inducible promoter, for example, a doxycycline inducible promoter, or a promoter that may be activated to express Xist RNA by excision of intervening sequences, using a Cre-lox system. More generally, the nucleic acid construct that includes a silencing sequence can also include one or more control elements that facilitate expression of the silencing sequences. These control elements include promoter, enhancer, and termination sequences, and the promoter may be a constitutively active, inducible, tissue-specific or developmental stage-specific promoter.

Our findings further support the conclusion that chromosome inactivation also occurs in mature cells (e.g., in differentiated cells), but at a slower rate than in embryonic cells. Regarding developmental competence, we note that, in addition to the requirement for expression of an integrated Xist transgene, the cells must respond to Xist to support initiation of chromosome inactivation, which normally occurs during the earliest transition of pluripotent embryonic stem cells to more committed/differentiated cells. While all somatic cells in adult females are competent to maintain the silenced state, it has been believed that only early embryonic stem cells can initiate chromosome silencing in response to Xist. A study in mouse ES cells reported that if expression of Xist was delayed just two days after differentiation, the cells had lost the competence to initiate chromosome inactivation (Wutz et al. 2000, Molecular Cell). However, our study in human somatic cells (Hall et al., 2002, PNAS) first showed that a randomly integrated Xist transgene was able to initiate chromosome inactivation of the autosome (carrying the ectopic Xist gene) in human HT1080 cells, derived from an adult male fibrosarcoma. Our studies in Chow et al. (PNAS 2007) confirmed this for HT1080 cells and human 293 cells; however, because both of these somatic cell lines have neoplastic origins, it has been thought that their capacity to initially form the heterochromatic chromosome may not reflect the capacity of fully normal cells. However, in other work, we and others have shown that cancer cells tend to lose heterochromatin, including Xi (Pageau et al., 2007, Nature Reviews Cancer).

To further investigate whether normal, non-neoplastic somatic cells are competent to initiate chromosome inactivation post-differentiation, we differentiated mouse ES cells carrying an inducible-Xist transgene, essentially the same experimental system used in Wutz et al. Our findings demonstrate that these normal murine ES cells are able to support chromosome silencing post-differentiation. ES cells were differentiated for several (4-9) days prior to induction of Xist expression with doxycycline, and then cells were evaluated at various intervals up to two weeks following Xist expression. Whereas Wutz et al. waited just 2 days after Xist expression to evaluate whether chromosome silencing had taken place, we surmised that the multi-step inactivation process may occur more slowly in somatic cells. Indeed, our findings demonstrate that the vast majority of cells in these differentiated cultures had supported chromosome silencing, between 7-14 days after Xist expression. Thus, these findings indicate that the successful chromosome silencing in Hall et al. (2002) was likely not due to the neoplastic nature of the cells used, but to the long, ten-day time-frame over which the cells were evaluated.

While naturally occurring stem cells may have an enhanced competence to respond to Xist to initiate chromosome silencing, differentiated somatic cells, such as fibroblasts, can also be induced to form induced pluripotent stem cells (iPS cells) by introduction of specific genes that control developmental programs. The iPS cells have properties essentially like those of ES cells, and thus would be competent to not only initiate X-inactivation in response to Xist, but to form a variety of stem cells committed to specific cell types, such as neural, hematopoeitic, cardiac myoblasts, etc., which may enhance their therapeutic utility.

The present nucleic acid constructs can be used to integrate a silencing sequence (e.g., the Xist transgene) into a chromosome in murine or human embryonic, iPS, or adult stem cells (for example, see Zhang, *J. Hematotherapy & Stem Cell Research* 12:625-634, 2003, herein incorporated by reference). For example, bone marrow stem cells and induced pluripotent stem cells may be used. Pluripotency can be induced as described above by the methods of Wernig et al. (*Nature* 448:318-325, 2007); Shi et al. (*Cell Stem Cell.* 2:525-528, 2008); and Nakagawa et al. (*Nature Biotechnol.*, 26:101-106, 2008), all of which are incorporated by reference herein. In addition, neural precursor cells as described in Zhang et al. (*Nature Biotechnology*, 19:1129-1133, 2001) may be used. For example, the following steps could be used to generate a population of corrected patient stem cells of a particular type that will not be subject to immune rejection (because they are isogenic to the patient's DNA), but which can provide therapeutic value. 1) providing fibroblasts or lymphocytes or other cells from a patient with trisomy 21 (Down Syndrome); 2) treating these cells with reprogramming factors shown to generate induced pluripotent stem cells or early developmental cells; 3) introducing into these cells a zinc finger nuclease (with Fok1 recombinase) specifically designed to promote efficient integration of exogenous DNA at a specific location; 4) introducing an Xist transgene flanked by sequences homologous to the desired site of integration under the control of a promoter designed to be expressed as desired, and verifying that Xist is expressed and silences the chromosome; and 6) culturing the Xist-transgenic iPS cells under conditions that promote the generation of neural, hematological, cardiac or other desired stem cells. The corrected stem cells (in which the deleterious chromosome or region has been silenced) can then be reintroduced into the patient's body so as to achieve therapeutic benefit, by introducing the appropriate type of stem cells into the appropriate tissue or organ. For example, in Down Syndrome there is thought to be loss of neurons or neural function that appears to be progressive with age that contributes to mental retardation. Similarly, Alzheimer's Disease is associated with loss of proper neuron function. As has been shown in mouse models of another neurological disease, intracranial injection of normal neural stem cells can provide therapeutic benefit (Lee et al., *Nature Med.* 13:439-447, 2007) and, more generally, cell implantation methods, including via intracranial surgery, are known in the art. Similarly, Down Syndrome is associated with hematological abnormalities that could be treated by correcting patient cells that are natural bone marrow stem cells or induced bone marrow stem cells (from iPS cells or other mesenchymal stem cells). In a patient with TMD (transient myeloproliferative disorder, which often precedes leukemia) or leukemia, the corrected bone marrow stem cells could be introduced into the patient's blood, to repopulate the bone marrow with more normal stem cells. Similarly, babies with Down Syndrome have a high rate of congenital heart defects, which in some cases could be treated by the use of cardiac stem cell therapy, where the stem cells used would be isogenic with the patient's DNA but would be corrected by silencing the trisomic chromosome.

In addition, the vector may contain a marker for the selection of transfected cells (for instance, a drug resistance gene for selection by a drug such as neomycin, hygromycin, and G418). Such vectors include pMAM, pDR2, pBK-RSV, pBK-CMV, pOPRSV, pOP13, and so on. More generally, the term "marker" refers to a gene or sequence whose presence or absence conveys a detectable phenotype to the host cell or organism. Various types of markers include, but are not limited to, selection markers, screening markers, and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as green fluorescent protein (GFP), GUS or β-galactosidase. Molecular markers are, for example, sequence features that can be uniquely identified by oligonucleotide probing, for example RFLP (restriction fragment length polymorphism), or SSR markers (simple sequence repeat). To amplify the gene copies in host cell lines, the expression vector may include an aminoglycoside transferase (APH) gene, thymidine kinase (TK) gene, E. coli xanthine guanine phosphoribosyl transferase (Ecogpt) gene, dihydrofolate reductase (dhfr) gene, and such as a selective marker.

In vivo expression of the DNA of the invention may be performed by constructing the DNA into an appropriate vector and transfecting the construct into the body using retrovirus, liposome, cationic liposome, adeno-associated virus (particularly where chromosome 19 is targeted), lentivirus, electroporation and so on. It is possible to use such a construct to perform gene therapy for diseases resulting from chromosomal trisomies and/or translocations or duplications. Examples of vectors used for this purpose include retrovirus vector (such as pZIPneo), but are not limited thereto. General manipulations, such as insertion of the DNA into the vector, may be performed by using standard methods (Molecular Cloning, 5.61-5.63). The vector may be administered to the patient through in vivo administration or by way of methods that are carried out, at least partially, ex vivo. For example, the vector may be administered to cells harvested from a patient and maintained in culture. The construct-carrying or vector-carrying cells can then be introduced to the patient. For example, stem cells or hematopoietic cells can be harvested from a patient or obtained from another source, modified in culture as described here to include insertion of a silencing sequence into a targeted site, and administered to the patient. To facilitate the method, the recipient patient may be subjected to bone marrow ablation.

Facilitating Targeting with Zinc Finger Nucleases:

Targeting the present "silencing" constructs to particular chromosomes or regions of chromosomes can be facilitated by introducing chimeric zinc finger nucleases (ZFNs) into a cell. These nucleases exploit endogenous cellular mechanisms for homologous recombination and repair of double stranded breaks in genetic material. ZFNs can be used to target a wide variety of endogenous nucleic acid sequences in a cell or organism. The present compositions include cleavage vectors that target a ZFN to a region within a trisomic chromosome or within a translocated sequence, and the methods include transfection or transformation of a host cell or organism by introducing a cleavage vector encoding a ZFN (e.g., a chimeric ZFN), or by introducing directly into the cell the mRNA that encodes the recombinant zinc finger nuclease, or the protein for the ZFN itself. One can then identify a resulting cell or organism in which a selected endogenous DNA sequence is cleaved and exhibits a mutation or DNA break at a specific site, into which the transgene will become integrated.

To help clarify the nucleic acid to which we are referring, we tend to use the term "nucleic acid construct" to describe a nucleic acid that includes the silencing sequence and the term "cleavage vector" to describe a nucleic acid that encodes the ZFN. It is to be understood, however, that both are, or include, nucleic acid sequences (e.g., DNA); both can be properly referred to as constructs; and both can be properly referred to as vectors, particularly when they include nucleic acid sequences that facilitate entry into a host cell.

The methods can include construction of a vector or isolation of an mRNA encoding a chimeric ZFN by, for example, selecting a zinc finger DNA binding domain capable of preferentially binding to a specific host DNA locus to be mutated; further selecting a non-specific DNA cleavage domain capable of cleaving double-stranded DNA when operatively linked to the binding domain and introduced into the host cell; further selecting a promoter region capable of inducing expression in the host cell; and further operatively linking DNA encoding the binding domain and the cleavage domain and the promoter region to produce a DNA construct. Elements are operatively linked when they work in concert. For example, a control element and a transgene are operatively linked when the control element alters the expression of the transgene. To bring a transgene under the control of a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA.

The nucleic acid (e.g., DNA) construct is then introduced into a target host cell and at least one host cell exhibiting recombination at the target locus in the host DNA is identified.

The ZFN can be a chimeric protein molecule that directs targeted genetic recombination or targeted mutation in a host cell by causing a double stranded break at the target locus. For example, a ZFN can include a DNA-binding domain that includes at least one zinc finger, and that binding domain can be operatively linked to a DNA-cleavage domain. The DNA-binding domain is at the N-terminus of the chimeric protein molecule, and the DNA-cleavage domain is located at the C-terminus of the molecule.

The ZFN can include multiple (e.g., at least three (e.g., 3, 4, or 5)) zinc fingers in order to improve its target specificity. The zinc finger domain can be derived from any class or type of zinc finger. For example, the zinc finger domain can include the $Cys_2His_2$ type of zinc finger that is very generally represented, for example, by the zinc finger transcription factors TFIIIA or Sp1. In a preferred embodiment, the zinc finger domain comprises three $Cys_2His_2$ type zinc fingers.

The DNA recognition and/or the binding specificity of a ZFN can be altered in order to accomplish targeted genetic recombination at any chosen site in cellular DNA. Such modification can be accomplished using known molecular biology and/or chemical synthesis techniques. ZFNs comprising zinc fingers having a wide variety of DNA recognition and/or binding specificities are within the scope of the present invention.

The ZFN DNA-cleavage domain can be derived from a class of non-specific DNA cleavage domains, for example the DNA-cleavage domain of a Type II restriction enzyme such as FokI. Thus, a chimeric ZFN useful in the present methods can include three Cys$_2$His$_2$ type zinc fingers and a DNA-cleavage domain derived from the Type II restriction enzyme FokI. In this event, each zinc finger contacts three consecutive base pairs of DNA creating a 9 bp recognition sequence for the ZFN DNA binding domain. The DNA-cleavage domain of the embodiment requires dimerization of two ZFN DNA-cleavage domains for effective cleavage of double-stranded DNA. This imposes a requirement for two inverted recognition (target DNA) sites within close proximity for effective targeted genetic recombination. If all positions in the target sites are contacted specifically, these requirements enforce recognition of a total of 18 base pairs of DNA. There may be a space between the two sites. The space between recognition sites for ZFNs may be equivalent to 6 to 35 bp of DNA. The region of DNA between the two recognitions sites may be referred to as the "spacer."

A linker, if present, between the cleavage and recognition domains of the ZFN can be a sequence of amino acid residues that result in a flexible linker is flexible, although linkerless constructs tend to improve target site specificity. A linkerless construct has a strong preference for binding to and then cleaving between recognition sites that are 6 bp apart. However, with linker lengths of between 0 and about 18 amino acids in length, ZFN-mediated cleavage occurs between recognition sites that are between 5 and 35 bp apart. For a given linker length, there will be a limit to the distance between recognition sites that is consistent with both binding and dimerization. As noted, there may be no linker between the cleavage and recognition domains, and the target locus can include two nine nucleotide recognition sites in inverted orientation with respect to one another, separated by a six nucleotide spacer.

To target genetic recombination or mutation, two 9 bp zinc finger DNA recognition sequences are identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a cleavage domain of a Type II restriction enzyme.

A silencing sequence flanked by sequences (typically 400 bp-5 kb in length) homologous to the desired site of integration can be inserted (e.g., by homologous recombination) into the site cleaved by the endonuclease, thereby achieving a targeted insertion. When used in combination with a ZFN construct, the silencing sequence may be referred to as "donor" nucleic acid or DNA.

The various active sequences, including the silencing sequence and the sequence encoding a chimeric ZFN can be introduced into a host cell on the same vector or separately (e.g., on separate vectors or separate types of vectors at the same time or sequentially). Methods for introducing the various nucleic acids, constructs, and vectors are discussed further below and are well known in the art.

The nucleic acid constructs including a silencing sequence, whether used alone or in combination with a ZFN can either introduce a therapeutic sequence or disrupt a targeted sequence, gene, or chromosome in a somatic cell or in a germ cell. In some cases, a therapeutic Xist transgene may be inserted in such a way as to simultaneously disrupt a deleterious gene, such as the APP gene that leads to high incidence of Alzheimer's Disease. Cells with such disruption in the targeted gene can be "selected for" in order to create an organism without a functioning target sequence or for administration to a patient. Accordingly, the constructs, other compositions, and methods of the present invention are applicable to a wide range of cell types and organisms.

While our own intention is to develop therapies for human patients, the silencing methods we have discovered can be carried out with a single celled or multicellular organism; an oocyte; a gamete; a germline cell in culture or in a host organism; a somatic cell in culture or in a host organism; an insect cell, including an insect selected from the group consisting of Coleoptera, Diptera, Hemiptera, Homoptera, Hymenoptera, Lepidoptera, or Orthoptera, including a fruit fly, a mosquito and a medfly; a plant cell, including a monocotyledon cell and a dicotyledon cell; a mammalian cell, including but not limited to a cell of a mouse, rat, pig, sheep, cow, dog, cat, or human; an avian cell, including, but not limited to a cell of a chicken, turkey, duck or goose; or a fish cell, including, but not limited to zebrafish, trout and salmon.

DNA encoding an identifiable marker can also be included with either the nucleic acid construct including the silencing sequence or the vector carrying the ZFN-encoding sequence. Such markers may include a gene or sequence whose presence or absence conveys a detectable phenotype to the host cell or organism. Various types of markers include, but are not limited to, selection markers, screening markers and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as Green Fluorescent Protein (GFP), beta-glucuronidase (GUS) or beta-galactosidase. Markers may also be negative (e.g., codA) or positive selectable markers. Molecular markers are, for example, sequence features that can be uniquely identified by oligonucleotide probing, for example RFLP (restriction fragment length polymorphism), or SSR markers (simple sequence repeat).

The compositions and methods described herein can be used to accomplish germline gene therapy in mammals.

The frequency of homologous recombination in any given cell is influenced by a number of factors. Different cells or organisms vary with respect to the amount of homologous recombination that occurs in their cells and the relative proportion of homologous recombination that occurs is also species-variable. The length of the region of homology between donor and target affects the frequency of homologous recombination events, the longer the region of homology, the greater the frequency. The length of the region of homology needed to observe homologous recombination is also species specific. However, differences in the frequency of homologous recombination events can be offset by the sensitivity of selection for the recombinations that do occur. It will be appreciated that absolute limits for the length of the donor-target homology or for the degree of donor-target homology cannot be fixed but depend on the number of potential events that can be scored and the sensitivity of the selection for homologous recombination events. Where it is possible to screen $10^9$ events, for example, in cultured cells, a selection that can identify 1 recombination in $10^9$ cells will yield useful results. Where the organism is larger, or has a longer generation time, such that only 100 individuals can be scored in a single test, the recombination frequency must be higher and selection sensitivity is less critical. Random integration is discussed elsewhere herein. We note here, however, that random integration can be used in combination with selection for cells that have targeted the desired gene or chromosome.

Transformation can be carried out by a variety of known techniques which depend on the particular requirements of each cell or organism. Such techniques have been worked out for a number of organisms and cells and are readily adaptable. Stable transformation involves DNA entry into cells and into the cell nucleus. For single-celled organisms and organisms that can be regenerated from single-cells (which includes all plants and some mammals), transformation can be carried out in culture, followed by selection for transformants and regeneration of the transformants. Methods often used for transferring DNA or RNA into cells include forming DNA or RNA complexes with cationic lipids, liposomes or other carrier materials, micro-injection, particle gun bombardment, electroporation, and incorporating transforming DNA or RNA into virus vectors. Other techniques are well known in the art.

Where silencing is limited to less than an entire chromosome, boundary elements or sequences associated with escape from inactivation can be used to help impede the spread of the silencing RNA. For a description of a unique sequence feature of the X-chromosome that always escapes inactivation, see McNeil et al. (*Genome Res.* 16:477-484, 2006). This sequence is among those that can be used to confer "escape" from silencing. See also Filippova et al. (*Dev. Cell.* 8:31-42, 2005).

In the following paragraphs, we describe some delivery systems useful in practicing the present invention.

Liposomal formulations: In certain embodiments of the invention, the oligo- or polynucleotides and/or expression vectors containing silencing sequences and/or ZFNs may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated are cationic lipid-nucleic acid complexes, such as lipofectamine-nucleic acid complexes. Lipids and liposomes suitable for use in delivering the present constructs and vectors can be obtained from commercial sources or made by methods known in the art.

Microinjection: Direct microinjection of DNA into various cells, including egg or embryo cells, has also been employed effectively for transforming many species. In the mouse, the existence of pluripotent embryonic stem (ES) cells that can be cultured in vitro has been exploited to generate transformed mice. The ES cells can be transformed in culture, then micro-injected into mouse blastocysts, where they integrate into the developing embryo and ultimately generate germline chimeras. By interbreeding heterozygous siblings, homozygous animals carrying the desired gene can be obtained.

Viral Vectors as Expression Constructs:

Other viral vectors may be employed as expression constructs in the present invention. Vectors derived from, for example, vaccinia virus, adeno-associated virus (MV), and herpes viruses may be employed. Extensive literature is available regarding the construction and use of viral vectors. For example, see Miller et al. (*Nature Biotechnol.* 24:1022-1026, 2006) for information regarding adeno associated viruses. Defective hepatitis B viruses, may be used for transformation of host cells. In vitro studies show that the virus can retain the ability for helper-dependent packaging and reverse transcription despite the deletion of up to 80% of its genome. Potentially large portions of the viral genome can be replaced with foreign genetic material. The hepatotropism and persistence (integration) are particularly attractive properties for liver-directed gene transfer. The chloramphenicol acetyltransferase (CAT) gene has been successfully introduced into duck hepatitis B virus genome in the place of the viral polymerase, surface, and pre-surface coding sequences. The defective virus was cotransfected with wild-type virus into an avian hepatoma cell line, and culture media containing high titers of the recombinant virus were used to infect primary duckling hepatocytes. Stable CAT gene expression was subsequently detected.

Non-Viral Methods:

Several non-viral methods are contemplated by the present invention for the transfer into a host cell of DNA constructs encoding ZFNs and, when appropriate, donor DNA. These include calcium phosphate precipitation, lipofectamine-DNA complexes, and receptor-mediated transfection. Some of these techniques may be successfully adapted for in vivo or ex vivo use.

In one embodiment of the invention, the expression constructs may simply consist of naked recombinant DNA, or in some cases mRNA for the recombinant ZFN. Transfer of the construct may be performed by any of the nuclei acid transfer methods mentioned above which physically or chemically permeabilize the cell membrane. For example, polyomavirus DNA in the form of $CaPO_4$ precipitates was successfully injected into liver and spleen of adult and newborn mice which then demonstrated active viral replication and acute infection. In addition, direct intraperitoneal injection of $CaPO_4$ precipitated plasmid expression vectors results in expression of the transfected genes.

EXAMPLES

Silencing a Trisomic Chromosome in Human Somatic Cells and in a Trisomic Mouse Model of DS We will introduce an Xist transgene into human and mouse trisomic cells, and demonstrate silencing of the trisomic chromosome in culture. We believe that human Xist transgenes can: (1) initiate silencing outside of the normal very early development window in normal (non-neoplastic) human somatic cells and/or stem cells; (2) be targeted to and effectively silence an autosome (e.g., trisomic human chromosome 21) in human cultured cells; and with higher efficiency techniques, (3) stably silence the trisomic chromosome in mouse ES cells and mice in an established mouse model of Down Syndrome, thereby ameliorating the deleterious phenotype. Trisomic mouse models of Down Syndrome are available and can be used to test both chromosome silencing and amelioration of the phenotype of DS mice (see below).

Experiments in Mouse ES or iPS Cells and a Mouse Model of Down Syndrome:

The goal of these studies is to first target an Xist transgene into ES, iPS or bone marrow cells derived from one or more mouse models of Down Syndrome and verify that the trisomic chromosome is effectively silenced. Two available mouse DS models carry trisomy chr. 16 (syntenic to human 21) and one carries an actual human Chr 21 as the third chromosome (further detailed below).

Trisomic Mouse Models of DS:

Mouse chromosome 16 is largely syntenic to human chromosome 21, and mouse models of DS have been developed that are either trisomic for mouse chr. 16, or carry as the third chromosome an actual human chromosome 21 (reviewed in Reeves *Trends Mol. Med.* 12:237-240, 2006). There are mouse strains with segmental trisomies, such as Ts65Dn, which carries a segment (15.6-Mb) of mouse chromosome 16 on a marker chromosome (Reeves et al., *Nat. Genet.* 11:177-184, 1995). The extra $T(17^{16})65Dn$ marker chromosome produces a trisomy for the mouse orthologs of about half of the human genes on chr. 21. Mice display a number of DS-like phenotypes, including an overall reduction in size and growth rate, altered noradrenergic transmission in the hippocampus and cerebral cortex and degeneration of basal forebrain cholinergic neurons, and defects in cranial bone development (Hill et al., *J. Anat.* 210:394-405, 2007; Olson et al., *Hum. Mol. Genet.* 16:774-782, 2007). In addition, trisomic females have smaller and fewer litters and trisomic males display hypospermia. Another mouse model, Ts16, carries an essentially complete third copy of mouse chr. 16, involving a Robertsonian translocation of chr 16 (Epstein et al., *Ann. NY Acad. Sci.* 450:157-168, 1985). As with other mouse full trisomies, these mice die during fetal development, so all studies are done on the fetal mice or cells derived from fetuses. However, for our purposes the severity of the phenotype would potentially make the therapeutic benefits clearer, if we should see an increase in viability upon inactivation of one copy of chromosome 16. The Rb(6.16)24Lub/Rb(16.17) 7BnrF$_1$ Robertsonian translocation mouse strain (used to generate Ts16) and the Ts65Dn mouse strain are available from the Jackson Laboratory.

Another interesting mouse DS model (Tc1) carries an almost complete human chromosome 21, and exhibits several characteristics that are reminiscent of Down Syndrome (O'Doherty et al., *Science* 309:2033-2037, 2005). However, this model is less attractive as it is not clear how well human Xist would silence a human chromosome in an otherwise mouse nucleus; our prior study of mouse/human hybrids showed that human Xist RNA may not localize properly. Thus, we have decided to begin with the Ts65n model which carries a partial chr 16 trisomy and is more straightforward. We summarize the approach for this system, but other models can be tested similarly.

Generation of Mouse Down's Syndrome ES Cells and iPS Cells:

The Ts65Dn mouse model (B6EiC3Sn a/A-Ts($17^{16}$) 65Dn) has been obtained from the Jackson Laboratory (stock number 001924) (Roper et al., *Genetics* 172:437-443, 2006). Female T($17^{16}$)65Dn mice have been mated to 129SV/EV males, and a number of litters produced. DS pups have been identified by karyotyping cytogenetic preps, and using FISH on interphase cells from tail tip fibroblasts and whole blood.

Generation of Trisomic ES Cells:

Blastocysts will be harvested from the mating of Ts65Dn females with 129SV/EV males, to derive ES cells, using standard procedures DS embryos can also be generated by somatic cell nuclear transfer of a fibroblast from a Ts65Dn mouse into an enucleated normal mouse egg.

Generation of Trisomic iPS Cells:

Fibroblasts from DS pups have been isolated and iPS cells generated using lentivirus expression of 4 pluripotency genes (mOct4, mSox2, mKlf4, mc-Myc). Twenty hours post-transduction, the virally transduced cells were resuspended in ES cell growth medium and re-seeded. The following day the pluripotency genes were induced with doxycycline. Colonies that appear (ours started showing up by day 3), are replated onto inactivated feeder MEFs. Doxycycline is removed once colonies are verified to express the other pluripotency markers (SSEA-1, Nanog, etc), between 14 and 22 days. Resulting colonies are then cultured on feeders in the absence of dox, similar to normal mouse ES cells. These iPS cells can now be used to target Xist to chromosome 16.

Targeting the Xist Transgene to a Trisomic Chromosome in Mouse Cells and Assessing Silencing of Chr 16:

The Xist transgene will be targeted into a specific region of chromosome 16 in the trisomic iPS cells. We will target the region critical for Down's syndrome on chromosome 16, using as preferred targeting sites some of the genes important to the pathology of Down's syndrome (e.g., Runx-1, APP, Dyrk1A, etc). The transgene can have a constitutive or inducible promoter. We have begun to construct a targeting transgene which incorporates Xist cDNA sequences from an Xist cDNA that we have obtained by Anton Wutz (Research Institute of Molecular Pathology, Vienna) (Savarese et al., *Mol. Cell Biol.* 26:7167-7177, 2006). This Xist transgene contains an inducible promoter and Xist cDNA, but lacks the 3' sequence necessary for counting. Thus, it will not be susceptible to random inactivation in the female ES cells. We are modifying this transgene with appropriate promoters, homologous targeting sequences, and inducible system to make it appropriate for targeting the Xist transgene to the specific chromosome in iPS cells. It will be expressed during cell differentiation, for optimal silencing.

We will be using established mouse gene targeting protocols on our iPS cells. We are currently designing an Xist targeting construct using a vector previously validated to efficiently target the Runx1 gene. Runx1 is located in the critical region of chr16, has been linked to leukemia, and likely plays a role in the hematological abnormalities seen in DS individuals (mouse and human). The targeting vector can also include a GFP mini-gene to facilitate identification of transgenic cells and to confirm silencing of this gene. Selectable markers will facilitate identification of properly targeted clones, using known procedures. Similarly, targeting can be to the APP gene which is known to be important to Alzheimer's Disease or other gene important in other diseases.

In mouse models of DS, we can not only manipulate mouse ES or iPS cells, which are known to support chromosome silencing, but also test two critical points in the proof-of-principle: that stable silencing of the third chromosome (carrying an Xist transgene) can be achieved, and that this can have ameliorating effects on the disorder, at the whole organism level. Our plan is to initially target the Xist transgene into a trisomic chromosome of "Down Syndrome" mouse ES/iPS cells, induce silencing and confirm that it silences, and then generate mice (or chimeric mice) from these engineered ES/iPS cells. If this procedure successfully silences and mitigates the phenotype, we can use an inducible promoter to induce Xist expression at later stages of development, to determine how late effective silencing and mitigation of the disorder can be achieved. Also, the original TS64DN non-modified mice may also be used to examine the effects of reintroducing bone marrow, after chromosome modification, on the hematological abnormalities in DS mice (these studies are further detailed below).

Figure 5:
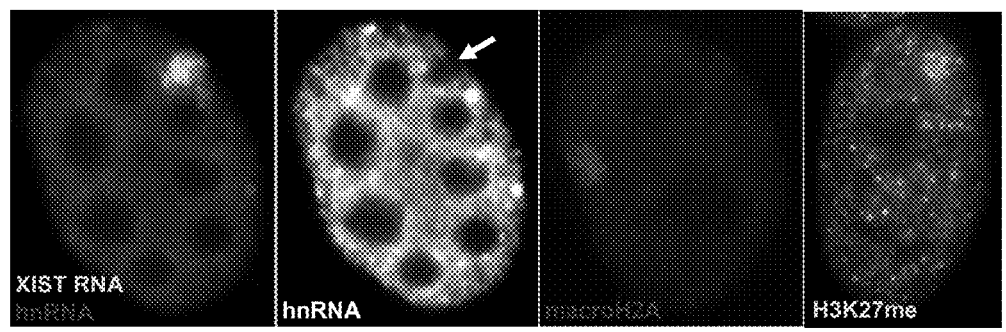
FIG. 5 is a panel of four images of the same cell showing, from left to right, Xist RNA localization, hnRNA, macroH2A localization, and H3K27me localization.

Validation of Targeting and Silencing:

As we have previously published, single cell analysis by molecular cytological methods (immunofluorescence and FISH), will be used to validate targeting and the extent of chromosomal silencing in differentiated iPS cell cultures (FIG. 5). RNA FISH for single genes or real-time PCR or microarrays will be used to examine gene expression levels in targeted versus non-targeted iPS cells. We will initially determine by fluorescence in situ hybridization whether the Xist gene is expressing and producing a localized accumulation that "paints" the chromosome. This is a very distinctive relationship of RNA to the chromosome that is almost always correlated with silencing, which our lab first discovered and established (Clemson et al., *J. Cell Biol.* 132:259-275, 1996). If Xist RNA coated chromosomes are observed, we will then use other Xi hallmarks (e.g., hybridization to hnRNA, immunofluorescence to H3K27 methylation or macroH2A) to further validate the silencing, as shown in FIG. 5 and in our published papers.

In addition, as stated above, we will generate mice from the modified mouse iPS (or ES) cells to test the prediction that the trisomic chromosome can be silenced and the deleterious phenotype will be substantially ameliorated (this is further detailed below).

Experiments in Human Primary or iPS Down Syndrome Cells:

Several DS human cell types are available to generate DS iPS lines from, including DS patient fibroblasts and bone marrow. We have acquired three primary DS fibroblast lines and two bone marrow cell lines, and have TERT immortalized one female DS fibroblast line. We plan to generate iPS cells from both primary as well a TERT immortalized DS lines, using lentivirus expression of 4 pluripotency genes similar to the methodology used in developing the mouse DS iPS cell lines. We have also acquired a DS iPS line from Harvard Stem Cell Institute.

Studies in Human Primary Cells:

Although iPS cells can now be made from primary lines, we can also test the developmental competence of terminally differentiated primary human cells to support silencing in response to an inducible Xist transgene integrated into an autosome. This may help define whether more differentiated cell types may also be available for chromosome therapy in the future. Some of our studies have been aimed at determining whether somatic or only stem cells can support chromosome silencing of an autosome. A prior study of transgenic mouse ES cells concluded that Xist did not induce silencing just a few days after the earliest embryonic differentiation (Wutz et al.), however this study examined silencing just two days after Xist expression. We have shown that adult human somatic cells can initiate silencing of an autosome carrying an Xist transgene (Hall et al., *Proc. Natl. Acad. Sci. USA* 99:8677-8682). However, the study indicated this took at least 10 days to occur in somatic cells. Thus, we will examine chromosome silencing after two or more weeks and are hopeful that somatic cells will largely retain the ability to induce chromosome silencing, albeit more slowly than in ES cells. Our recent findings indicate that human ES cells (hESCs) also support silencing of the normal X chromosome in culture similar to that seen for the mouse. We have also derived a sub-line of neural stem cells (from hESCs), and we will test their competence to support silencing, which may be particularly relevant to future DS therapeutic applications. It may also be possible to partially reprogram somatic cells, such that they more closely resemble adult stem cells instead of ES/iPS cells, and assess the competence of these partially reprogrammed cells to inactivate.

Wutz lab (Savarese et al., *Mol. Cell Biol.* 26:7167-7177, 2006) suggests that bone marrow stem cells may retain capacity to support chromosome silencing post-embryonic differentiation, but our close reading of this data suggests to us that some or many more cell-types in fetal or adult mice still retain the capacity for X-inactivation. For reasons summarized below, we are particularly interested in testing this strategy in DS bone marrow cells. Thus, for these experiments, rather than use transformed cell lines, we will test several different primary somatic cell types, including DS patient fibroblasts and bone marrow cells, primary diploid myoblasts, epithelial cells, and trisomic amniocytes (available from Coriell Cell Repositories, Camden, N.J.).

The developmental competence of these cells will be compared to TERT immortalized primary DS lines, and embryonic and neural stem cells, including those derived from induced pluripotent stem (iPS) cells generated from patient somatic cells.

These questions regarding the developmental competence of cells to enact chromosome silencing do not require targeted integration (we will use the methodology that provides the highest efficiency of integration), and is similar to work we have done successfully with transformed cell lines.

Incorporation of the ZFN Technology to Target the Xist Transgene to a Trisomic Chromosome in Human Cells and Assess Silencing of Chr 21 (or Chr 13):

We will test the best strategies to target human Chr 21 (or Chr 13) and to confirm the effectiveness of silencing. Conventional targeting strategies as well as a new zinc-finger based methodology will be used for targeting the Xist transgene to Chr 21. This will be assessed both with and without the use of selection, and by using the endogenous or an inducible promoter (as in our papers). Selection might be utilized with future ES/iPS methodologies, but would not be an option in vivo; see Moehle et al. (*Proc. Natl. Acad. Sci. USA*, 104:3055-3060, 2007). The constructs lack the sequences 3' to Xist that trigger the "counting" mechanism, so this will not complicate results.

We will use site-specific targeting, using zinc finger nucleases (ZFNs). This approach provides much higher integration efficiency, without a requirement for selection. More specifically, this method uses the cells own machinery for double strand break repair to improve the efficiency of gene targeting. The zinc finger motifs can be engineered to recognize almost any sequence, and we will engineer ZFN transgenes that target two or more sites of Chr. 21. The transgene encoding the ZFN can be introduced along with a vector carrying the gene to be inserted flanked by a few hundred by of DNA homologous to the target site. Recent studies have achieved targeted integration rates of about 5 to 20% without selection with integration of up to 8 kb of DNA (Urnov et al., *Nature* 435:646-651, 2005; Moehle et al., *Proc. Natl. Acad. Sci. USA* 104U; 3055-3060, 2007). If very high efficiency is obtained, it is possible that we could get integration into two copies of the chromosome in some cells. If this occurs, we will target polymorphic sites. In addition, these methods have shown particular promise for use in human ES cells.

We will begin these studies in 293 cancer cells that transfect at very high efficiency, and then move on to TERT immortalized trisomy 21 fibroblasts, and iPS cells generated from these DS lines. We anticipate that most autosomal material is competent to be inactivated in response to Xist RNA. However, because there is some sequence specificity to this process, we will determine the effectiveness of chromosome 21 silencing specifically using molecular cytological assays. Presuming this shows silencing, we will use microarray analysis to determine the profile of gene expression for Chr. 21 genes, in comparison to the trisomic cells (without the transgene) and normal cells. In addition to the trisomy 21 cells, one of the human ES cell lines approved by the NIH carries a trisomy for chr. 13. We will study Chr. 13 inactivation in these cells, both as undifferentiated ES cells and as cells differentiated along a neuronal pathway.

Utilizing Random Integration of Xist:

In some studies, we will use the ZFN technology described above, but analyses can also be done using our protocol for random integration with the same constructs and transfection approach that we have successfully used before (Hall et al. 2002b; Chow et al. 2007). In these experiments, transgenes can be designed to select against cells in which the transgene has not integrated. If integration is into a disomic chromosome which is then silenced, this would create a functional monosomy, which would reduce or severely reduce cell viability. In contrast, if the random integration involved the trisomic chromosome in a DS cell line, there is likely to be a growth advantage to these "corrected" cells within the population, and this, coupled with selection against cells where integration generated a functional monosomy, may generate a strong selection for the desired cells in which the random integration was into the trisomic chromosome even without targeting methodologies. This same natural selective disadvantage of functionally monosomic cells may provide a natural protection against the less frequent occurrence that two of the trisomic chromosomes are silenced, as such cells would be selected against as they are in human development. (In individuals mosaic for Down Syndrome where a non-disjunction even generates a trisomic cell-line and a monosomic cell line, the monosomic cell line is not see; these cells die.). However, we have also shown that transfectants can be selected for drug expression (prior to chromosome inactivation), and the integration site and impact on chromosome silencing can be determined in several different clones or in pooled populations of random integrants.

Further Studies Using the Down's Syndrome Mouse Models

Use Trisomic Mouse ES/iPS Cells Carrying the Xist-Transgene to Generate Mice and Assess Phenotype:

The targeted ES/iPS cells can be injected into blastocysts of albino C57Bl/6 E3.5 to generate mice in which coat color changes can be used to assess the degree of chimerism or into the blastocysts of trisomic Ts65n blastocysts. The latter mice would be "mosaic" for the Xist-transgenic trisomic cells and uncorrected trisomic cells, providing a good model of partial correction. In addition, routine methods using blastocysts that have undergone tetraploid fusion can generate mice completely derived from the modified ES cells.

To assess the corrective effects of Xist-mediated silencing of the T($17^{16}$)65Dn chromosome in this model for DS, we will measure birth weight and growth throughout the postnatal period, as well as correction of defects in craniofacial skeletal formation. Bone defects have been analyzed in mice using X-rays and microCT analysis (Lengner et al., *J. Cell Biol.* 172:909-921, 2006), and we will also examine hematopoietic properties and make appropriate crosses to determine whether the Xist transgene corrects the deficiency in male fertility. In addition, maintenance of gene silencing will be assayed in a variety of organs by both qPCR for genes present of the T($17^{16}$)65Dn chromosome as well as by analysis of GFP expression, and by standard molecular cytological methods.

Relevance of Trisomy 21 to Hematological Abnormalities and Bone Marrow Stem Cells:

We will test this strategy to silence the trisomic chromosome in bone marrow cells. There is a direct and measurable clinical impact of trisomy on bone marrow function. DS children develop hematological abnormalities, ranging from mild to severe. For example, neonates with DS commonly develop a transient myeloproliferative disorder (TMD; also termed transient leukemia). Although TMD often is self-resolving, it is highly predictive of later development of acute leukemia, can result directly in significant morbidity, and may be fatal in 10-20% of affected infants. Most importantly, it is well established that DS children have a greatly increased risk of progressing to leukemia, such that 2% of childhood leukemia patients have DS. The incidence of ALL and AML, is 20 fold higher than normal, and the normally very rare AMKL (acute megakaryoblastic leukemia) is increased a remarkable 500 fold (Lange, *Br. J. Haematol.* 110:512-524, 2000). Finally, most DS children have MCV (mean corpuscular volume) above the 97$^{th}$ percentile. While not a significant clinical concern, this is indicative of disordered hematopoiesis and provides a prevalent "marker" of the syndrome (also in the mouse DS model), that could be readily evaluated in "corrected" cells.

Regarding the Ts65Dn model (above), an important report just appeared which demonstrates that it also provides a good model for many of the hematological abnormalities seen in human DS (Kirsammer et al., *Blood* 111(2), 2008). The DS mice exhibit a highly penetrant myeloproliferative disease, as well as macrocytosis, dysplastic megakaryocyte morphology, and myelofibrosis. Therefore, we will test the chromosome silencing strategy in bone marrow stem cells from the Ts65Dn mouse. In addition to the clinical impact of trisomy on hematological abnormalities, the study of bone marrow is advantageous because it is an accessible source of cells that can be genetically manipulated, and then replaced. Furthermore, a study of the Xist mechanism, using random integration of inducible Xist transgenes, provided evidence that hematopoeitic precursor cells of adult mice are most readily competent to support chromosome silencing (Savarese et al., *Mol. Cell Biol.* 26:7167-7177, 2006). (This study was unrelated to any concept regarding therapeutic use of Xist transgenes.) We will use inducible mouse Xist transgene constructs as described in Savarese (supra), and we can include in these constructs GFP, which will facilitate sorting and enrichment of cells carrying the Xist transgene. Ultimately, the silencing of the transgenic chromosome would be verified using procedures described above and the modified cells will be reintroduced, after bone marrow ablation by radiation. At various intervals after "chromosome correction", hematological analysis will be carried out to determine whether or to what extent the aforementioned anomalies of the DS mouse, particularly the myeloproliferative disease and the prevalent macrocytosis, have been ameliorated.

Use of Inducible Xist Transgene to Test Phenotypic Benefits Later in Development:

To determine the extent of the therapeutic benefit achieved when the trisomic chromosome is silenced later in development, we will generate ES/iPS cells that contain the doxycyclin inducible Xist transgene, or another inducible Xist construct (e.g., Cre/Lox mediated removal of drug resistance gene generating a new construct where Xist is transcribed using the drug resistance promoter). The inducible Xist transgene can then be turned on in both undifferentiated ES/iPS cells as well as at different times during differentiation and in terminally differentiated cells to assess the developmental competence of inactivation.

The same inducible transgenic iPS/ES cells can be used to induce the "rescue" later in fetal development, allowing the evaluation of phenotypic benefits in more differentiated cells. Addition of doxycyclin to the drinking water of the pregnant dams bearing the chimeric mice for 14 days should result in activation of the tet promoter controlling Xist expression, and Xist-mediated silencing of the T($17^{16}$)65Dn chromosome. A similar strategy has been used previously in mice to regulate Xist expression in hematopoietic precursor cells (Savarese et al., *Mol. Cell Biol.* 26:7167-7177, 2006).

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising:
a vector comprising a nucleic acid construct comprising:
a silencing sequence encoding an Xist RNA; and
first and second sequences homologous to a site of desired integration in human chromosome 13, 18, or 21 or mouse chromosome 16 that specifically direct insertion of the silencing sequence into human chromosome 13, 18, or 21 or mouse chromosome 16 by homologous recombination.

2. The composition of claim 1, wherein the silencing sequence is a full-length Xist gene sequence.

3. The composition of claim 1, wherein the silencing sequence is an Xist gene sequence exclusive of one or more introns.

4. The composition of claim 1, wherein the silencing sequence comprises about 6 kb to about 10 kb of exon 1 of an Xist gene sequence.

5. The composition of claim 4, wherein the silencing sequence comprises the Xist cDNA sequence having accession number M97168 or a biologically active fragment or other variant thereof.

6. The composition of claim 1, wherein the silencing sequence comprises a biologically active fragment or other biologically active variant of a naturally occurring Xist gene sequence.

7. The composition of claim 1, further comprising a regulatory sequence.

8. The composition of claim 7, wherein the regulatory sequence is a constitutively active, inducible, tissue-specific, or developmental stage-specific promoter.

9. The composition of claim 1, wherein the first and second sequences direct insertion of the silencing sequence into a polymorphic region of the targeted chromosome.

10. The composition of claim 1, wherein the first and second sequences direct insertion of the silencing sequence into an APP gene.

11. The composition of claim 1, wherein the vector comprising the nucleic acid construct further comprises a selectable marker.

12. An isolated trisomic cell comprising the composition of claim 1.

13. The isolated trisomic cell of claim 12, wherein the cell is a somatic cell or a stem cell.

14. An isolated cell comprising the composition of claim 1.

15. The isolated cell of claim 14, wherein the cell is a germ cell, a stem cell, or a precursor cell.

16. The isolated cell of claim 15, wherein the stem cell is an embryonic stem cell, an adult stem cell, or an induced pluripotent stem cell.

17. The isolated cell of claim 16, wherein the adult stem cell is a hematopoietic stem cell or a neural stem cell.

18. The isolated cell of claim 14, wherein the cell is a differentiated cell.

19. The isolated cell of claim 18, wherein the differentiated cell is a fibroblast or neuron.

20. A method of reducing gene expression from a trisomic human chromosome 13, 18, or 21 or mouse chromosome 16, the method comprising:
    identifying a subject with a trisomic human chromosome 13, 18, or 21 or mouse chromosome 16;
    harvesting neural cells from the subject;
    transfecting the neural cells with a vector comprising a nucleic acid construct comprising:
        a silencing sequence encoding an XIST/Xist RNA; and
        first and second sequences homologous to a site of desired integration in human chromosome 13, 18, or 21 or mouse chromosome 16 that specifically direct insertion of the silencing sequence into human chromosome 13, 18, or 21 or mouse chromosome 16 by homologous recombination; and
    administering to the subject a sufficient number of the transfected neural cells to reduce gene expression from the trisomic chromosome.

21. The method of claim 20, wherein the neural cells are neural stem cells.

22. The method of claim 20, wherein the silencing sequence is a full-length XIST/Xist gene sequence.

23. The method of claim 20, wherein the silencing sequence is an XIST/Xist gene sequence exclusive of one or more introns.

24. The method of claim 20, wherein the silencing sequence comprises about 6 kb to about 10 kb of exon 1 of an XIST/Xist gene sequence.

25. The method of claim 24, wherein the silencing sequence comprises the XIST/Xist cDNA sequence having accession number M97168 or a biologically active fragment or other variant thereof.

26. The method of claim 20, wherein the silencing sequence comprises a biologically active fragment or other biologically active variant of a naturally occurring XIST/Xist gene sequence.

27. The method of claim 20, further comprising a regulatory sequence.

28. The method of claim 27, wherein the regulatory sequence is a constitutively active, inducible, tissue-specific, or developmental stage-specific promoter.

29. The method of claim 20, wherein the first and second sequences direct insertion of the silencing sequence into a polymorphic region of the targeted chromosome.

30. The method of claim 20, wherein the first and second sequences direct insertion of the silencing sequence into an APP gene.

31. The method of claim 20, wherein the vector comprising the nucleic acid construct further comprises a selectable marker.

32. The method of claim 20, wherein the subject is a human.

* * * * *